(12) United States Patent
Choi

(10) Patent No.: US 9,018,253 B2
(45) Date of Patent: Apr. 28, 2015

US009018253B2

(54) PHENYLCARBAMATE COMPOUND AND MUSCLE RELAXANT CONTAINING THE SAME

(75) Inventor: Yong Moon Choi, Fort Lee, NJ (US)

(73) Assignee: Bio-Pharm Solutions Co., Ltd. (KR)

(*) Notice: Subject to any disclaimer, the term of this patent is extended or adjusted under 35 U.S.C. 154(b) by 196 days.

(21) Appl. No.: 13/175,025

(22) Filed: Jul. 1, 2011

(65) Prior Publication Data

US 2013/0005801 A1    Jan. 3, 2013
US 2014/0051753 A9    Feb. 20, 2014

Related U.S. Application Data

(60) Provisional application No. 61/360,952, filed on Jul. 2, 2010.

(51) Int. Cl.
| | | |
|---|---|---|
| C07C 261/00 | (2006.01) | |
| A61K 31/27 | (2006.01) | |
| C07C 271/12 | (2006.01) | |
| C07C 271/24 | (2006.01) | |

(52) U.S. Cl.
CPC ............... A61K 31/27 (2013.01); C07C 271/12 (2013.01); C07C 271/24 (2013.01)

(58) Field of Classification Search
CPC ..... A61K 31/27; C07C 271/12; C07C 271/24
USPC ............ 560/163, 164, 115, 32; 514/487, 484, 514/489
See application file for complete search history.

(56) References Cited

U.S. PATENT DOCUMENTS

| | | | |
|---|---|---|---|
| 2,884,444 | A | 4/1959 | Berger et al. |
| 2,937,119 | A | 5/1960 | Berger et al. |
| 3,265,727 | A | 8/1966 | Bossinger et al. |
| 3,265,728 | A * | 8/1966 | Bossinger et al. ............ 560/164 |
| 3,313,692 | A | 4/1967 | Bossinger et al. |
| 3,313,696 | A | 4/1967 | Bossiner et al. |
| 3,313,699 | A | 4/1967 | Bossinger et al. |
| 3,313,700 | A | 4/1967 | Bossinger et al. |
| 3,600,427 | A | 8/1971 | Verbiscar |
| 6,103,759 | A | 8/2000 | Choi et al. |
| 7,385,076 | B2 | 6/2008 | Patel et al. |
| 7,442,438 | B2 | 10/2008 | Boulos et al. |
| 7,737,141 | B2 | 6/2010 | Kimura et al. |
| 2001/0034365 | A1 | 10/2001 | Choi et al. |
| 2002/0156127 | A1 | 10/2002 | Plata-Salaman et al. |
| 2002/0165273 | A1 | 11/2002 | Plata-Salaman et al. |
| 2004/0138299 | A1 | 7/2004 | Cahill et al. |
| 2006/0194873 | A1 | 8/2006 | Choi et al. |
| 2008/0090903 | A1 | 4/2008 | Pandey et al. |
| 2008/0103198 | A1 | 5/2008 | Haas |
| 2008/0317883 | A1 | 12/2008 | Choi et al. |
| 2009/0221640 | A1 | 9/2009 | Briggner et al. |
| 2010/0048629 | A1 | 2/2010 | Gage |
| 2012/0184762 | A1 | 7/2012 | Choi |
| 2013/0165408 | A1 | 6/2013 | Choi |
| 2013/0165409 | A1 | 6/2013 | Choi |
| 2013/0165410 | A1 | 6/2013 | Choi |
| 2013/0165509 | A1 | 6/2013 | Choi |
| 2013/0184338 | A1 | 7/2013 | Choi |
| 2013/0203846 | A1 | 8/2013 | Choi |

FOREIGN PATENT DOCUMENTS

| | | |
|---|---|---|
| CN | 1208402 A | 2/1999 |
| CN | 1536992 A | 10/2004 |
| CN | 1536993 A | 10/2004 |
| CN | 101208402 A | 6/2008 |
| CN | 101472913 A | 7/2009 |
| JP | 61-271992 A | 12/1986 |
| WO | WO-2006/033947 A2 | 3/2006 |
| WO | WO-2008/013213 A1 | 1/2008 |
| WO | WO-2008/124848 A1 | 10/2008 |
| WO | WO-2012002773 A2 | 1/2012 |
| WO | WO2012096458 A2 | 7/2012 |

OTHER PUBLICATIONS

"International Application Serial No. PCT/KR2011/004862, International Search Report mailed Feb. 27, 2012", 3 pgs.
"International Application Serial No. PCT/KR2011/004862, Written Opinion mailed Feb. 27, 2012", 5 pgs.
Girijavallabhan, V. M., et al., "Synthesis of the antifungal agent SCH 42427 (SM 9164)", (Bioorganic & Medicinal Chemistry Letters, 1(7), 349-353), ASC on STN, Accession No. 1992:41371, (1991), 1 pg.
Jiao, P., et al., "A Sequential O-Nitrosoaidol and Grignard Addition Process: An Enantio- and Diastereoselective Entry to Chiral 1,2-Diols", Angewandte Chemie. International Edition, 48(18), (2009), 3333-3336.
"U.S. Appl. No. 13/338,863, Non Final Office Action mailes Dec. 10, 2013", 6 pgs.
"U.S. Appl. No. 13/338,863, Response filed Oct. 28, 2013 to Restriction Requirement mailed Sep. 27, 2013", 9 pgs.
"U.S. Appl. No. 13/338,863, Restriction Requirement mailed Sep. 27, 2013", 9 pgs.
"European Application Serial No. 12169507.6, European Search Report maled Sep. 26, 2012", 8 pgs.
"International Application Serial No. PCT/KR2011/010105, International Search Report mailed Aug. 7, 2012", 3 pgs.
"International Application Serial No. PCT/KR2011/010105, Written Opinion mailed Aug. 7, 2012", 4 pgs.
Amarante, G. W., et al., "Acyloins from Morita-Baylis-Hillman adducts: an alternatice approach to the racemic total synthesis of bupropion", Tettrahedron Letters, 49, (2008), 3744-3748.
Bausch, C. C., et al., "Cross Silyl Benzoin Additions Catalyzed by Lanthanum Tricyanide", J. Org.Chem., 69, (2004), 4283-4285.
Citterio, et al., "", J. Chem. Soc. Perkin Tran. I, (1983), 891-896.
Eid, Jr., C. N., et al., "Enantiomerically Pure Ketals in Synthesis, Diastereoselective Formation of Beta-Keto and Beta-Hydroxy Ketals", Tetrahedron Letters, 32(4), (1991), 461-464.
Ghosh, et al., "", J. Org. Chem., (2010), 500-511.

(Continued)

Primary Examiner — T. Victor Oh

(74) Attorney, Agent, or Firm — Schwegman Lundberg & Woessner, P.A.

(57) ABSTRACT

A novel phenylcarbamate compound and a pharmaceutical composition containing the same are provided. More specifically, a novel phenylcarbamate compound, a composition for muscle relaxation containing the phenylcarbamate compound as an active ingredient, and a method of muscle relaxation comprising administering a therapeutically effective amount of the phenylcarbamate compound, are provided.

8 Claims, No Drawings

(56) References Cited

OTHER PUBLICATIONS

Joseph, S. P., et al., "Reaction of chlorosulfonyl isocyanate with 1,2-diols", Synthetic Communications, 18(18), (1988), 2295-2302.
Morimoto, et al., "", J. Chem. Soc. Perkin Trans. II, (1986), 1205-1209.
"U.S. Appl. No. 13/338,863, Notice of Allowance mailed Apr. 29, 2014", 9 pgs.
U.S. Appl. No. 13/338,863, Response filed Mar. 6, 2014 to Non Final Office Action mailed Dec. 10, 2013, 10 pgs.
"U.S. Appl. No. 13/757,654, Examiner Interview Summary mailed May 29, 2014", 3 pgs.
"U.S. Appl. No. 13/727,654, Final Office Action mailed Jan. 29, 2014", 27 pgs.
"U.S. Appl. No. 13/757,654, Non Final Office Action Sep. 9, 2013", 21 pgs.
"U.S. Appl. No. 13/727,654, Response filed Jun. 27, 2014 to Final Office Action mailed Jan. 29, 2014", 21 pgs.
"U.S. Appl. No. 13/727,654, Response filed Aug. 16, 2013 to Restriction Requirement mailed Jul. 31, 2013", 6 pgs.
"U.S. Appl. No. 13/727,654, Response filed Dec. 9, 2013 to Non Final Office Action mailed Sep. 9, 2013", 17 pgs.
"U.S. Appl. No. 13/727,654, Restriction Requirement mailed Jul. 31, 2013", 7 pgs.
"U.S. Appl. No. 13/727,659, Non Final Office Action mailed Apr. 22, 2014", 6 pgs.
"U.S. Appl. No. 13/727,661, Non Final Office Action mailed Jun. 24, 2014", 11 pgs.
"U.S. Appl. No. 13/727,661, Response filed Nov. 15, 2013 to Restriction Requirement mailed Oct. 15, 2013", 6 pgs.
"U.S. Appl. No. 13/727,661, Restriction Requirement mailed Oct. 15, 2013", 6 pgs.
"U.S. Appl. No. 13/727,663, Non Final Office Action mailed Feb. 4, 2014", 9 pgs.
"U.S. Appl. No. 13/727,663, Non Final Office Action mailed Jul. 3, 2014", 17 pgs.
"U.S. Appl. No. 13/727,663, Response filed Nov. 6, 2013 Restriction Requirement mailed Oct. 7, 2013", 6 pgs.
"U.S. Appl. No. 13/727,663, Response Filed May 1, 2014 to Non Final Office Action mailed Feb. 4, 2014", 46 pgs.
"U.S. Appl. No. 13/727,663, Restriction Requirement mailed Oct. 7, 2013", 6 pgs.
"Canadian Application Serial No. 2,815,460, Office Action mailed Mar. 6, 2014", 4 pgs.
"Chinese Application Serial No. 201180032939.0, Office Action dated Mar. 31, 2014", (w/ English Translation), 8 pgs.
"Chinese Application Serial No. 201180032939.0, Office Action dated Sep. 17, 2013", (w/ English Translation), 12 pgs.
"Chinese Application Serial No. 201180063001.5, Office Action mailed Mar. 14, 2014", (w/ English Translation), 13 pgs.
"Epilepsy", by Mayo Clinic Staff, [online]. Retrieved from the Internet: <URL: http://www.mayoclinic.com/health/epilepsy/DS00342/METHOD =print&DSECTION=all>, (2013), 14 pgs.
"European Application Serial No. 12169507.6, Office Action mailed Feb. 21, 2014", 6 pgs.
"European Application Serial No. 12169507.6, Office Action mailed Dec. 3, 2012", 2 pgs.
"European Application Serial No. 12169507.6, Response filed May 17, 2013 to Office Action mailed Dec. 3, 2012", 14 pgs.
"International Application Serial No. PCT/KR2012/011469, International Search Report mailed Apr. 22, 2013", 4 pgs.
"International Application Serial No. PCT/KR2012/011469, Written Opinion mailed Apr. 22, 2013", 7 pgs.
"International Application Serial No. PCT/KR2012/011470. International Search Report mailed Apr. 22, 2013", 4 pgs.
"International Application Serial No. PCT/KR2012/011470. Written Opinion mailed Apr. 22, 2013", 5 pgs.
"International Application Serial No. PCT/KR2012/011471. International Search Report mailed Apr. 22, 2013", 4 pgs.
"International Application Serial No. PCT/KR2012/011471. Written Opinion mailed Apr. 22, 2013", 5 pgs.
"International Application Serial No. PCT/KR2012/011472, International Search Report mailed Apr. 23, 2013", 4 pgs.
"International Application Serial No. PCT/KR2012/011472, Written Opinion mailed Apr. 23, 2013", 5 pgs.
"International Application Serial No. PCT/KR2012/011474, International Search Repors mailed Apr. 23, 2013", 4 pgs.
"International Application Serial No. PCT/KR2012/011474, Written Opinion mailed Apr. 23, 2013", 5 pgs.
"International Application Serial No. PCT/KR2012/011475. International Search Report mailed Apr. 23, 2013", 4 pgs.
"International Application Serial No. PCT/KR2012/011475, Written Opinion mailed Apr. 23, 2013", 5 pgs.
"Japanese Application Serial No. 2013-518264, Office Action mailed Mar. 11, 2014", (w/ English Translation), 6 pgs.
Cannon, J. G., "Chapter Nineteen—Analog Design", *In Burger's Medicinal Chemistry and Drug Discovery*. Fifth Edition. vol. I: Principles and Practice. Wiley-Interscience, (1995), 783-802.
Edin, M., et al., "Ruthenium- and lipase-catalyzed DYKAT of 1,2-diols: an enantioselective synthesis of *syn*-1,2-diacetates", *Tetrahedron: Asymmetry*, 17(4), (2006), 708-715.
Girijavallabhan, V. M., "Synthesis of the Antifungal Agent Sch 42427 (SM 9164)", *Bioorganic & Medicinal Chemistry Letters*. 1(7), (191), 349-352.
Lehmkuhle, M. J, et al., "A Simple Quantitative Method for Analyzing Electrographic Status Epilepticus in Rats", *J. Neuropysiol.*, 101, (1009), 1660-1670.
Ohta, H., et al., "Reductive $C_2$-Homologation of Substituted Benzaldehydes by Fermenting Baker's Yeast", *Agric. Biol. Chem.*, 50(5), (1986), 1261-1266.
Sheridan, R. P, "The Most Common Chemical Replacements in Drug-Like Compounds", *J. Chem. Inf. Comupt. Sci.*, vol. 42, (2002), 103-108.
Wijesekera, L. C., et al., "Amyotrophic lateral sclerosis", *Orphanet Journal of Rare Diseases*, 4:3, (2009), 1-22.

* cited by examiner

PHENYLCARBAMATE COMPOUND AND MUSCLE RELAXANT CONTAINING THE SAME

CROSS-REFERENCE TO RELATED APPLICATION

This application claims the benefit of priority under 35 U.S.C. 119(e) to U.S. Provisional Application No. 61/360,952 filed in the United States Patent and Trademark Office on Jul. 2, 2010.

BACKGROUND OF THE INVENTION (a) Field of the Invention

The present invention relates to novel phenyl carbamate compounds and pharmaceutical compositions containing the compound. More specifically, the present invention relates to phenyl carbamate compounds and a pharmaceutically acceptable salt thereof, which have a considerably high muscle relaxation effect and low toxicity, and compositions for muscle relaxation containing the compounds and/or pharmaceutically acceptable salt thereof as an active ingredient.

(b) Description of the Related Art

Myotony or spasm is frequently observed as a sequel of cerebrovascular disorders such as stroke or sequel of head injuries, and is not easy to treat.

Myotony, or spasm, is one of skeletal muscle dysfunction diseases due to increase of muscle tone, and caused by central nervous system damage due to various causes such as external injury, cerebrovascular accidents, and the like. The muscle tension is caused by various causes, for example, cervicoomobrachial syndrome which is caused by abnormal posture, fatigue, age-related spine deformity, and the like, and causes spasticity or pain in skeletal muscles of the neck, shoulders, arms, waist, and back; spastic paralysis causing disability of voluntary movement due to muscle hypertonia of hands and feet by disorder of central nervous system such as cerebrovascular disorder; and a combination thereof, thereby resulting in serious hindrances to normal life.

In particular, spastic paralysis is a serious disorder with accompanying symptoms including muscle tension and/or muscular stiffness of hands and feet, difficulty in walking, and the like, thererby causing serious hindrances to normal life. Centrally acting muscle relaxants relieve muscle tension by blocking receptors associated with stimulating muscular function or stimulating receptors associated with inhibiting muscular function, or reducing excessively activated reflex function.

Such centrally acting muscle relaxants may include Methocarbaamol, Chlormezanon, Carisoprodol, Eperisone, Phenprobamide, and the like. However, these drugs act on interneuron of the spinal cord, thereby inhibiting monosynaptic and polysynaptic reflexes, and thus, may cause side effects, such as central nervous inhibition, muscle weakness, and the like.

U.S. Pat. No. 3,313,692 discloses a racemic carbamate compound useful as a therapeutic agent for the central nervous system with decreased side effects compared to cholinergic agent. U.S. Pat. Nos. 2,884,444, 2,937,119, and 3,265,727 suggest dicarbamate compounds useful as therapeutic agents for central nervous system disorders, and U.S. Pat. No. 2,937,119 discloses a N-isopropyl-2-methyl-2-propyl-1,3-propanediol dicarbamate, which was released with the trademark of Soma as a muscle relaxant.

Muscle relaxants are used for improving various symptoms, such as cervicoomobrachial syndrome (shoulder-arm-neck syndrome), lumbago (lower back pain), herniation of intervertebral disk, cerebrovascular disorders, vascular disorders of the spinal cord, spastic spinal paralysis, cervical spondylosis, cerebral palsy, sequelae of injuries (spinal cord injuries, head injuries), spinocerebellar degeneration, multiple sclerosis, amyotrophic lateral sclerosis, and the like, which are associated with muscle spasm involved in musculoskeletal diseases, and also used as an adjuvant to anesthestic agent.

Considering the various and valuable uses of muscle relaxants as aforementioned, development of more effective muscle relaxant is needed.

SUMMARY OF THE INVENTION

To satisfy such requirement, an embodiment of the present invention provides a phenyl carbamate compound represented by Chemical Formula 1; a racemate, an enantiomer, a diastereomer, a mixture of enantiomers, or a mixture of diastereomers thereof; or a pharmaceutically acceptable salt thereof:

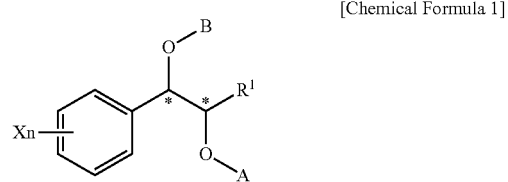

[Chemical Formula 1]

wherein,

X is a halogen, for example, chlorine, fluorine, iodine, or bromine,

N is an integer from 1 to 5, for example, 1 or 2,

R1 is a C1-C4 linear or branched alkyl group, for example, methyl group, ethyl group, isopropyl group, or butyl group, A is hydrogen or a carbamoyl derivative represented by

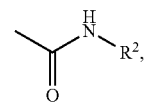

B is hydrogen or a carbamoyl derivative represented by

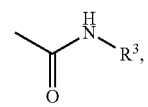

A and B are not carbamoyl derivatives at same time, and

R2 and R3 may be the same as or different from each other, and independently selected from the group consisting of hydrogen, a linear or branched alkyl group of C1-C4, for example C1-C3, a cycloalkyl group of C3-C8, for example C3-C7, and benzyl group, and more specifically, R2 and R3 may be the same as or different from each other, and independently selected from the group consisting of hydrogen, methyl group, propyl group, isopropyl group, cyclopropyl group, cyclohexyl group, bicycloheptane group, and benzyl group.

Another embodiment provides a pharmaceutical composition containing provides a phenyl carbamate compound represented by Chemical Formula 1; a racemate, an enantiomer, a diastereomer, a mixture of enantiomers, or a mixture of diastereomers thereof; or a pharmaceutically acceptable salt thereof, as an active ingredient.

Another embodiment provides a method of muscle relaxation comprising:

administering a therapeutically effective amount of a phenyl carbamate compound represented by Chemical Formula 1; a racemate, an enantiomer, a diastereomer, a mixture of enantiomers, or a mixture of diastereomers thereof; or a pharmaceutically acceptable salt thereof, to a subject in need of muscle relaxation.

Another embodiment provides a method of treating and/or preventing a disease associated with muscle spasm involved in musculoskeletal diseases, comprising:

administering a therapeutically effective amount of a phenyl carbamate compound represented by Chemical Formula 1; a racemate, an enantiomer, a diastereomer, a mixture of enantiomers, or a mixture of diastereomers thereof; or a pharmaceutically acceptable salt thereof, to a subject in need of treating and/or preventing a disease associated with muscle spasms relates to musculoskeletal diseases.

DETAILED DESCRIPTION OF THE EMBODIMENTS

Upon attempting to discover a muscle relaxant with more excellent efficacy and decreased side effects, the present inventors found that substituted phenyl carbamate compounds represented by the following Chemical Formula 1 exhibit a considerably excellent activity of muscle relaxation with very low toxicity, to complete the present invention.

Therefore, an embodiment provides a phenyl carbamate compound represented by the following Chemical Formula 1:

[Chemical Formula 1]

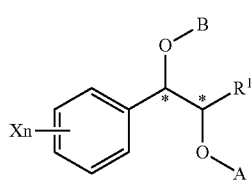

wherein,

X is a halogen, for example, chlorine, fluorine, iodine, or bromine

N is an integer from 1 to 5, for example, 1 or 2,

R1 is a C1-C4 linear or branched alkyl group, for example, methyl group, ethyl group, isopropyl group, or butyl group, A is hydrogen or a carbamoyl derivative represented by

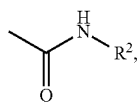

B is hydrogen or a carbamoyl derivative represented by

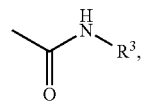

A and B are not carbamoyl derivatives at same time, and

R2 and R3 may be the same as or different from each other, and independently selected from the group consisting of hydrogen, a linear or branched alkyl group of C1-C4, for example C1-C3, a cycloalkyl group of C3-C8, for example C3-C7, and benzyl group, and more specifically, R2 and R3 may be the same as or different from each other, and independently selected from the group consisting of hydrogen, methyl group, propyl group, isopropyl group, cyclopropyl group, cyclohexyl group, bicycloheptane group, and benzyl group.

In a concrete embodiment, when X is chlorine and n is 1, A and B may not be hydrogen at the same time, or R1 may not be methyl group, or R2 may not be hydrogen.

In another concrete embodiment, when X is chlorine and n is 1, A and B may not be hydrogen at the same time, or R1 may not be methyl group or not be ethyl group, or R2 may not be hydrogen, and when X is chlorine and n is 2, R1 may not be ethyl group, or R2 may not be hydrogen.

Since the compound has two chiral carbons at the $1^{st}$ and $2^{nd}$ positions from the X substituted phenyl group, they may be in the form of a racemate, an enantiomer, a diastereomer, a mixture of enantiomers, or a mixture of diastereomers.

Alternatively, the compound may be in the form of a pharmaceutically acceptable salt. The pharmaceutically acceptable salt may include an additional salt of acid or base, and its stereochemical isomer. For example, the compound may be in the form of an additional salt of an organic or inorganic acid. The salt may not be specially limited, and include any salts that maintain the activities of their parent compounds, with no undesirable effects, in the subject, when they are administered to the subject. Such salts may include inorganic and organic salts, such as salts of acetic acid, nitric acid, aspartic acid, sulfonic acid, sulfuric acid, maleic acid, glutamic acid, formic acid, succinic acid, phosphoric acid, phthalic acid, tannic acid, tartaric acid, hydrobromic acid, propionic acid, benzene sulfonic acid, benzoic acid, stearic acid, lactic acid, bicarbonic acid, bisulfuric acid, bitartaric acid, oxalic acid, butyric acid, calcium edetate, carbonic acid, chlorobezoic acid, citric acid, edetic acid, toluenesulfonic acid, fumaric acid, gluceptic acid, esilic acid, pamoic acid, gluconic acid, methyl nitric acid, malonic acid, hydrochloric acid, hydroiodic, hydroxynaphtholic acid, isethionic acid, lactobionic acid, mandelic acid, mucic acid, naphthylic acid, muconic acid, p-nitromethanesulfonic acid, hexamic acid, pantothenic acid, monohydrogen phosphoric acid, dihydrogen phosphoric acid, salicylic acid, sulfamic acid, sulfanilic acid, methane sulfonic acid, and the like. The additional salts of base may include salts of akali metal or alkaline earth metal, such as salts of ammonium, lithium, sodium, potassium, magnesium, calcium, and the like; salts having an organic base, such as benzathine, N-methyl-D-glucamine, hydrabamine, and the like; and salts having an amino acid such as arginine, lysine, and the like. In addition, these salts may be converted to a released form by treating with a proper base or acid.

As demonstrated in the following experimental examples, the compound of Chemical Formula 1; a racemate, an enantiomer, a diastereomer, a mixture of enantiomers, or a mixture of diastereomers thereof; or pharmaceutically acceptable salt thereof exhibits an excellent effect on muscle relaxation.

Therefore, another embodiment provides a pharmaceutical composition containing a compound of Chemical Formula 1; a racemate, an enantiomer, a diastereomer, a mixture of enantiomers, or a mixture of diastereomers thereof; or a pharmaceutically acceptable salt thereof, as an active ingredient.

The pharmaceutical composition may be a muscle relaxant.

In addition, since a muscle relaxant can be used for improving and/or treating symptoms of diseases associated with muscle spasm, the pharmaceutical composition capable of acting as muscle relaxant may also be used as a pharmaceutical composition for preventing and/or treating a muscle spasm associated disease, for example, cervicobrachial syndrome (shoulder-arm-neck syndrome), lumbago (lower back pain), herniation of intervertebral disk, cerebrovascular disorders, vascular disorders of the spinal cord, spastic spinal paralysis, cervical spondylosis, cerebral palsy, sequelae of injuries (spinal cord injuries, head injuries), spinocerebellar degeneration, multiple sclerosis, amyotrophic lateral sclerosis, and the like.

The pharmaceutical composition may be formulated in various forms for oral or parenteral administration. For example, the pharmaceutical composition may be formulated in the oral administration form, such as a tablet, pill, soft or hard capsule, liquid, suspension, emulsion, syrup, granules, elixirs, and the like. In addition to the active ingredient, the oral administration form may further include pharmaceutically acceptable and conventional components, for example, a diluent such as lactose, dextrose, sucrose, mannitol, sorbitol, cellulose, glycine, and the like; a lubricant such as silica, talc, stearic acid, magnesium or calcium salt thereof, polyethyleneglycol, and the like.

In the case that the oral administration form is a tablet, it may further include a binder such as magnesium aluminium silicate, starch paste, gelatin, tragacanth, methylcellulose, sodium carboxymethylcellulose, polyvinylpirrolidine, and the like; and optionally include one or more additives selected from the group consisting of a disintegrant such as starch, agar, arginic acid or sodium salt thereof, an absorbent, a colorant, a flavoring, a sweetener, and the like.

Alternatively, the pharmaceutical composition may also be formulated in a parenteral administration form, which can be administered by subcutaneous injection, intravenous injection, intramuscular injection, injection into thoracic cavity, and the like. In order to formulate the parenteral administration form, the pharmaceutical composition may be prepared as a solution or suspension wherein the active ingredient is dissolved in water together with a stabilizer and/or a buffering agent, and such solution or suspension formulation may be prepared as a dosage form in ample or vial.

The pharmaceutical composition may be sterilized, and/or include further additives such as a preservative, a stabilizer, a hydrating agent, an emulsification accelerator, a salt and/or buffering agent for osmoregulation, and the like, and/or further therapeutically effective ingredients. The pharmaceutical composition may be formulated by any conventional method for mixing, granulating, coating, and the like.

The pharmaceutical composition may be administered to a mammal including human, in the therapeutically effective amount of 0.01 to 750 mg/kg (body weight), preferably 0.1 to 500 mg/kg (body weight) per one day, based on the active ingredient. The therapeutically effective amount may be administered through oral or parenteral pathway, one or two or more times per one day.

The therapeutically effective amount and the administration pathway of the present pharmaceutical composition may be properly adjusted by a person skilled in the relevant field considering the conditions of the subject (patient), desired effects, and the like.

Another embodiment provides a method of muscle relaxation comprising:

administering a therapeutically effective amount of a phenyl carbamate compound represented by Chemical Formula 1; a racemate, an enantiomer, a diastereomer, a mixture of enantiomers, or a mixture of diastereomers thereof; or a pharmaceutically acceptable salt thereof, to a subject in need of muscle relaxation.

The method of muscle relaxation may further include the step of identifying the subject in need of muscle relaxation, prior to the step of administration.

Another embodiment provides a method of treating and/or preventing a disease associated with muscle spasm, comprising:

administering a therapeutically effective amount of a phenyl carbamate compound represented by Chemical Formula 1; a racemate, an enantiomer, a diastereomer, a mixture of enantiomers, or a mixture of diastereomers thereof; or a pharmaceutically acceptable salt thereof, to a subject in need of treating and/or preventing a disease associated with muscle spasms.

The method of treating and/or preventing a disease associated with muscle spasm may further include the step of identifying the subject in need of treating and/or preventing a disease associated with muscle spasm, prior to the step of administration.

Another embodiment provides a phenyl carbamate compound represented by Chemical Formula 1; a racemate, an enantiomer, a diastereomer, a mixture of enantiomers, or a mixture of diastereomers thereof; or a pharmaceutically acceptable salt thereof, for the use of muscle relaxation, or treatment and/or prevention of a disease associated with muscle spasm; and a use of a phenyl carbamate compound represented by Chemical Formula 1; and for the use of preparing a muscle relaxant or a pharmaceutical composition for treating and/or preventing a disease associated with muscle spasms.

The subject to be treated with the compound may be any mammal, preferably human.

The carbamate compound of the present invention may prepared by the following reaction formula.

Reaction Formula I: Syn-addition Diol

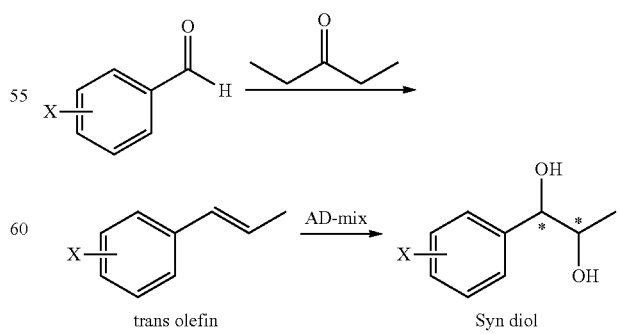

A Syn diol compound used in the synthesis of the carbamate compound may be synthesized by dihydroxylation of a trans-olefin compound. A diol compound having optical activity may be synthesized using a sharpless asymmetric dihydroxylation catalyst.

Reaction Formula II: Anti-addition Diol

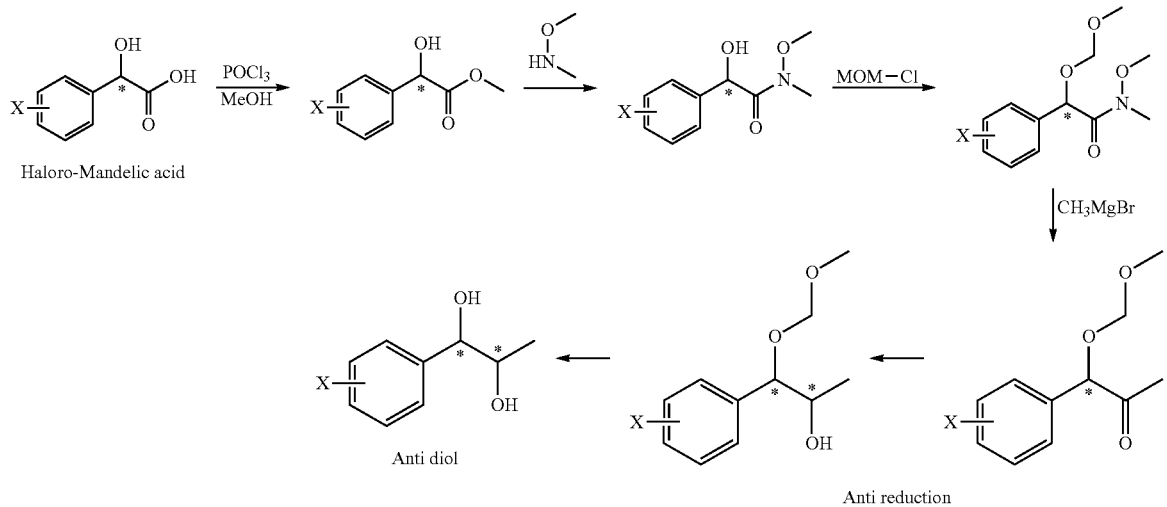

Haloro-Mandelic acid

Anti diol

Anti reduction

An optically active substance of anti-diol may be synthesized using an anti-reduction reagent after synthesizing a hydroxy-ketone compound using Haloro-Mandelic acid.

Reaction Formula III: Carbamation reaction

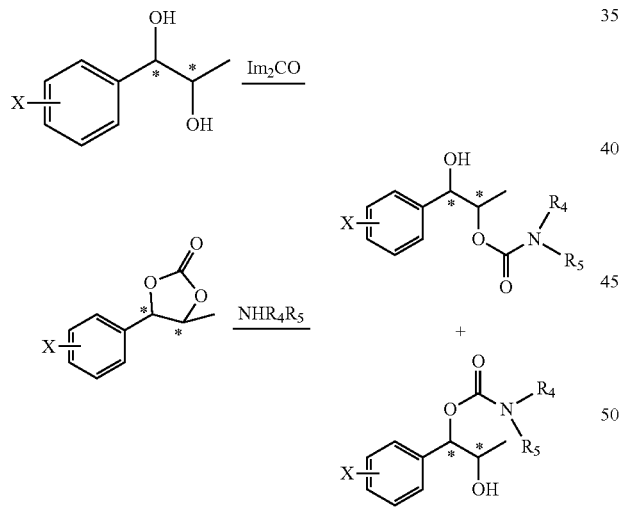

In the Reaction Formula III, R4 and R5 may be the same as or different from each other, and independently selected from the group consisting of hydrogen, a linear or branched alkyl group of C1-C4, for example C1-C3, a cycloalkyl group of C3-C8, for example C3-C7, and benzyl group, and more specifically, R4 and R5 may be the same as or different from each other, and independently selected from the group consisting of hydrogen, methyl group, propyl group, isopropyl group, cyclopropyl group, cyclohexyl group, bicycloheptane group, and benzyl group.

Two substances in the form of regioisomers of a single carbamate of diol having halogen substituent at phenyl ring may be separated by flash column chromatography to obtain two kinds of single carbamate compounds.

EXAMPLE

The present invention is further explained in more detail with reference to the following examples. These examples, however, should not be interpreted as limiting the scope of the present invention in any manner.

Preparation Example 1

Synthesis of 1-(2-chlorophenyl)-trans-1-propene

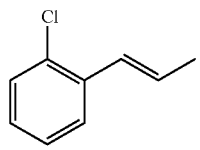

48 ml of 2-chlorobenzenaldehyde (0.42 mol) and 49.7 ml of 3-pentanone (0.47 mol) were dissolved in 600 mL of hexane in flask, and then stirred with raising the temperature. 53.6 ml of Boron trifluoride etherate ($BF_3OEt_2$, 0.42 mol) was added to the resultant under reflux conditions. When the reaction was completed, water was added thereto. After layer separation, the obtained organic layer was washed twice with 1M sodium hydroxide solution (1M NaOH), and then the separated organic layer was washed with water. The separated organic layer was dehydrated with anhydrous magnesium sulfate ($MgSO_4$) and concentrated. The concentrated residue was purified by a silica gel column chromatography to produce the title compound (38 g, yield 58%). $^1$H NMR(400

MHz, CDCl₃)δ1.94(d, J=4.8 Hz, 3H), 6.24(m, 1H), 6.78(d, J=14 Hz, 1H), 7.11~7.51(m, 4H)

Preparation Example 2

Synthesis of 1-(2-chlorophenyl)-trans-1-butene

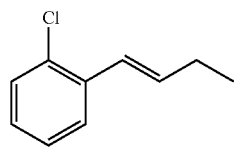

The substantially same method as described in Preparation Example 1 was conducted, except that 3-heptanone was used instead of 3-pentanone, to obtain the title compound (2.9 g, yield 83%).

$^1$H NMR(400 MHz, CDCl₃)δ1.14(d, J=7.6 Hz, 3H), 2.29~2.33(m, 2H), 6.28(dt, J=16 Hz, 6.4 Hz, 1H), 6.78(d, J=15.6 Hz, 1H), 7.13~7.54(m, 4H)

Preparation Example 3

Synthesis of 1-(2-chlorophenyl)-3-methyl-trans-1-butene

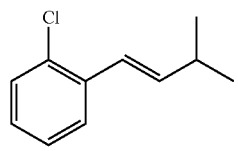

The substantially same method as described in Preparation Example 1 was conducted, except that 2,6-dimethyl-heptan-4-one was used instead of 3-pentanone, to obtain the title compound (8.0 g, yield 50~90%).

$^1$H NMR(400 MHz, CDCl₃)δ1.14(d, J=6.8 Hz, 6H), 2.25~2.57(m, 1H), 6.20(dd, J=16 Hz, 7.2 Hz, 1H), 7.64(d, J=16 Hz, 1H), 7.12~7.54(m, 4H)

Preparation Example 4

Synthesis of 1-(2-chlorophenyl)-trans-1-hexene

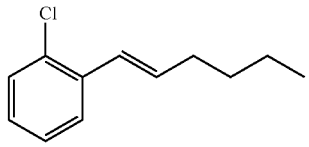

The substantially same method as described in Preparation Example 1 was conducted, except that 6-undecanone was used instead of 3-pentanone, to obtain the title compound (10 g, yield 85%).

$^1$H NMR(400 MHz, CDCl₃) δ0.96(t, J=7.2 Hz, 3H), 1.33~1.56(m, 4H), 2.26~2.32(m, 4H), 6.24(dt, J=15.6 Hz, 7 Hz, 1H), 6.78(d, J=16 Hz, 1H), 7.13~7.54(m, 4H)

Preparation Example 5

Synthesis of 1-(2,4-dichlorophenyl)-trans-1-propene

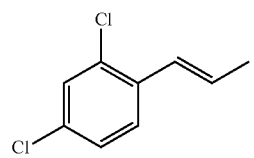

The substantially same method as described in Preparation Example 1 was conducted, except that 2,4-dichlorobenzenaldehyde was used instead of 2-chlorobenzenaldehyde, to obtain the title compound (2.4 g, yield 57%).

$^1$H NMR(400 MHz, CDCl₃) δ1.95(dd, J=6.8 Hz, 1.6 Hz, 3H), 6.24(m, 1H), 6.72(d, J=15.6 Hz, 1H), 7.18~7.44(m, 3H)

Preparation Example 6

Synthesis of 1-(2,4-dichlorophenyl)-trans-1-butene

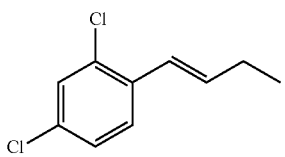

The substantially same method as described in Preparation Example 5 was conducted, except that 3-heptanone was used instead of 3-pentanone, to obtain the title compound (2.1 g, yield 90%).

$^1$H NMR(400 MHz, CDCl₃) δ1.14(d, J=7.6 Hz, 3H), 2.20~2.33(m, 2H), 6.26(dt, J=16 Hz, 6.8 Hz, 1H), 6.70(d, J=15.6 Hz, 1H), 7.18~7.46(m, 3H)

Preparation Example 7

Synthesis of 1-(2,6-dichlorophenyl)-3-methyl-trans-1-butene

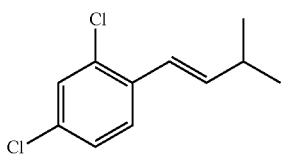

The substantially same method as described in Preparation Example 5 was conducted, except that 2,6-dimethyl-heptan-4-one was used instead of 3-pentanone, to obtain the title compound (0.23 g, yield 10~40%).

¹H NMR(400 MHz, CDCl₃) δ1.15(d, J=6.8 Hz, 6H), 2.53~2.58(m, 1H), 6.19(dd, J=16.4 Hz, 6.8 Hz, 1H), 6.31(d, J=16.4 Hz, 1H), 7.18~7.46(m, 3H)

Preparation Example 8

Synthesis of 1-(2,4-dichlorophenyl)-trans-1-hexene

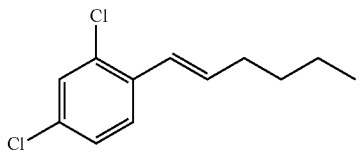

The substantially same method as described in Preparation Example 5 was conducted, except that 6-undecanone was used instead of 3-pentanone, to obtain the title compound (3.2 g, yield 40~80%).

¹H NMR(400 MHz, CDCl₃) δ0.96(t, J=7.2 Hz, 3H), 1.38~1.52(m, 4H), 2.25~2.31(m, 2H), 6.22(dt, J=15.6 Hz, 6.8 Hz, 1H), 6.70(d, J=15.6 Hz, 1H), 7.18~7.46(m, 3H)

Preparation Example 9

Synthesis of 1-(2,6-dichlorophenyl)-trans-1-propene

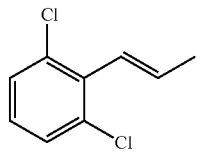

The substantially same method as described in Preparation Example 1 was conducted, except that 2,6-dichlorobenzenaldehyde was used instead of 2-chlorobenzenaldehyde, to obtain the title compound (0.4 g, yield 10~40%).

¹H NMR(400 MHz, CDCl₃) δ1.98(d, J=8 Hz, 3H), 6.23~6.31(m, 1H), 6.40(d, J=16 Hz, 1H), 7.05~7.32(m, 3H)

Preparation Example 10

Synthesis of 1-(2,6-dichlorophenyl)-trans-1-butene

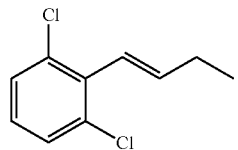

The substantially same method as described in Preparation Example 9 was conducted, except that 3-heptanone was used instead of 3-pentanone, to obtain the title compound (1.2 g, yield 10~40%).

¹H NMR(400 MHz, CDCl₃) δ1.17(t, J=7.6 Hz, 3H), 2.30~2.37(m, 2H), 6.29(dt, J=16.4 Hz, 6 Hz, 1H), 6.37(d, J=16.4 Hz, 1H), 7.05~7.32(m, 3H)

Preparation Example 11

Synthesis of 1-(2,6-dichlorophenyl)-3-methyl-trans-1-butene

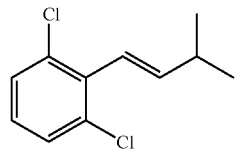

The substantially same method as described in Preparation Example 9 was conducted, except that 2,6-dimethyl-heptan-4-one was used instead of 3-pentanone, to obtain the title compound (0.23 g, yield 10~40%).

¹H NMR(400 MHz, CDCl₃) δ1.15(d, J=6.8 Hz, 6H), 2.53~2.58(m, 1H), 6.19(dd, J=16.4 Hz, 6.8 Hz, 1H), 6.31(d, J=16.4 Hz, 1H), 7.05~7.32(m, 3H)

Preparation Example 12

Synthesis of 1-(2,6-dichlorophenyl)-trans-1-hexene

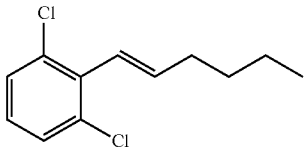

The substantially same method as described in Preparation Example 9 was conducted, except that 6-undecanone was used instead of 3-pentanone, to obtain the title compound (0.2 g, yield 10~40%).

¹H NMR(400 MHz, CDCl₃) δ0.99(t, J=7.2 Hz, 3H), 1.14~1.59(m, 4H), 2.30~2.36(m, 2H), 6.24(dt, J=16 Hz, 6.6 Hz, 1H), 6.38(d, J=16.4 Hz, 1H), 7.05~7.33(m, 3H)

Preparation Example 13

Synthesis of 1-(2,3-dichlorophenyl)-trans-1-propene

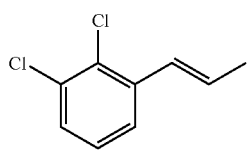

The substantially same method as described in Preparation Example 1 was conducted, except that 2,3-dichlorobenzenaldehyde was used instead of 2-chlorobenzenaldehyde, to obtain the title compound (0.2 g, yield 10~40%).

¹H NMR(400 MHz, CDCl₃) δ1.94(d, J=4.8 Hz, 3H), 6.24 (m, 1H), 6.78(d, J=14 Hz, 1H), 7.11~7.51(m, 3H)

Preparation Example 14

Synthesis of 1-(2-chlorophenyl)-(S,S)-1,2-propanediol

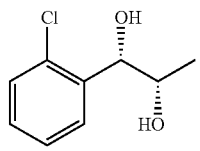

1-(2-chlorophenyl)-trans-1-propene (1.5 g, Preparation Example 1) was dissolved in 30 mL of the mixture of t-BuOH/H₂O (1:1(V/V)). At 0° C., AD-mix-α (Aldrich, U.S.A.) (13.7 g) and methane sulfone amide (CH₃SO₂NH₂, 0.76 g, 0.0080 mol) were added thereto and stirred for overnight. When the reaction was completed, the obtained product was washed with an aqueous solution of sodium sulfite (Na₂SO₃) and ethylacetate (EA). Then, the organic layer was dehydrated with anhydrous magnesium sulfate (MgSO₄), filtrated, and concented under reduced pressure. The concentrated residue was purified by a silica gel column chromatography to produce the title compound (1.65 g, yield 90%).

¹H NMR(400 MHz, CDCl₃) δ1.20(d, J=6.4 Hz, 3H), 2.48 (d, J=4.0 Hz 1H), 2.92(d, J=4.4 Hz, 1H), 3.93~3.97(m, 1H), 4.97(t, J=4.8 Hz, 1H), 7.22~7.51(m, 4H)

¹³CNMR (100 MHz, CDCl₃) δ18.8, 71.5, 74.4, 127.1, 128.1, 128.9, 129.5, 132.6, 138.9

Preparation Example 15

Synthesis of 1-(2-chlorophenyl)-(R,R)-1,2-propanediol

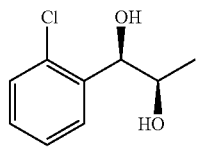

1-(2-chlorophenyl)-trans-1-propene (2.5 g, Preparation Example 1) was dissolved in 50 mL of the mixture of t-BuOH/H₂O (1:1(V/V)). At 0° C., AD-mix-α (Aldrich, U.S.A.) (23.5 g) and methane sulfone amide (CH₃SO₂NH₂, 1.27 g, 0.013 mol) were added thereto and stirred for overnight. When the reaction was completed, the obtained product was washed with an aqueous solution of sodium sulfite (Na₂SO₃) and ethylacetate (EA). Then, the organic layer was dehydrated with anhydrous magnesium sulfate (MgSO₄), filtrated, and concented under reduced pressure. The concentrated residue was purified by a silica gel column chromatography to produce the title compound (2.96 g, yield 90%).

¹H NMR(400 MHz, CDCl₃) δ1.20(d, J=6.4 Hz, 3H), 2.48 (d, J=4.0 Hz, 1H), 2.92(d, J=4.4 Hz, 1H), 3.93~3.97(m, 1H), 4.97(t, J=4.8 Hz, 1H), 7.22~7.51(m, 4H)

Preparation Example 16

Synthesis of the mixture of 1-(2-chlorophenyl)-(S, S)-1,2-propanediol and 1-(2-chlorophenyl)-(R,R)-1, 2-propanediol

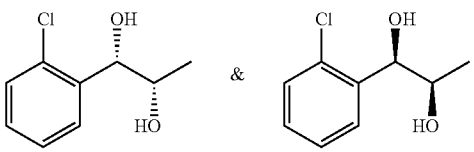

1-(2-chlorophenyl)-trans-1-propene (6.53 g, Preparation Example 1) was dissolved in 45 mL of the mixture of acetone/t-BuOH/H₂O (5:1:1 V/V). At the room temperature, N-methylmorpholine-N-oxide (7.51 g) and OsO₄(0.54 g) were added thereto and stirred for 2-3 hours. When the reaction was completed, the obtained product was washed with water and methylenechloride (MC). Then, the organic layer was dehydrated with anhydrous magnesium sulfate (MgSO₄), filtrated, and concented under reduced pressure. The concentrated residue was purified by a silica gel column chromatography to produce the title compound (6.42 g, yield 80%).

¹H NMR(400 MHz, CDCl₃) δ1.20(d, J=6.4 Hz, 3H), 2.48 (d, J=4.0 Hz, 1H), 2.92(d, J=4.4 Hz, 1H), 3.93~3.97(m, 1H), 4.97(t, J=4.8 Hz, 1H), 7.22~7.51(m, 4H)

Preparation Example 17

Synthesis of 1-(2-chlorophenyl)-(S,S)-1,2-butanediol

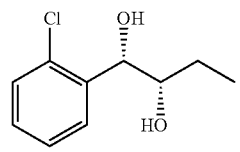

The substantially same method as described in Preparation Example 14 was conducted, except that 1-(2-chlorophenyl)-trans-1-butene (Preparation Example 2) was used instead of 1-(2-chlorophenyl)-trans-1-propene (Preparation Example 1), to obtain the title compound (0.36 g, yield 95%).

¹H NMR(400 MHz, CDCl₃) δ1.01(t, J=7.4 Hz, 3H), 1.52-1.65(m, 2H), 2.01(d, J=4.4 Hz, 1H), 2.74(d, J=5.2 Hz, 1H), 3.69-3.75(m, 1H), 5.05(t, J=5.0 Hz, 1H), 7.23~7.54(m, 4H)

Preparation Example 18

Synthesis of 1-(2-chlorophenyl)-(R,R)-1,2-butanediol

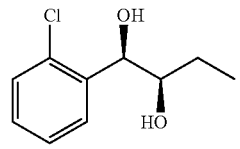

The substantially same method as described in Preparation Example 15 was conducted, except that 1-(2-chlorophenyl)-trans-1-butene (Preparation Example 2) was used instead of 1-(2-chlorophenyl)-trans-1-propene (Preparation Example 1), to obtain the title compound (0.84 g, yield 60~95%).

$^1$H NMR(400 MHz, CDCl$_3$) δ1.01(t, J=7.4 Hz, 3H), 1.52~1.65(m, 2H), 2.01(d, J=4.4 Hz, 1H), 2.74(d, J=5.2 Hz, 1H), 3.69~3.75(m, 1H), J=5.0 Hz, 1H), 7.23~7.54(m, 4H)

Preparation Example 19

Synthesis of the mixture of 1-(2-chlorophenyl)-(S,S)-1,2-butanediol and 1-(2-chlorophenyl)-(R,R)-1,2-butanediol

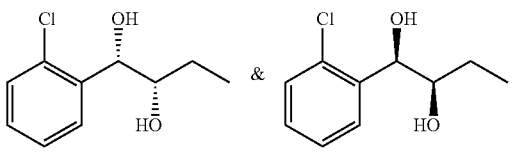

The substantially same method as described in Preparation Example 16 was conducted, except that 1-(2-chlorophenyl)-trans-1-butene (Preparation Example 2) was used instead of 1-(2-chlorophenyl)-trans-1-propene (Preparation Example 1), to obtain the title compound (5.1 g, yield 60~90%).

$^1$H NMR(400 MHz, CDCl$_3$) δ1.01(t, J=7.4 Hz, 3H), 1.52~1.65(m, 2H), 2.01(d, J=4.4 Hz, 1H), 2.74(d, J=5.2 Hz, 1H), 3.69~3.75(m, 1H), 5.05(t, J=5.0 Hz, 1H), 7.23~7.54(m, 4H)

Preparation Example 20

Synthesis of 1-(2-chlorophenyl)-3-methyl-(S,S)-1,2-butanediol

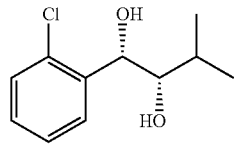

The substantially same method as described in Preparation Example 14 was conducted, except that 1-(2-chlorophenyl)-3-methyl-trans-1-butene (Preparation Example 3) was used instead of 1-(2-chlorophenyl)-trans-1-propene (Preparation Example 1), to obtain the title compound (0.96 g, yield 60~90%).

$^1$H NMR(400 MHz, CDCl$_3$) δ1.07(t, J=7.2 Hz, 6H), 1.83~1.89(m, 1H), 1.92(d, J=5.6 Hz, 1H), 2.69(d, J=6.4 Hz, 1H), 3.53~3.56(m, 1H), 5.22~5.25(m, 1H), 7.23~7.55(m, 4H)

Preparation Example 21

Synthesis of 1-(2-chlorophenyl)-3-methyl-(R,R)-1,2-butanediol

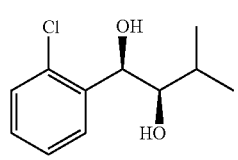

The substantially same method as described in Preparation Example 15 was conducted, except that 1-(2-chlorophenyl)-3-methyl-trans-1-butene (Preparation Example 3) was used instead of 1-(2-chlorophenyl)-trans-1-propene (Preparation Example 1), to obtain the title compound (4.2 g, yield 60~90%).

$^1$H NMR(400 MHz, CDCl$_3$) δ1.07(t, J=7.2 Hz, 6H), 1.82~1.90(m, 1H), 1.93(d, J=5.6 Hz, 1H), 2.79(d, J=6 Hz, 1H), 3.53~3.57(m, 1H), 5.23~5.25(m, 1H), 7.23~7.54(m, 4H)

Preparation Example 22

Synthesis of the mixture of 1-(2-chlorophenyl)-3-methyl-(S,S)-1,2-butanediol and 1-(2-chlorophenyl)-3-methyl-(R,R)-1,2-butanediol

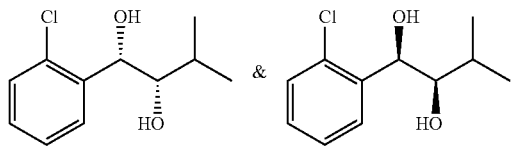

The substantially same method as described in Preparation Example 16 was conducted, except that 1-(2-chlorophenyl)-3-methyl-trans-1-butene (Preparation Example 3) was used instead of 1-(2-chlorophenyl)-trans-1-propene (Preparation Example 1), to obtain the title compound (0.8 g, yield 60~90%).

$^1$H NMR(400 MHz, CDCl$_3$) δ1.07(t, J=7.2 Hz, 6H), 1.83~1.90(m, 1H), 1.92(d, J=5.6 Hz, 1H), 2.69(d, J=6.4 Hz, 1H), 3.53~3.56(m, 1H), 5.22~5.25(m, 1H), 7.23~7.55(m, 4H)

Preparation Example 23

Synthesis of 1-(2-chlorophenyl)-(S,S)-1,2-hexanediol

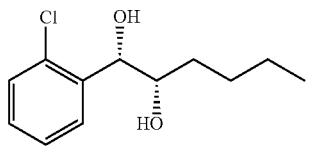

The substantially same method as described in Preparation Example 14 was conducted, except that 1-(2-chlorophenyl)-trans-1-hexene (Preparation Example 4) was used instead of 1-(2-chlorophenyl)-trans-1-propene (Preparation Example 1), to obtain the title compound (0.37 g, yield 90%).

$^1$H NMR(400 MHz, CDCl$_3$) δ0.90(t, J=7.2 Hz, 3H), 1.35~1.65(m, 6H), 2.08(d, J=4.4 Hz, 1H), 2.71(d, J=5.2 Hz, 1H), 3.78~3.83(m, 1H), 5.04(t, J=5.0 Hz, 1H), 7.23~7.53(m, 4H)

Preparation Example 24

Synthesis of 1-(2-chlorophenyl)-(R,R)-1,2-hexanediol

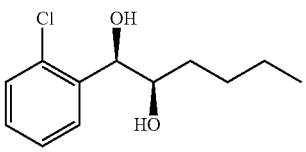

The substantially same method as described in Preparation Example 15 was conducted, except that 1-(2-chlorophenyl)-trans-1-hexene (Preparation Example 4) was used instead of 1-(2-chlorophenyl)-trans-1-propene (Preparation Example 1), to obtain the title compound (4.2 g, yield 60~90%).
$^1$H NMR(400 MHz, CDCl$_3$) δ0.91(t, J=6.6 Hz, 3H), 1.35~1.65(m, 6H), 2.08(d, J=4.8 Hz, 1H), 2.70(d, J=5.2 Hz, 1H), 3.80~3.83(m, 1H), 5.05(t, J=5.0 Hz, 1H), 7.24~7.56(m, 4H)

Preparation Example 25

Synthesis of the mixture of 1-(2-chlorophenyl)-(S,S)-1,2-hexanediol and 1-(2-chlorophenyl)-(R,R)-1,2-hexanediol

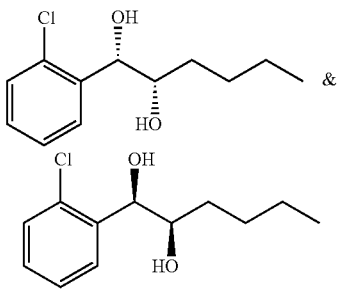

The substantially same method as described in Preparation Example 16 was conducted, except that 1-(2-chlorophenyl)-trans-1-hexene (Preparation Example 4) was used instead of 1-(2-chlorophenyl)-trans-1-propene (Preparation Example 1), to obtain the title compound (7.9 g, yield 60~90%).
$^1$H NMR(400 MHz, CDCl$_3$) δ0.90(t, J=7.2 Hz, 3H), 1.26~1.55(m, 6H), 2.08(d, J=4.4 Hz, 1H), 2.71(d, J=5.6 Hz, 1H), 3.78~3.84(m, 1H), 5.04(t, J=3.2 Hz, 1H), 7.24~7.55(m, 4H)

Preparation Example 26

Synthesis of 1-(2,4-dichlorophenyl)-(S,S)-1,2-propanediol

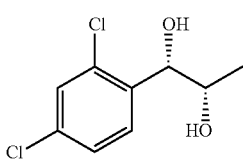

The substantially same method as described in Preparation Example 14 was conducted, except that 1-(2,4-dichlorophenyl)-trans-1-propene (Preparation Example 5) was used instead of 1-(2-chlorophenyl)-trans-1-propene (Preparation Example 1), to obtain the title compound (0.33 g, yield 60~95%).
$^1$H NMR(400 MHz, CDCl$_3$) δ1.22(d, J=6.4 Hz, 3H), 2.10 (d, J=4.4 Hz, 1H), 2.71(d, J=4.8 Hz, 1H), 3.90~3.95(m, 1H), 4.94(t, J=5.0 Hz, 1H), 7.31(dd, J=2.0 Hz, J=8.0 Hz, 1H), 7.40(d, J=2.0 Hz, 1H), 7.49(d, J=8.4 Hz, 1H)

Preparation Example 27

Synthesis of 1-(2,4-dichlorophenyl)-(R,R)-1,2-propanediol

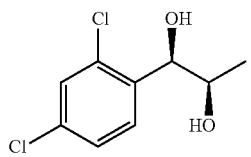

The substantially same method as described in Preparation Example 15 was conducted, except that 1-(2,4-dichlorophenyl)-trans-1-propene (Preparation Example 5) was used instead of 1-(2-chlorophenyl)-trans-1-propene (Preparation Example 1), to obtain the title compound (0.45 g, yield 60~95%).
$^1$H NMR(400 MHz, CDCl$_3$) δ1.22(d, J=6.4 Hz, 3H), 2.10 (d, J=4.4 Hz, 1H), 2.71(d, J=4.8 Hz, 1H), 3.90~3.95(m, 1H), 4.94(t, J=5.0 Hz, 1H), 7.31~7.49(m, 3H)

Preparation Example 28

Synthesis of the mixture of 1-(2,4-dichlorophenyl)-(S,S)-1,2-propanediol and 1-(2,4-dichlorophenyl)-(R,R)-1,2-propanediol

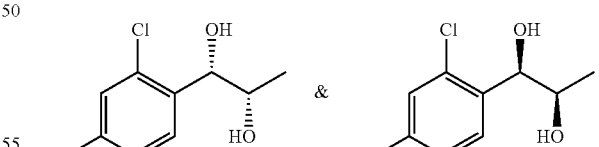

The substantially same method as described in Preparation Example 16 was conducted, except that 1-(2,4-dichlorophenyl)-trans-1-propene (Preparation Example 5) was used instead of 1-(2-chlorophenyl)-trans-1-propene (Preparation Example 1), to obtain the title compound (0.45 g, yield 60~95%).
$^1$H NMR(400 MHz, CDCl$_3$) δ1.22(d, J=6.4 Hz, 3H), 2.10 (d, J=4.4 Hz, 1H), 2.71(d, J=4.8 Hz, 1H), 3.90~3.95(m, 1H), 4.94(t, J=5.0 Hz, 1H), 7.31~7.49(m, 3H)

Preparation Example 29

Synthesis of
1-(2,4-dichlorophenyl)-(S,S)-1,2-butanediol

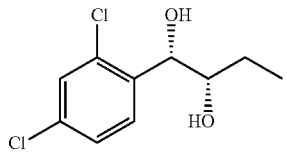

The substantially same method as described in Preparation Example 14 was conducted, except that 1-(2,4-dichlorophenyl)-trans-1-butene (Preparation Example 6) was used instead of 1-(2-chlorophenyl)-trans-1-propene (Preparation Example 1), to obtain the title compound (0.32 g, yield 90%).
$^1$H NMR(400 MHz, CDCl$_3$) δ1.02(t, J=7.4 Hz, 3H), 1.54~1.61(m, 2H), 2.07(d, J=4.8 Hz, 1H), 2.74(d, J=4.8 Hz, 1H), 3.65~3.68(m, 1H), 5.01(t, J=5.0 Hz, 1H), 7.31~7.49(m, 3H)

Preparation Example 30

Synthesis of
1-(2,4-dichlorophenyl)-(R,R)-1,2-butanediol

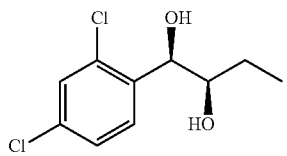

The substantially same method as described in Preparation Example 15 was conducted, except that 1-(2,4-dichlorophenyl)-trans-1-butene (Preparation Example 6) was used instead of 1-(2-chlorophenyl)-trans-1-propene (Preparation Example 1), to obtain the title compound (0.43 g, yield 60~90%).
$^1$H NMR(400 MHz, CDCl$_3$) δ1.02(t, J=7.4 Hz, 3H), 1.54~1.61(m, 2H), 2.07(d, J=4.8 Hz, 1H), 2.74(d, J=4.8 Hz, 1H), 3.65~3.68(m, 1H), 5.01(t, J=5.0 Hz, 1H), 7.31~7.49(m, 3H)

Preparation Example 31

Synthesis of the mixture of 1-(2,4-dichlorophenyl)-(S,S)-1,2-butanediol and 1-(2,4-dichlorophenyl)-(R,R)-1,2-butanediol

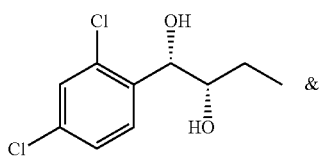

&

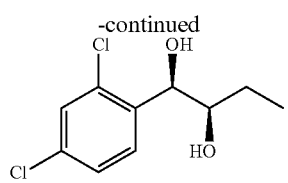

The substantially same method as described in Preparation Example 16 was conducted, except that 1-(2,4-dichlorophenyl)-trans-1-butene (Preparation Example 6) was used instead of 1-(2-chlorophenyl)-trans-1-propene (Preparation Example 1), to obtain the title compound (0.33 g, yield 60~90%).
$^1$H NMR(400 MHz, CDCl$_3$) δ1.02(t, J=7.4 Hz, 3H), 1.54~1.61(m, 2H), 2.07(d, J=4.8 Hz, 1H), 2.74(d, J=4.8 Hz, 1H), 3.65~3.68(m, 1H), 5.01(t, J=5.0 Hz, 1H), 77.31~7.49 (m, 3H)

Preparation Example 32

Synthesis of 1-(2,4-dichlorophenyl)-3-methyl-(S,S)-1,2-butanediol

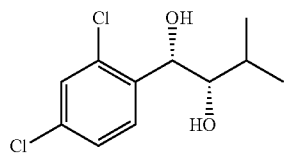

The substantially same method as described in Preparation Example 14 was conducted, except that 1-(2,4-dichlorophenyl)-3-methyl-trans-1-butene (Preparation Example 7) was used instead of 1-(2-chlorophenyl)-trans-1-propene (Preparation Example 1), to obtain the title compound (0.25 g, yield 60~95%).
$^1$H NMR(400 MHz, CDCl$_3$) δ1.00(d, J=6.8 Hz, 6H), 1.60~1.65(m, 1H), 2.35(d, J=4.0 Hz, 1H), 3.12(d, J=8.4 Hz, 1H), 4.13~4.18(m, 1H), 5.36(t, J=7.6 Hz, 1H), 7.17~7.35(m, 3H)

Preparation Example 33

Synthesis of 1-(2,4-dichlorophenyl)-3-methyl-(R,R)-1,2-butanediol

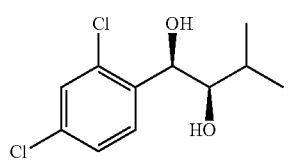

The substantially same method as described in Preparation Example 15 was conducted, except that 1-(2,4-dichlorophenyl)-3-methyl-trans-1-butene (Preparation Example 7) was used instead of 1-(2-chlorophenyl)-trans-1-propene (Preparation Example 1), to obtain the title compound (0.36 g, yield 60~95%).

¹H NMR(400 MHz, CDCl₃) δ1.00(d, J=6.8 Hz, 6H), 1.60~1.65(m, 1H), 2.35(d, J=4.0 Hz, 1H), 3.12(d, J=8.4 Hz, 1H), 4.13~4.18(m, 1H), 5.36(t, J=7.6 Hz, 1H), 7.17~7.35(m, 3H)

Preparation Example 34

Synthesis of the mixture of 1-(2,4-dichlorophenyl)-3-methyl-(S,S)-1,2-butanediol and 1-(2,4-dichlorophenyl)-3-methyl-(R,R)-1,2-butanediol

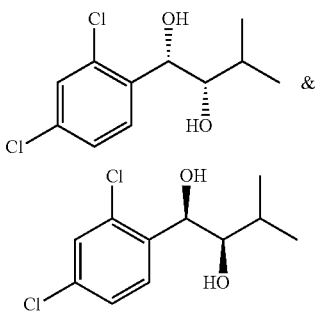

The substantially same method as described in Preparation Example 16 was conducted, except that 1-(2,4-dichlorophenyl)-3-methyl-trans-1-butene (Preparation Example 7) was used instead of 1-(2-chlorophenyl)-trans-1-propene (Preparation Example 1), to obtain the title compound (0.26 g, yield 60~95%).

¹H NMR(400 MHz, CDCl₃) δ1.00(d, J=6.8 Hz, 6H), 1.60~1.65(m, 1H), 2.35(d, J=4.0 Hz, 1H), 3.12(d, J=8.4 Hz, 1H), 4.13~4.18(m, 1H), 5.36(t, J=7.6 Hz, 1H), 7.17~7.35(m, 3H)

Preparation Example 35

Synthesis of 1-(2,4-dichlorophenyl)-(S,S)-1,2-hexanediol

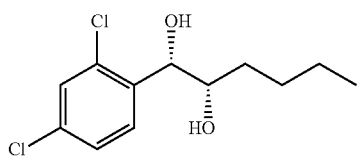 [SMILES: CCCC[C@H](O)[C@@H](O)c1ccc(Cl)cc1Cl]

The substantially same method as described in Preparation Example 14 was conducted, except that 1-(2,4-dichlorophenyl)-trans-1-propene (Preparation Example 8) was used instead of 1-(2-chlorophenyl)-trans-1-propene (Preparation Example 1), to obtain the title compound (1.1 g, yield 60~90%).

¹H NMR(400 MHz, CDCl₃) δ0.89~0.93(m, 3H), 1.30~1.39(m, 2H), 1.49~1.52(m, 2H), 1.56~1.62(m, 2H), 2.05(d, J=5.2 Hz, 1H), 2.74(d, J=5.2 Hz, 1H), 3.72~3.77(m, 1H), 4.98(t, J=4.8 Hz, 1H), 7.28~7.50(m, 3H)

Preparation Example 36

Synthesis of 1-(2,4-dichlorophenyl)-(R,R)-1,2-hexanediol

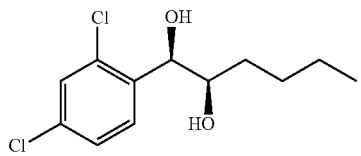 [SMILES: CCCC[C@@H](O)[C@H](O)c1ccc(Cl)cc1Cl]

The substantially same method as described in Preparation Example 15 was conducted, except that 1-(2,4-dichlorophenyl)-trans-1-propene (Preparation Example 8) was used instead of 1-(2-chlorophenyl)-trans-1-propene (Preparation Example 1), to obtain the title compound (1.2 g, yield 60~95%).

¹H NMR(400 MHz, CDCl₃) δ0.89~0.93(m, 3H), 1.30~1.39(m, 2H), 1.49~1.52(m, 2H), 1.56~1.62(m, 2H), 2.05(d, J=5.2 Hz, 1H), 2.74(d, J=5.2 Hz, 1H), 3.72~3.77(m, 1H), 4.98(t, J=4.8 Hz, 1H), 7.28~7.50(m, 3H)

Preparation Example 37

Synthesis of the mixture of 1-(2,4-dichlorophenyl)-(S,S)-1,2-hexanediol and 1-(2,4-dichlorophenyl)-(R,R)-1,2-hexanediol

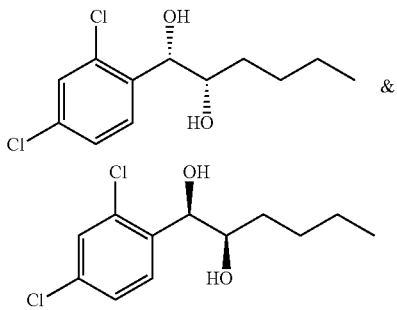

The substantially same method as described in Preparation Example 16 was conducted, except that 1-(2,4-dichlorophenyl)-trans-1-propene (Preparation Example 8) was used instead of 1-(2-chlorophenyl)-trans-1-propene (Preparation Example 1), to obtain the title compound (0.67 g, yield 60~95%).

¹H NMR(400 MHz, CDCl₃) δ0.89~0.93(m, 3H), 1.30~1.39(m, 2H), 1.49~1.52(m, 2H), 1.56~1.62(m, 2H), 2.05(d, J=5.2 Hz, 1H), 2.74(d, J=5.2 Hz, 1H), 3.72~3.77(m, 1H), 4.98(t, J=4.8 Hz, 1H), 7.28~7.50(m, 3H)

Preparation Example 38

Synthesis of
1-(2,6-dichlorophenyl)-(S,S)-1,2-propanediol

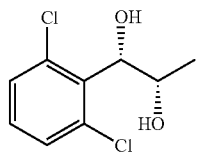

The substantially same method as described in Preparation Example 14 was conducted, except that 1-(2,6-dichlorophenyl)-trans-1-propene (Preparation Example 9) was used instead of 1-(2-chlorophenyl)-trans-1-propene (Preparation Example 1), to obtain the title compound (0.9 g, yield 60~90%).
$^1$H NMR(400 MHz, CDCl$_3$) δ1.10(d, J=6.4 Hz, 3H), 2.72 (d, J=2.4 Hz, 1H), 3.10(d, J=8.4 Hz, 1H), 4.47~4.54(m, 1H), 5.24(t, J=8.8 Hz, 1H), 7.18~7.36(m, 3H)

Preparation Example 39

Synthesis of
1-(2,6-dichlorophenyl)-(R,R)-1,2-propanediol

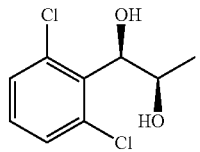

The substantially same method as described in Preparation Example 15 was conducted, except that 1-(2,6-dichlorophenyl)-trans-1-propene (Preparation Example 9) was used instead of 1-(2-chlorophenyl)-trans-1-propene (Preparation Example 1), to obtain the title compound (0.84 g, yield 60~90%).
$^1$H NMR(400 MHz, CDCl$_3$) δ1.10(d, J=6.4 Hz, 3H), 2.72 (d, J=2.4 Hz, 1H), 3.10(d, J=8.4 Hz, 1H), 4.47~4.54(m, 1H), 5.24(t, J=8.8 Hz, 1H), 7.18~7.36(m, 3H)

Preparation Example 40

Synthesis of the mixture of 1-(2,6-dichlorophenyl)-(S,S)-1,2-propanediol and 1-(2,6-dichlorophenyl)-(R,R)-1,2-propanediol

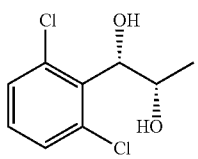 & 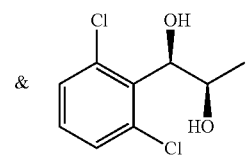

The substantially same method as described in Preparation Example 16 was conducted, except that 1-(2,6-dichlorophenyl)-trans-1-propene (Preparation Example 9) was used instead of 1-(2-chlorophenyl)-trans-1-propene (Preparation Example 1), to obtain the title compound (0.91 g, yield 60~90%).
$^1$H NMR(400 MHz, CDCl$_3$) δ1.10(d, J=6.4 Hz, 3H), 2.72 (d, J=2.4 Hz, 1H), 3.10(d, J=8.4 Hz, 1H), 4.47~4.54(m, 1H), 5.24(t, J=8.8 Hz, 1H), 7.18~7.36(m, 3H)

Preparation Example 41

Synthesis of
1-(2,6-dichlorophenyl)-(S,S)-1,2-butanediol

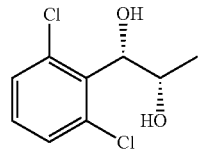

The substantially same method as described in Preparation Example 14 was conducted, except that 1-(2,6-dichlorophenyl)-trans-1-butene (Preparation Example 10) was used instead of 1-(2-chlorophenyl)-trans-1-propene (Preparation Example 1), to obtain the title compound (1.23 g, yield 60~95%).
$^1$H NMR(400 MHz, CDCl$_3$) δ0.97(t, J=7.6 Hz, 3H), 1.26~1.53(m, 2H), 2.64(dd, J=0.8 Hz, J=4.0 Hz, 1H), 3.14(d, J=8.4 Hz, 1H), 4.22~4.26(m, 1H), 5.26(t, J=8.4 Hz, 1H), 7.17~7.35(m, 3H)

Preparation Example 42

Synthesis of
1-(2,6-dichlorophenyl)-(R,R)-1,2-butanediol

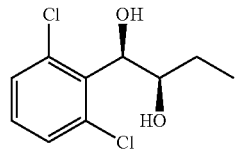

The substantially same method as described in Preparation Example 15 was conducted, except that 1-(2,6-dichlorophenyl)-trans-1-butene (Preparation Example 10) was used instead of 1-(2-chlorophenyl)-trans-1-propene (Preparation Example 1), to obtain the title compound (0.96 g, yield 60~95%).
$^1$H NMR(400 MHz, CDCl$_3$) δ0.97(t, J=7.6 Hz, 3H), 1.26~1.53(m, 2H), 2.64(dd, J=0.8 Hz, J=4.0 Hz, 1H), 3.14(d, J=8.4 Hz, 1H), 4.22~4.26(m, 1H), 5.26(t, J=8.4 Hz, 1H), 7.17~7.35(m, 3H)

Preparation Example 43

Synthesis of the mixture of 1-(2,6-dichlorophenyl)-(S,S)-1,2-butanediol and 1-(2,6-dichlorophenyl)-(R,R)-1,2-butanediol

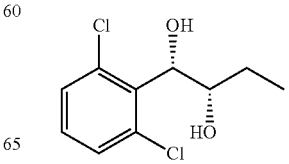 & 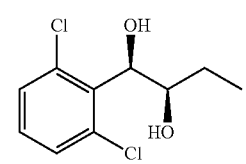

The substantially same method as described in Preparation Example 16 was conducted, except that 1-(2,6-dichlorophenyl)-trans-1-butene (Preparation Example 10) was used instead of 1-(2-chlorophenyl)-trans-1-propene (Preparation Example 1), to obtain the title compound (0.86 g, yield 60~95%).

$^1$H NMR(400 MHz, CDCl$_3$) δ0.97(t, J=7.6 Hz, 3H), 1.26~1.53(m, 2H), 2.64(dd, J=0.8 Hz, J=4.0 Hz, 1H), 3.14(d, J=8.4 Hz, 1H), 4.22~4.26(m, 1H), 5.26(t, J=8.4 Hz, 1H), 7.17~7.35(m, 3H)

Preparation Example 44

Synthesis of 1-(2,6-dichlorophenyl)-3-methyl-(S,S)-1,2-butanediol

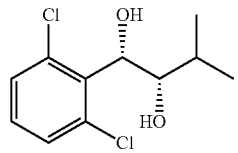

The substantially same method as described in Preparation Example 14 was conducted, except that 1-(2,6-dichlorophenyl)-3-methyl-trans-1-butene (Preparation Example 11) was used instead of 1-(2-chlorophenyl)-trans-1-propene (Preparation Example 1), to obtain the title compound (0.25 g, yield 60~95%).

$^1$H NMR(400 MHz, CDCl$_3$) δ1.00(d, J=6.8 Hz, 6H), 1.60~1.65(m, 1H), 2.35(d, J=4.0 Hz, 1H), 3.12(d, J=8.4 Hz, 1H), 4.13~4.18(m, 1H), 5.36(t, J=7.6 Hz, 1H), 7.17~7.35(m, 3H)

Preparation Example 45

Synthesis of 1-(2,6-dichlorophenyl)-3-methyl-(R,R)-1,2-butanediol

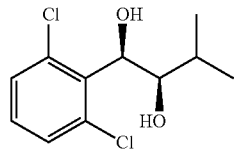

The substantially same method as described in Preparation Example 15 was conducted, except that 1-(2,6-dichlorophenyl)-3-methyl-trans-1-butene (Preparation Example 11) was used instead of 1-(2-chlorophenyl)-trans-1-propene (Preparation Example 1), to obtain the title compound (0.37 g, yield 60~95%).

$^1$H NMR(400 MHz, CDCl$_3$) δ1.00(d, J=6.8 Hz, 6H), 1.60~1.65(m, 1H), 2.35(d, J=4.0 Hz, 1H), 3.12(d, J=8.4 Hz, 1H), 4.13~4.18(m, 1H), 5.36(t, J=7.6 Hz, 1H), 7.17~7.35(m, 3H)

Preparation Example 46

Synthesis of the mixture of 1-(2,6-dichlorophenyl)-3-methyl-(S,S)-1,2-butanediol and 1-(2,6-dichlorophenyl)-3-methyl-(R,R)-1,2-butanediol

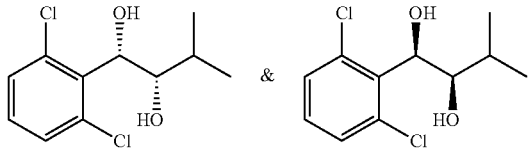

The substantially same method as described in Preparation Example 16 was conducted, except that 1-(2,6-dichlorophenyl)-3-methyl-trans-1-butene (Preparation Example 11) was used instead of 1-(2-chlorophenyl)-trans-1-propene (Preparation Example 1), to obtain the title compound (0.47 g, yield 60~95%).

$^1$H NMR(400 MHz, CDCl$_3$) δ1.00(d, J=6.8 Hz, 6H), 1.60~1.65(m, 1H), 2.35(d, J=4.0 Hz, 1H), 3.12(d, J=8.4 Hz, 1H), 4.13~4.18(m, 1H), 5.36(t, J=7.6 Hz, 1H), 7.17~7.35(m, 3H)

Preparation Example 47

Synthesis of 1-(2,6-dichlorophenyl)-(S,S)-1,2-hexanediol

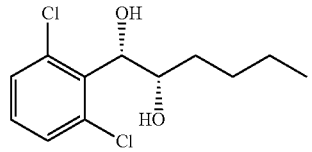 [SMILES: CCCC[C@H](O)[C@@H](O)c1c(Cl)cccc1Cl]

The substantially same method as described in Preparation Example 14 was conducted, except that 1-(2,6-dichlorophenyl)-trans-1-hexene (Preparation Example 12) was used instead of 1-(2-chlorophenyl)-trans-1-propene (Preparation Example 1), to obtain the title compound (0.36 g, yield 60~90%).

$^1$H NMR(400 MHz, CDCl$_3$) δ0.85(t, J=6.8 Hz, 3H), 1.20~1.31(m, 4H), 1.45~1.53(m, 2H), 2.61~2.62(m, 1H), 3.12(d, J=8.4 Hz, 1H), 4.28~4.33(m, 1H), 5.25(t, J=8.4 Hz, 1H), 7.18~7.35(m, 3H)

Preparation Example 48

Synthesis of 1-(2,6-dichlorophenyl)-(R,R)-1,2-hexanediol

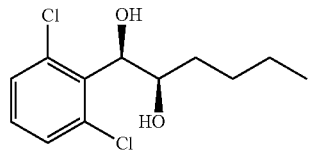

The substantially same method as described in Preparation Example 15 was conducted, except that 1-(2,6-dichlorophenyl)-trans-1-hexene (Preparation Example 12) was used instead of 1-(2-chlorophenyl)-trans-1-propene (Preparation Example 1), to obtain the title compound (0.58 g, yield 60~90%).

$^1$H NMR(400 MHz, CDCl$_3$) δ0.85(t, J=6.8 Hz, 3H), 1.20~1.31(m, 4H), 1.45~1.53(m, 2H), 2.61~2.62(m, 1H), 3.12(d, J=8.4 Hz, 1H), 4.28~4.33(m, 1H), 5.25(t, J=8.4 Hz, 1H), 7.18~7.35(m, 3H)

Preparation Example 49

Synthesis of the mixture of 1-(2,6-dichlorophenyl)-(S,S)-1,2-hexanediol and 1-(2,6-dichlorophenyl)-(R,R)-1,2-hexanediol

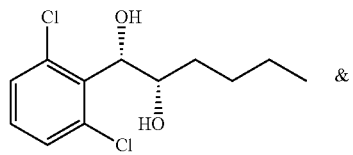

&

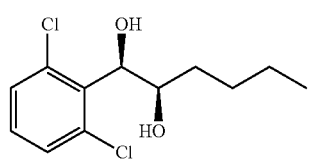 [SMILES: CCCC[C@@H](O)[C@H](O)c1c(Cl)cccc1Cl]

The substantially same method as described in Preparation Example 16 was conducted, except that 1-(2,6-dichlorophenyl)-trans-1-hexene (Preparation Example 12) was used instead of 1-(2-chlorophenyl)-trans-1-propene (Preparation Example 1), to obtain the title compound (0.62 g, yield 60~90%).

$^1$H NMR(400 MHz, CDCl$_3$) δ0.85(t, J=6.8 Hz, 3H), 1.20~1.31(m, 4H), 1.45~1.53(m, 2H), 2.61~2.62(m, 1H), 3.12(d, J=8.4 Hz, 1H), 4.28~4.33(m, 1H), 5.25(t, J=8.4 Hz, 1H), 7.18~7.35(m, 3H)

Preparation Example 50

Synthesis of methyl 2-(2-chlorophenyl)-(R)-2-hydroxyacetate

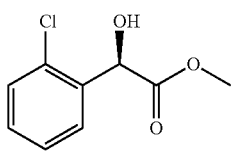

15 g of (R)-2-chloromandelic acid was mixed with methanol (CH$_3$OH, 150 ml) and phosphorus chloride oxide (POCl$_3$, 0.76 ml) in a flask by stirring using a magnetic stirrer at the room temperature for 6 hours. When the reaction was completed, the obtained product was washed with an aqueous solution of sodium sulfite (Na$_2$SO$_3$) and ethylacetate (EA). Then, the organic layer was dehydrated with anhydrous magnesium sulfate (MgSO$_4$), filtrated, and concented under reduced pressure. The concentrated residue was purified by a silica gel column chromatography to produce the title compound (15.64 g, yield 95%).

$^1$H NMR(400 MHz, CDCl$_3$) δ 3.59(d, J=5.2, 1H), 3.79(t, J=6.0, 3H), 5.59(d, J=5.2, 1H), 7.28~7.43(m, 4H)

Preparation Example 51

Synthesis of 2-(2-chlorophenyl)-(R)-2-hydroxy-N-methoxy-N-methylacetamide

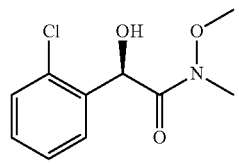

N,O-dimethylhydroxylamine hydrochloride (N,O-dimethylhydroxylamine.HCl, 15.2 g) was dissolved in dichloromethane (DCM, 150 ml), and cooled to 0° C. using an ice-bath. Then, 77.7 ml of 2.0M trimethylaluminium in hexane was slowly added thereto in drop-wise manner for 30 minutes. Thereafter, the ice-bath was removed, and the obtained product was stirred at the room temperature for 2 hours. Methyl-2-(2-chlorophenyl)-(R)-2-hydroxyacetate (15.64 g) dissolved in dichloromethane (DCM, 150 ml) was added in drop-wise manner thereto at the room temperature for 30 minutes, and subjected to reflux for 12 hours. When the reaction was completed, the obtained product was cooled to 0° C., and washed by a slow drop-wise addition of hydrochloric acid (HCl, 200 ml). The obtained organic layer was washed with distilled water and brine, dehydrated with anhydrous magnesium sulfate (MgSO$_4$), filtrated, and concented under reduced pressure. The concentrated residue was purified by a silica gel column chromatography to produce the title compound (14.68 g, yield 82%).

$^1$H NMR(400 MHz, CDCl$_3$) δ3.23(s, 3H), 3.28(s, 3H), 4.33(d, J=6.0 Hz, 1H), 5.81(d, J=5.6 Hz, 1H), 7.23~7.42(m, 4H)

Preparation Example 52

Synthesis of 2-(2-chlorophenyl)-N-methoxy-(R)-2-(methoxymethoxy)-N-methylacetamide

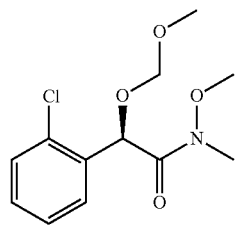 [SMILES: COCO[C@@H](C(=O)N(C)OC)c1ccccc1Cl]

2-(2-chlorophenyl)-(R)-2-hydroxy-N-methoxy-N-methylacetamide (14.68 g) obtained in Preparation Example 51 was dissolved in dichloromethane (DCM, 140 ml), and cooled to 0° C. Diisopropylethylamine (55.67 ml) was slowly added thereto in drop-wise manner, and stirred for 10 minutes. Chloro methyl methyl ether (25.25 ml) was slowly added thereto in drop-wise manner for 30 minutes. After 30 minutes, the ice-bath was removed and the obtained product was stirred for 30 at room temperature. When the reaction was completed, the obtained product was cooled to 0° C. And then, to the obtained product, 1M sodium hydroxide solution (1M NaOH, 20 ml) was added in drop-wise manner, and dichloromethane (DMC) was injected. Then the obtained product was washed with water. The obtained organic layer was dehydrated with anhydrous magnesium sulfate (MgSO$_4$), filtrated, and concented under reduced pressure. The concentrated residue was purified by a silica gel column chromatography to produce the title compound (15.57 g, yield 89%).

$^1$H NMR(400 MHz, CDCl$_3$) δ3.19(s, 3H), 3.42(s, 3H), 3.47(s, 3H), 4.75(d, J=6.8, 1H), 4.81(d, J=6.8, 1H), 6.07(s, 1H), 7.27~7.58(m, 4H)

Preparation Example 53

Synthesis of 1-(2-chlorophenyl)-(R)-1-(methoxymethoxy)propane-2-on

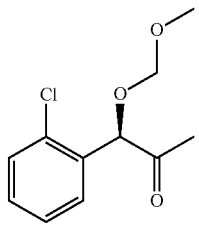

2-(2-chlorophenyl)-N-methoxy-(R)-2-(methoxymethoxy)-N-methylacetamide (15.57 g) obtained in Preparation Example 52 was dissolved in tetrahydrofuran (THF, 150 ml), and cooled to 0° C. 3.0M methyl magnesium bromide (MeMgBr) solution in ether was added thereto in drop-wise manner for 30 minutes, and the obtained product was stirred for 1 hour at 0° C. When the reaction was completed, diethylether (100 ml) was added thereto. The obtained product was washed with 10% (w/v) potassium hydrogen sulfate (KHSO$_4$, 100 ml) and then, washed again with brine. The obtained organic layer was dehydrated with anhydrous magnesium sulfate (MgSO$_4$), filtrated, and concented under reduced pressure. The concentrated residue was purified by a silica gel column chromatography to produce the title compound (11.83 g, yield 90%).

$^1$H NMR(400 MHz, CDCl$_3$) δ2.18(s, 3H), 3.39(s, 3H), 4.65(d, J=6.8, 1H), 4.74(d, J=6.8, 1H), 5.63(s, 1H), 7.30~7.45 (m, 4H)

Preparation Example 54

Synthesis of 1-(2-chlorophenyl)-(R)-1-(methoxymethoxy)-(S)-2-propanol

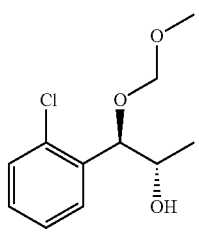

1-(2-chlorophenyl)-(R)-1-(methoxymethoxy)propane-2-on (11.83 g) obtained in Preparation Example 53 was dissolved in toluene (110 ml), and cooled to −40° C. Sodium bis(2-methoxyethoxy)aluminumhydride solution (15.7 ml) in toluene was slowly added thereto for 30 minutes, and then, the obtained product was stirred for 1 hour. When the reaction was completed, the obtained product was washed by slow drop-wise addition of sodium potassium tartrate (100 ml). The obtained organic layer was dehydrated with anhydrous magnesium sulfate (MgSO$_4$), filtrated, and concented under reduced pressure. The concentrated residue was purified by a silica gel column chromatography to produce the title compound (10.38 g, yield 87%).

$^1$H NMR(400 MHz, CDCl$_3$) δ1.13(d, J=6.4, 3H), 2.33(d, J=7.2, 1H), 3.44(s, 3H), 4.10~4.18(m, 1H), 4.61(d, J=6.4, 1H), 4.69(d, J=6.8, 1 H), 5.14(d, J=3.6, 1 H), 7.22~7.55(m, 4H)

Preparation Example 55

Synthesis of 1-(2-chlorophenyl)-(R,S)-1,2-propanediol

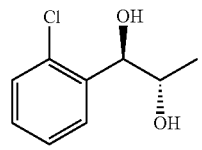

1-(2-chlorophenyl)-(R)-1-(methoxymethoxy)-(S)-2-propanol (10.38 g) obtained in Preparation Example 54 was dissolved in methanol (CH$_3$OH, 100 ml), and then, cooled to 0° C. 8M hydrochloric acid (HCl, 56.2 ml) was slowly added in drop-wise manner to the obtained product, and then, the obtained product was warmed to the room temperature, and stirred for 15 hours. When the reaction was completed, the obtained product was cooled to 0° C. 5N sodium hydroxide (NaOH, 30 ml) was slowly added thereto, and the obtained product was subjected to vacuum concentration. The obtained product was diluted with ethylacetate. The obtained organic layer was washed with distilled water, dehydrated with anhydrous magnesium sulfate (MgSO$_4$), filtrated, and concented under reduced pressure. The concentrated residue was purified by a silica gel column chromatography to produce the title compound (7.05 g, yield 60~90%).

$^1$H NMR(400 MHz, CDCl$_3$) δ1.07(d, J=6.8, 3H), 2.01(d, J=5.6, 1H), 2.61(s, 1H), 4.21~4.27(m, 1H), 5.24(d, J=3.6, 1H), 7.22~7.64(m, 4H)

Preparation Example 56

Synthesis of 1-(2-chlorophenyl)-(S,R)-1,2-propanediol

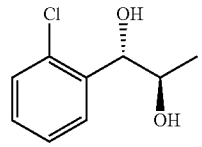

The substantially same method as described in Preparation Example 50~55 was conducted, except that (S)-2-chloromandelic acid was used instead of (R)-2-chloromandelic acid, to obtain the title compound (5.04 g, yield 84%).

¹H NMR(400 MHz, CDCl₃) δ1.07(d, J=6.8, 3H), 2.00(d, J=5.6, 1H), 2.54(d, J=3.6, 1H), 4.22~4.26(m, 1H), 5.25(t, J=3.2, 1H), 7.22~7.65(m, 4H)

Preparation Example 57

Synthesis of 1-(2,3-dichlorophenyl)-(S,S)-1,2-propanediol

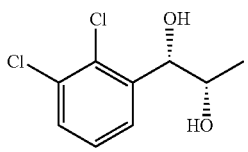

The substantially same method as described in Preparation Example 14 was conducted, except that 1-(2,3-dichlorophenyl)-trans-1-propene (Preparation Example 13) was used instead of 1-(2-chlorophenyl)-trans-1-propene (Preparation Example 1), to obtain the title compound (0.9 g, yield 60~90%).

¹H NMR(400 MHz, CDCl₃) δ1.10(d, J=6.4 Hz, 3H), 2.72 (d, J=2.4 Hz, 1H), 3.10(d, J=8.4 Hz, 1H), 4.47~4.54(m, 1H), 5.24(t, J=8.8 Hz, 1H), 7.18~(m, 3H)

Preparation Example 58

Synthesis of 1-(2,3-dichlorophenyl)-(R,R)-1,2-propanediol

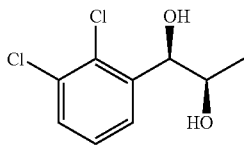

The substantially same method as described in Preparation Example 15 was conducted, except that 1-(2,3-dichlorophenyl)-trans-1-propene (Preparation Example 13) was used instead of 1-(2-chlorophenyl)-trans-1-propene (Preparation Example 1), to obtain the title compound (0.84 g, yield 60~90%).

¹H NMR(400 MHz, CDCl₃) δ1.10(d, J=6.4 Hz, 3H), 2.72 (d, J=2.4 Hz, 1H), 3.10(d, J=8.4 Hz, 1H), 4.47~4.54(m, 1H), 5.24(t, J=8.8 Hz, 1H), 7.18~(m, 3H)

Preparation Example 59

Synthesis of the mixture of 1-(2,3-dichlorophenyl)-(S,S)-1,2-propanediol and 1-(2,3-dichlorophenyl)-(R,R)-1,2-propanediol

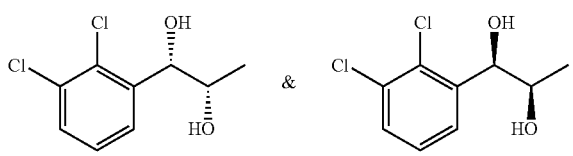

The substantially same method as described in Preparation Example 16 was conducted, except that 1-(2,3-dichlorophenyl)-trans-1-propene (Preparation Example 13) was used instead of 1-(2-chlorophenyl)-trans-1-propene (Preparation Example 1), to obtain the title compound (0.91 g, yield 60~90%).

¹H NMR(400 MHz, CDCl₃) δ 1.10(d, J=6.4 Hz, 3H), 2.72 (d, J=2.4 Hz, 1H), 3.10(d, J=8.4 Hz, 1H), 4.47~4.54(m, 1H), J=8.8 Hz, 1H), 7.18~(m, 3H)

Preparation Example 60

Synthesis of 1-(2-fluorophenyl)-trans-1-propene

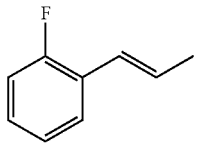

The substantially same method as described in Preparation Example 1 was conducted, except that 2-fluorobenzenaldehyde was used instead of 2-chlorobenzenealdehyde, to obtain the title compound (6.67 g, yield 61%).

¹H NMR(400 MHz, CDCl₃) δ1.94(d, J=6.8 Hz, 3H), 6.30~6.38(m, 1H), 6.57(d, J=16 Hz, 1H), 7.00~7.41(m, 4H)

Preparation Example 61

Synthesis of 1-(2-fluorophenyl)-(S,S)-1,2-propanediol

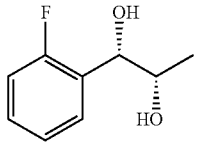

The substantially same method as described in Preparation Example 14 was conducted, except that 1-(2-fluorophenyl)-trans-1-propene (Preparation Example 60) was used instead of 1-(2-chlorophenyl)-trans-1-propene (Preparation Example 1), to obtain the title compound (6.46 g, yield 78%).

¹H NMR(400 MHz, CDCl₃) δ1.15(d, J=6.4 Hz, 3H), 2.43 (d, J=3.6 Hz, 1H), 2.69(d, J=4.8 Hz, 1H), 3.90~3.98(m, 1H), 4.78(dd, J=4.4, 7.2 Hz, 1H), 7.04~7.50(m, 4H)

Preparation Example 62

Synthesis of 1-(2-fluorophenyl)-(R,R)-1,2-propanediol

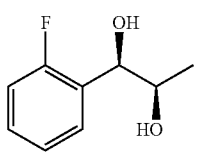

The substantially same method as described in Preparation Example 15 was conducted, except that 1-(2-fluorophenyl)-trans-1-propene (Preparation Example 60) was used instead of 1-(2-chlorophenyl)-trans-1-propene (Preparation Example 1), to obtain the title compound (3.29 g, yield 79%).

¹H NMR(400 MHz, CDCl₃) δ1.15(d, J=6.4 Hz, 3H), 2.43 (d, J=3.6 Hz, 1H), 2.69(d, J=4.8 Hz, 1H), 3.90~3.98(m, 1H), 4.78(dd, J=4.4, 7.2 Hz, 1H), 7.04~7.50(m, 4H)

Preparation Example 63

Synthesis of 2-iodobenzenealdehyde

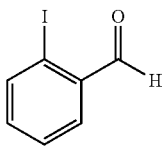

In a flask, 2-iodobenzyl alcohol (4 g, 17.09 mmol) was dissolved in dichloromethane (MC, 85 ml), and then, manganese oxide ($MnO_2$, 14.86 g, 170.92 mmol) was added thereto. The obtained reaction product was stirred under the reflux condition. When the reaction was completed, the obtained reaction product was cooled to the room temperature, and then, fiteated and concentrated using celite, to obtain the title compound (3.6 g, yield 91%).

$^1$H NMR(400 MHz, $CDCl_3$) δ7.30~7.99(m, 4H), 10.10(s, 1H)

Preparation Example 64

Synthesis of 1-(2-iodophenyl)-trans-1-propene

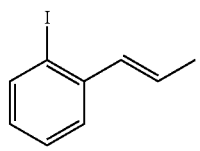

The substantially same method as described in Preparation Example 1 was conducted, except that 2-iodobenzenealdehyde (Preparation Example 63) was used instead of 2-chlorobenzenealdehyde, to obtain the title compound (3.4 g, yield 65%).

$^1$H NMR(400 MHz, $CDCl_3$) δ1.95(dd, J=6.8 Hz, 1.6 Hz, 3H), 6.09~6.18(m, 1H), 6.60(dd, J=15.66 Hz, 1.8 Hz, 1H), 6.89~7.84(m, 4H)

Preparation Example 65

Synthesis of 1-(2-iodophenyl)-trans-1-butene

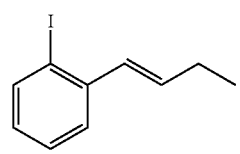

The substantially same method as described in Preparation Example 64 was conducted, except that 3-heptanone was used instead of 3-pentanone, to obtain the title compound (8.5 g, yield 75%).

$^1$H NMR(400 MHz, $CDCl_3$) δ1.46(t, J=7.6 Hz, 3H), 2.26~2.34(m, 2H), 6.17(dt, J=15.6 Hz, 6.6 Hz 1H), 6.57(d, J=15.6 Hz, 1H), 6.89~7.85(m, 4H)

Preparation Example 66

Synthesis of 1-(2-iodophenyl)-(S,S)-1,2-propanediol

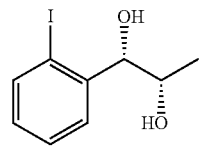

The substantially same method as described in Preparation Example 14 was conducted, except that 1-(2-iodophenyl)-trans-1-propene (Preparation Example 64) was used instead of 1-(2-chlorophenyl)-trans-1-propene (Preparation Example 1), to obtain the title compound (3.4 g, yield 88%).

$^1$H NMR(400 MHz, $CDCl_3$) δ1.27(d, J=6.4 Hz, 3H), 2.26 (br s, 1H), 2.74(br s, 1H), 3.99(t, J=6.0 Hz, 1H), 4.81(d, J=4.0 Hz, 1H), 7.01~7.87(m, 4H)

Preparation Example 67

Synthesis of 1-(2-iodorophenyl)-(R,R)-1,2-propanediol

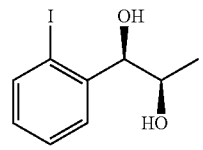

The substantially same method as described in Preparation Example 15 was conducted was conducted, except that 1-(2-iodophenyl)-trans-1-propene (Preparation Example 64) was used instead of 1-(2-chlorophenyl)-trans-1-propene (Preparation Example 1), to obtain the title compound (7.4 g, yield 84%).

$^1$H NMR(400 MHz, $CDCl_3$) δ1.26(d, J=6.4 Hz, 3H), 2.35 (br s, 1H), 2.85(br d, J=4.0 Hz, 1H), 3.98(t, J=6.2 Hz, 1H), 4.80(dd, J=5.0, 4.4 Hz, 1H), 7.00~7.87(m, 4H)

Preparation Example 68

Synthesis of 1-(2-iodophenyl)-(S,S)-1,2-butanediol

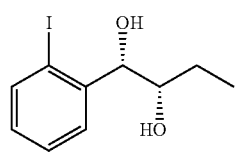

The substantially same method as described in Preparation Example 14 was conducted was conducted, except that 1-(2-iodophenyl)-trans-1-butene (Preparation Example 65) was used instead of 1-(2-chlorophenyl)-trans-1-propene (Preparation Example 1), to obtain the title compound (9.5 g, yield 84%).

¹H NMR(400 MHz, CDCl₃) δ1.04(t, J=7.6 Hz, 3H), 1.60~1.71(m, 2H), 2.07(br s, 1H), 2.74(br s, 1H), 3.71~3.76 (m, 1H), 4.87(d, J=4.8 Hz, 1H), 7.01~7.87(m, 4H)

Example 1

Synthesis of 1-(2-chlorophenyl)-(S)-1-hydroxypropyl-(S)-2-carbamate (1)

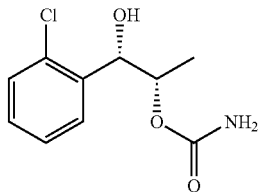

1-(2-chlorophenyl)-(S,S)-1,2-propanediol (2.33 g) obtained in Preparation Example 14, tetrahydrofuran (THF, 12 ml), and carbonyldiimidazole (CDI, 3.04 g) were put into a flask and stirred at the room temperature. After approximately 3 hours, ammonia solution (NH₄OH, 4 ml) was added thereto. When the reaction was completed, the obtained product was washed with 1M HCl solution and ethylacetate (EA). The separated organic layer was dehydrated with anhydrous magnesium sulfate (MgSO₄), filtrated, and concented under reduced pressure. The concentrated residue was purified by a silica gel column chromatography, to obtain the title compound (1.40 g, yield 49%).

M.P. 83~84° C.

¹H NMR(400 MHz, CDCl₃) δ1.24(d, J=6.4 Hz, 3H), 2.91 (d, J=4.8 Hz, 1H), 4.68(br s, 2H), 5.06~5.09(m, 1H), 5.18~5.21(m, 1H), 7.23~7.55(m, 4H)

¹³C NMR (100 MHz, CDCl₃) δ16.4, 73.1, 75.0, 127.0, 128.4, 129.1, 129.5, 132.7, 138.0, 156.6

Example 2

Synthesis of 1-(2-chlorophenyl)-(R)-1-hydroxypropyl-(R)-2-carbamate (2)

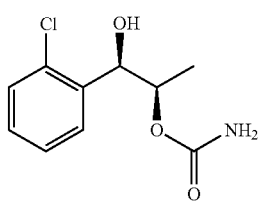

The substantially same method as described in Example 1 was conducted, except that 1-(2-chlorophenyl)-(R,R)-1,2-propanediol obtained in Preparation Example 15 was used instead of 1-(2-chlorophenyl)-(S,S)-1,2-propanediol, to obtain the title compound (1.74 g, yield 50%).

M.P. 85~86° C.

¹H NMR(400 MHz, CDCl₃) δ1.24(d, J=6.4 Hz, 3H), 2.98 (d, J=4.0 Hz, 1H), 4.73(br s, 2H), 5.04~5.10(m, 1H), 5.18~5.20(m, 1H), 7.24~7.55(m, 4H)

Example 3

Synthesis of 1-(2-chlorophenyl)-1-hydroxypropyl-2-carbamate (3)

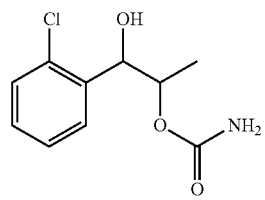

The substantially same method as described in Example 1 was conducted, except that the mixture of 1-(2-chlorophenyl)-(S,S)-1,2-propanediol and 1-(2-chlorophenyl)-(R,R)-1,2-propanediol obtained in Preparation Example 16 was used instead of 1-(2-chlorophenyl)-(S,S)-1,2-propanediol, to obtain the title compound (0.41 g, yield 38%).

¹H NMR(400 MHz, CDCl₃) δ1.14(d, J=6.8 Hz, 3H), 3.34 (d, J=3.2 Hz, 1H), 5.06(brs, 2H), 5.09~5.15(m, 1H), 5.31(br t, J=2.4 Hz, 1H), 7.18~7.59(m, 4H)

Example 4

Synthesis of 1-(2-chlorophenyl)-(R)-1-hydroxypropyl-(S)-2-carbamate (4)

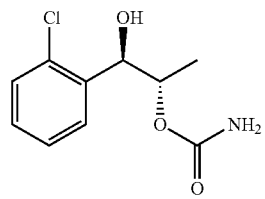

The substantially same method as described in Example 1 was conducted, except that 1-(2-chlorophenyl)-(R,S)-1,2-propanediol obtained in Preparation Example 55 was used instead of 1-(2-chlorophenyl)-(S,S)-1,2-propanediol, to obtain the title compound (1.7 g, yield 50%).

¹H NMR(400 MHz, CDCl₃) δ1.20(d, J=6.8, 3H), 2.68(s, 1H), 4.67(s, 2H), 5.16~5.22(m, 1H), 5.36(t, J=3.2, 1H), 7.23~7.61(m, 4H)

Example 5

Synthesis of 1-(2-chlorophenyl)-(S)-1-hydroxypropyl-(R)-2-carbamate (5)

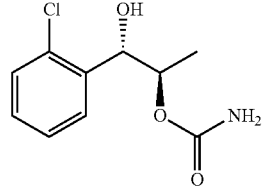

The substantially same method as described in Example 1 was conducted, except that 1-(2-chlorophenyl)-(S,R)-1,2-propanediol obtained in Preparation Example 56 was used instead of 1-(2-chlorophenyl)-(S,S)-1,2-propanediol, to obtain the title compound (1.74 g, yield 50%).

$^1$H NMR(400 MHz, CDCl$_3$) δ1.20(d, J=6.4, 3H), 2.83(d, J=3.6, 1H), 4.78(s, 2H), 5.15~5.21(m, 1H), 5.36(t, J=3.2, 1H), 7.23~7.63(m, 4H)

Example 6

Synthesis of 1-(2-chlorophenyl)-(S)-1-hydroxybutyl-(S)-2-carbamate (6)

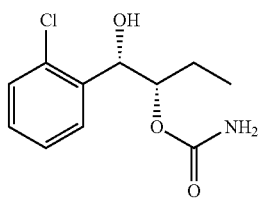 [SMILES: CC[C@H](OC(N)=O)[C@@H](O)c1ccccc1Cl]

The substantially same method as described in Example 1 was conducted, except that 1-(2-chlorophenyl)-(S,S)-1,2-butanediol obtained in Preparation Example 17 was used instead of 1-(2-chlorophenyl)-(S,S)-1,2-propanediol, to obtain the title compound (1.0 g, yield 45%).

$^1$H NMR(400 MHz, CDCl$_3$) δ0.96(t, J=7.4 Hz, 3H), 1.57~1.73(m, 2H), 3.01(d, J=5.6 Hz, 1H), 4.74(br s, 2H), 4.95(dt, J=7.2, 8.8 Hz, 1H), 5.23(t, J=5.6 Hz, 1H), 7.22~7.54 (m, 4H)

Example 7

Synthesis of 1-(2-chlorophenyl)-(R)-1-hydroxybtyl-(R)-2-carbamate (7)

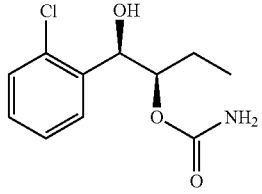 [SMILES: CC[C@@H](OC(N)=O)[C@H](O)c1ccccc1Cl]

The substantially same method as described in Example 1 was conducted, except that 1-(2-chlorophenyl)-(R,R)-1,2-butanediol obtained in Preparation Example 18 was used instead of 1-(2-chlorophenyl)-(S,S)-1,2-propanediol, to obtain the title compound (1.5 g, yield 25%).

$^1$H NMR(400 MHz, CDCl$_3$) δ 0.94(t, J=7.4 Hz, 3H), 1.53~1.73(m, 2H), 2.92(s, 1H), 4.78(br s, 2H), 4.91~4.96(m, 1H), 5.22(d, J=5.5 Hz, 1H), 7.20~7.54(m, 4H)

Example 8

Synthesis of 1-(2-chlorophenyl)-1-hydroxybutyl-2-carbamate (8)

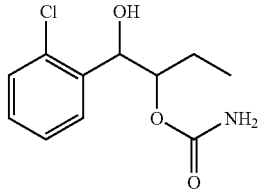 [SMILES: CCC(OC(N)=O)C(O)c1ccccc1Cl]

The substantially same method as described in Example 1 was conducted, except that 1-(2-chlorophenyl)-1,2-butanediol obtained in Preparation Example 19 was used instead of 1-(2-chlorophenyl)-(S,S)-1,2-propanediol, to obtain the title compound (1.8 g, yield 30%).

$^1$H NMR(400 MHz, CDCl$_3$) δ 0.97(t, J=7 Hz, 3H), 1.58~1.74(m, 2H), 2.94(d, J=6 Hz, 1H), 4.69(br s, 2H), 4.94~4.99(m, 1H), 5.24(t, J=6 Hz, 1H), 7.23~7.56(m, 4H)

Example 9

Synthesis of 1-(2-chlorophenyl)-(S)-1-hydroxy-3-methyl-butyl-(S)-2-carbamate (9)

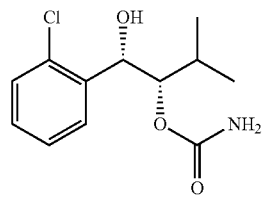 [SMILES: CC(C)[C@H](OC(N)=O)[C@@H](O)c1ccccc1Cl]

The substantially same method as described in Example 1 was conducted, except that 1-(2-chlorophenyl)-3-methyl-(S,S)-1,2-butanediol obtained in Preparation Example 20 was used instead of 1-(2-chlorophenyl)-(S,S)-1,2-propanediol, to obtain the title compound (0.72 g, yield 48%).

$^1$H NMR(400 MHz, CDCl$_3$) δ1.01(d, J=6.4 Hz, 3H), 1.09 (d, J=6.8 Hz, 3H), 2.06(m, 1H), 2.75(d, J=6.8 Hz, 1H), 4.58 (br s, 2H), 4.85~4.88(m, 1H), 5.34~5.37(m, 1H), 7.22~7.33 (m, 2H), 7.35~7.37(m, 1H), 7.51~7.53(m, 1H)

Example 10

Synthesis of 1-(2-chlorophenyl)-(R)-1-hydroxy-3-methyl-butyl-(R)-2-carbamate (10)

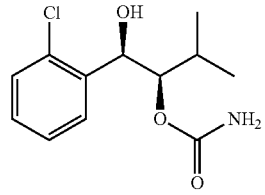 [SMILES: CC(C)[C@@H](OC(N)=O)[C@H](O)c1ccccc1Cl]

The substantially same method as described in Example 1 was conducted, except that 1-(2-chlorophenyl)-3-methyl-(R,R)-1,2-butanediol obtained in Preparation Example 21 was used instead of 1-(2-chlorophenyl)-(S,S)-1,2-propanediol, to obtain the title compound (0.56 g, yield 43%).

$^1$H NMR(400 MHz, CDCl$_3$) δ1.01(d, J=6.8 Hz, 3H), 1.09 (d, J=6.8 Hz, 3H), 2.06(m, 1H), 2.73(d, J=6.8 Hz, 1H), 4.57 (br s, 2H), 4.85~4.88(m, 1H), 5.34~5.37(m, 1H), 7.24~7.30 (m, 2H), 7.35~7.37(m, 1H), 7.51~7.53(m, 1H)

Example 11

Synthesis of 1-(2-chlorophenyl)-1-hydroxy-3-methyl-butyl-2-carbamate (11)

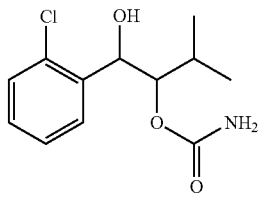 [SMILES: CC(C)C(OC(N)=O)C(O)c1ccccc1Cl]

The substantially same method as described in Example 1 was conducted, except that 1-(2-chlorophenyl)-3-methyl-1,2-butanediol obtained in Preparation Example 22 was used instead of 1-(2-chlorophenyl)-(S,S)-1,2-propanediol, to obtain the title compound (1.5 g, yield 23%).

$^1$H NMR(400 MHz, CDCl$_3$) δ1.00(d, J=6.4 Hz, 3H), 1.09 (d, J=6.4 Hz, 3H), 2.08(m, 1H), 2.76(d, J=6.0 Hz, 1H), 4.59 (br s, 2H), 4.87(dd, J=7.2 Hz, 4.4 Hz, 1H), 5.36(t, J=4.6, 1H), 7.23~7.54(m, 4H)

Example 12

Synthesis of 1-(2-chlorophenyl)-(S)-1-hydroxy-hexyl-(S)-2-carbamate (12)

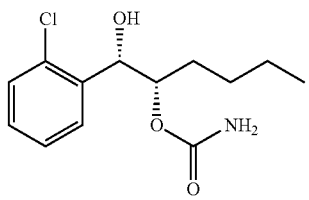 [SMILES: CCCC[C@H](OC(N)=O)[C@@H](O)c1ccccc1Cl]

The substantially same method as described in Example 1 was conducted, except that 1-(2-chlorophenyl)-(S,S)-1,2-hexanediol obtained in Preparation Example 23 was used instead of 1-(2-chlorophenyl)-(S,S)-1,2-propanediol, to obtain the title compound (0.24 g, yield 49%).

$^1$H NMR(400 MHz, CDCl$_3$) δ0.88(t, J=7 Hz, 3H), 1.33~1.42(m, 4H), 1.53~1.71(m, 2H), 2.89(d, J=5.6 Hz, 1H) 4.64(br s, 2H), 5.04(dt, J=5.0, 9.0 Hz, 1H), 5.20(t, J=5.6 Hz, 1H), 7.23~7.55(m, 4H)

Example 13

Synthesis of 1-(2-chlorophenyl)-(R)-1-hydroxy-hexyl-(R)-2-carbamate (13)

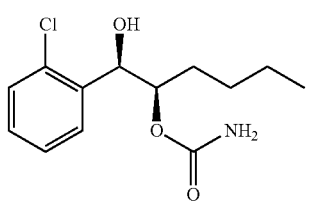 [SMILES: CCCC[C@@H](OC(N)=O)[C@H](O)c1ccccc1Cl]

The substantially same method as described in Example 1 was conducted, except that 1-(2-chlorophenyl)-(R,R)-1,2-hexanediol obtained in Preparation Example 24 was used instead of 1-(2-chlorophenyl)-(S,S)-1,2-propanediol, to obtain the title compound (2.2 g, yield 44%).

$^1$H NMR(400 MHz, CDCl$_3$) δ 0.89(dd, J=5 Hz, 3H), 1.28~1.43(m, 4H), 1.52~1.58(m, 1H), 1.65~1.72(m, 1H), 2.90(d, J=6 Hz, 1H), 4.64(br s, 2H), 5.01~5.06(m, 1H), 5.22 (t, J=6 Hz, 1H), 7.22~7.56(m, 4H)

Example 14

Synthesis of 1-(2-chlorophenyl)-1-hydroxyhexyl-2-carbamate (14)

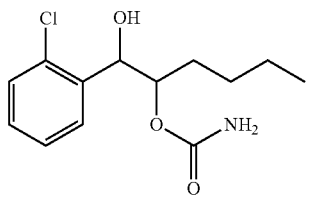 [SMILES: CCCCC(OC(N)=O)C(O)c1ccccc1Cl]

The substantially same method as described in Example 1 was conducted, except that 1-(2-chlorophenyl)-1,2-hexanediol obtained in Preparation Example 25 was used instead of 1-(2-chlorophenyl)-(S,S)-1,2-propanediol, to obtain the title compound (1.6 g, yield 34%).

$^1$H NMR(400 MHz, CDCl$_3$) δ 0.88(dd, J=5 Hz, 3H), 1.31~1.43(m, 4H), 1.63~1.70(m, 1H), 1.52~1.60(m, 1H), 3.06(d, J=6 Hz, 1H), 4.75(br s, 2H), 5.00~5.05(m, 1H), 5.21 (t, J=6 Hz, 1H), 7.22~7.55(m, 4H)

Example 15

Synthesis of 1-(2-chlorophenyl)-(S)-1-hydroxypropyl-(S)-2-N-methylcarbamate (15)

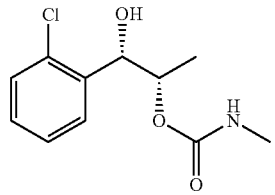 [SMILES: CNC(=O)O[C@@H](C)[C@@H](O)c1ccccc1Cl]

The substantially same method as described in Example 1 was conducted, except that methylamine was used instead of ammonia solution (NH$_4$OH), to obtain the title compound (1.6 g, yield 51%).

$^1$H NMR(400 MHz, CDCl$_3$) δ1.03~1.25(m, 3H), 2.76(s, 3H), 3.34(s, 1H), 4.80(br s 1H), 5.04(t, J=12.5 Hz, 1H), 5.14(s, 1H), 7.20~7.53(m, 4H)

Example 16

Synthesis of 1-(2-chlorophenyl)-(S)-1-hydroxypropyl-(S)-2-N-propylcarbamate (16)

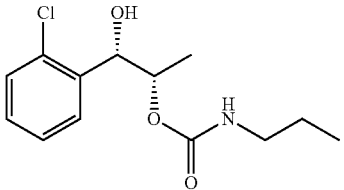 [SMILES: CCCNC(=O)O[C@@H](C)[C@@H](O)c1ccccc1Cl]

The substantially same method as described in Example 1 was conducted, except that propylamine was used instead of ammonia solution (NH₄OH), to obtain the title compound (0.79 g, yield 25%).

¹H NMR(400 MHz, CDCl₃) δ0.90(t, J=6.8 Hz, 3H), 1.20 (d, J=5.96 Hz, 3H), 1.49(dd, J=14.2 Hz, 2H), 3.11(d, J=6.28 Hz, 2H), 3.34(s, 1H), 4.84(br s, 1H), 5.05(t, J=5.88 Hz, 1H), 5.14(s, 1H), 7.22~7.53(m, 4H)

Example 17

Synthesis of 1-(2-chlorophenyl)-(S)-1-hydroxypropyl-(S)-2-N-isopropylcarbamate (17)

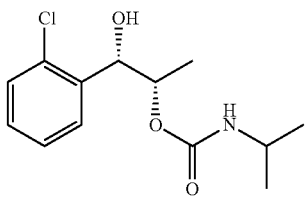 [SMILES: CC(C)NC(=O)O[C@@H](C)[C@@H](O)c1ccccc1Cl]

The substantially same method as described in Example 1 was conducted, except that isopropylamine was used instead of ammonia solution (NH₄OH), to obtain the title compound (1.5 g, yield 41%).

¹H NMR(400 MHz, CDCl₃) δ1.14(dd, J=6.5 Hz, 6H), 1.19 (d, J=6.4 Hz, 3H), 3.21(s, 1H), 3.73~3.82(m, 1H), 4.59(br s, 1H), 5.01~5.07(m, 1H), 5.14(t, J=5.8 Hz, 1H), 7.20~7.53(m, 4H)

Example 18

Synthesis of 1-(2-chlorophenyl)-(S)-1-hydroxypropyl-(S)-2-N-cyclopropylcarbamate (18)

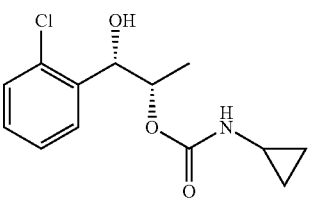 [SMILES: C[C@H](OC(=O)NC1CC1)[C@@H](O)c1ccccc1Cl]

The substantially same method as described in Example 1 was conducted, except that cyclopropylamine was used instead of ammonia solution (NH₄OH), to obtain the title compound (2.2 g, yield 43%).

¹H NMR(400 MHz, CDCl₃) δ0.50~0.56(m, 2H), 0.74(d, J=7.21 Hz, 2H), 1.25(s, 3H), 2.56~2.61(m, 1H), 3.72(s, 1H), 4.98(br s, 1H), 5.05~5.11(m, 1H), 7.16(s, 1H), 7.23~7.54(m, 4H)

Example 19

Synthesis of 1-(2-chlorophenyl)-(S)-1-hydroxypropyl-(S)-2-N-cyclohexyl carbamate (19)

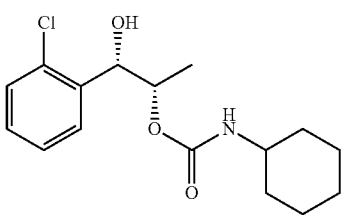 [SMILES: C[C@H](OC(=O)NC1CCCCC1)[C@@H](O)c1ccccc1Cl]

The substantially same method as described in Example 1 was conducted, except that cyclohexylamine was used instead of ammonia solution (NH₄OH), to obtain the title compound (1.1 g, yield 26%).

¹H NMR(400 MHz, CDCl₃) δ1.06~1.40(m, 7H), 1.56~1.61(m, 2H), 1.69~1.71(m, 2H), 1.87~1.94(m, 2H), 3.19(d, J=4.32 Hz, 1H), 3.45(s, 1H), 4.64(br s 1H), 5.02~5.07 (m, 1H), 5.14(t, J=6.08 Hz, 1H) 7.20~7.53(m, 4H)

Example 20

Synthesis of 1-(2-chlorophenyl)-(S)-1-hydroxypropyl-(S)-2-N-benzyl carbamate (20)

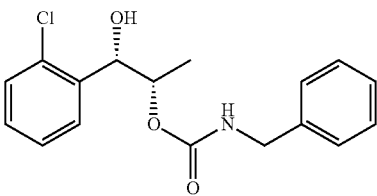 [SMILES: C[C@H](OC(=O)NCc1ccccc1)[C@@H](O)c1ccccc1Cl]

The substantially same method as described in Example 1 was conducted, except that benzylamine was used instead of ammonia solution (NH₄OH), to obtain the title compound (1.2 g, yield 18%).

¹H NMR(400 MHz, CDCl₃) δ 1.27(d, J=10 Hz, 3H), 3.12 (d, J=5 Hz, 1H), 4.37(d, J=6 Hz, 2H), 5.12~5.19(m, 3H), 7.15~7.56(m, 9H)

Example 21

Synthesis of 1-(2-chlorophenyl)-(S)-1-hydroxypropyl-(S)-2-N-bicyclo[2,2,1]heptanescarbamate (21)

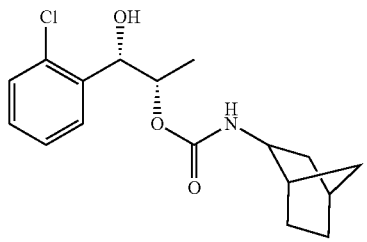 [SMILES: C[C@H](OC(=O)NC1CC2CCC1C2)[C@@H](O)c1ccccc1Cl]

The substantially same method as described in Example 1 was conducted, except that 2-aminonorbornane was used instead of ammonia solution (NH₄OH), to obtain the title compound (1.7 g, yield 32%).

¹H NMR(400 MHz, CDCl₃) δ1.08~1.35(m, 9H), 1.65(br s, 1H), 1.75~1.71(m, 1H), 2.14~2.24(m, 1H), 2.27~2.30(m, 1H), 3.23~3.29(m, 1H), 3.47~3.52(m, 1H), 4.67(br s, 1H), 5.01~5.09(m, 1H), 5.12~5.18(m, 1H), 7.22~7.55(m, 4H)

Example 22

Synthesis of 1-(2-chlorophenyl)-(R)-1-hydroxypropyl-(R)-2-N-methylcarbamate (22)

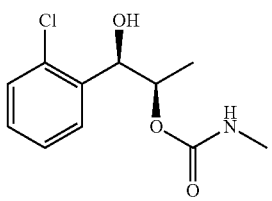 [SMILES: CNC(=O)O[C@H](C)[C@H](O)c1ccccc1Cl]

The substantially same method as described in Example 2 was conducted, except that methylamine was used instead of ammonia solution (NH$_4$OH), to obtain the title compound (3.36 g, yield 60%).

$^1$H NMR(400 MHz, CDCl$_3$) δ 1.20(d, J=6.8 Hz, 3H), 2.80 (d, J=4.8 Hz, 3H), 3.20(d, J=4.4 Hz, 1H), 4.75(br s, 1H), 5.03~5.09(m, 1H), 5.14~5.17(m, 1H), 7.22~7.55(m, 4H)

Example 23

Synthesis of 1-(2-chlorophenyl)-(R)-1-hydroxypropyl-(R)-2-N-propylcarbamate (21)

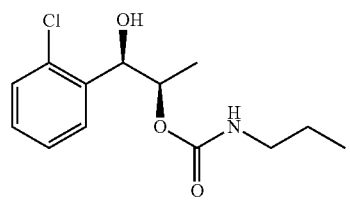 [SMILES: CCCNC(=O)O[C@H](C)[C@H](O)c1ccccc1Cl]

The substantially same method as described in Example 2 was conducted, except that propylamine was used instead of ammonia solution (NH$_4$OH), to obtain the title compound (3.1 g, yield 53%).

$^1$H NMR(400 MHz, CDCl$_3$) δ0.92(t, J=7.6 Hz, 3H), 1.21 (d, J=6.4 Hz, 3H), 1.51(m, 2H), 3.09~3.14(m, 2H), 3.28(d, J=4.4 Hz, 1H), 4.82(br s, 1H), 5.03~5.09(m, 1H), 5.14~5.17 (m, 1H), 7.22~7.55(m. 4H)

Example 24

Synthesis of 1-(2-chlorophenyl)-(R)-1-hydroxypropyl-(R)-2-N-isopropylcarbamate (24)

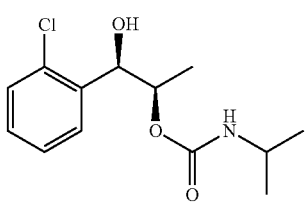 [SMILES: CC(C)NC(=O)O[C@H](C)[C@H](O)c1ccccc1Cl]

The substantially same method as described in Example 2 was conducted, except that isopropylamine was used instead of ammonia solution (NH$_4$OH), to obtain the title compound (0.16 g, yield 27%).

$^1$H NMR(400 MHz, CDCl$_3$) δ0.88~1.16(m, 6H), 1.19~1.26(m, 3H), 3.34(s, 1H), 3.71~3.78(m, 1H), 4.62(br s, 1H), 5.03(t, J=5.8 Hz, 1H), 5.13(d, J=4.9 Hz, 1H), 7.20~7.53 (m, 4H)

Example 25

Synthesis of 1-(2-chlorophenyl)-(R)-1-hydroxypropyl-(R)-2-N-cyclopropylcarbamate (25)

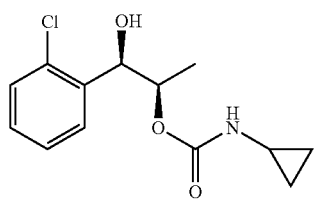 [SMILES: C[C@@H](OC(=O)NC1CC1)[C@H](O)c1ccccc1Cl]

The substantially same method as described in Example 2 was conducted, except that cyclopropylamine was used instead of ammonia solution (NH$_4$OH), to obtain the title compound (3.7 g, yield 60%).

$^1$H NMR(400 MHz, CDCl$_3$) δ0.49~0.54(m, 2H), 0.74(d, J=7.2 Hz, 2H), 1.22(s, 3H), 2.55~2.60(m, 1H), 3.16(s, 1H), 5.00(s, 1H), 5.04~5.11(m, 1H), 5.16(s, 1H), 7.23~7.54(m, 4H)

Example 26

Synthesis of 1-(2-chlorophenyl)-(R)-1-hydroxypropyl-(R)-2-N-cyclohexyl carbamate (26)

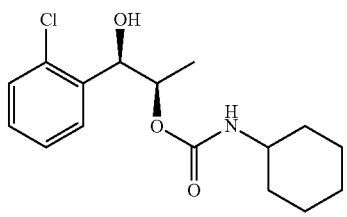 [SMILES: C[C@@H](OC(=O)NC1CCCCC1)[C@H](O)c1ccccc1Cl]

The substantially same method as described in Example 2 was conducted, except that cyclohexylamine was used instead of ammonia solution (NH$_4$OH), to obtain the title compound (1.9 g, yield 28%).

$^1$H NMR(400 MHz, CDCl$_3$) δ1.05~1.38(m, 8H), 1.58~1.70(m, 3H), 1.85~1.95(m, 2H), 3.39~3.47(m, 1H), 3.56(s, 1H), 4.79(br s, 1H), 5.01~5.07(m, 1H), 5.14(t, J=5.2 Hz, 1H), 7.20~7.54(m, 4H)

Example 27

Synthesis of 1-(2-chlorophenyl)-(R)-1-hydroxypropyl-(R)-2-N-benzylcarbamate (27)

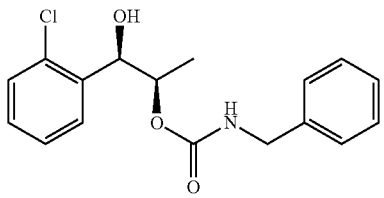 [SMILES: C[C@@H](OC(=O)NCc1ccccc1)[C@H](O)c1ccccc1Cl]

The substantially same method as described in Example 2 was conducted, except that benzylamine was used instead of ammonia solution (NH₄OH), to obtain the title compound (0.52 g, yield 19%).

¹H NMR(400 MHz, CDCl₃) δ1.25(d, J=6 Hz, 3H), 1.64(s, 1H), 3.13(d, J=4.4 Hz, 1H), 4.37(d, J=5.6 Hz, 2H), 5.12~5.19 (m, 2H), 7.23~7.55(m, 9H)

Example 28

Synthesis of 1-(2-chlorophenyl)-(R)-1-hydroxypropyl-(R)-2-N-bicyclo[2,2,1]heptanecarbamate (28)

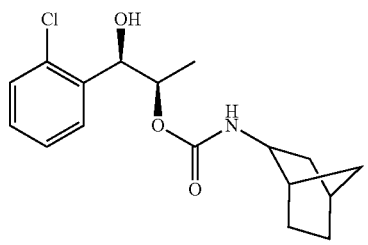 [SMILES: C[C@@H](OC(=O)NC1CC2CCC1C2)[C@H](O)c1ccccc1Cl]

The substantially same method as described in Example 2 was conducted, except that 2-aminonorbornane was used instead of ammonia solution (NH₄OH), to obtain the title compound (1.7 g, yield 20~50%).

¹H NMR(400 MHz, CDCl₃) δ1.08~1.35(m, 9H), 1.65(br s, 1H), 1.75~1.71(m, 1H), 2.14~2.24(m, 1H), 2.27~2.30(m, 1H), 3.23~3.29(m, 1H), 3.47~3.52(m, 1H), 4.67(br s, 1H), 5.01~5.09(m, 1H), 5.12~5.18(m, 1H), 7.22~7.55(m, 4H)

Example 29

Synthesis of 1-(2-chlorophenyl)-1-hydroxypropyl-2-N-methylcarbamate (29)

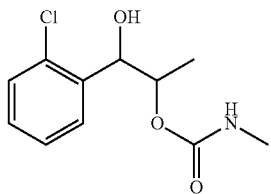 [SMILES: CNC(=O)OC(C)C(O)c1ccccc1Cl]

The substantially same method as described in Example 3 was conducted, except that methylamine was used instead of ammonia solution (NH₄OH), to obtain the title compound (2.6 g, yield 45%).

¹H NMR(400 MHz, CDCl₃) δ 1.21(d, J=6 Hz, 3H), 2.81(d, J=5 Hz, 3H), 3.14(d, J=4 Hz, 1H), 4.72(br s, 1H), 5.07(dd, J=6 Hz, 1H), 5.16(t, J=6 Hz, 1H), 7.22~7.56(m, 4H)

Example 30

Synthesis of 1-(2-chlorophenyl)-1-hydroxypropyl-2-N-propylcarbamate (30)

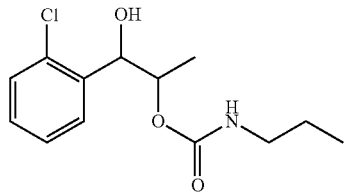 [SMILES: CCCNC(=O)OC(C)C(O)c1ccccc1Cl]

The substantially same method as described in Example 3 was conducted, except that propylamine was used instead of ammonia solution (NH₄OH), to obtain the title compound (1.0 g, yield 17%).

¹H NMR(400 MHz, CDCl₃) δ 0.92(t, J=7 Hz, 3H), 1.21(d, J=6 Hz, 3H), 1.53(dd, J=7 Hz, 2H), 3.13(dd, J=7 Hz, 2H), 3.28(d, 1H), 4.82(S, 1H), 5.06(dd, J=7 Hz, 1H), 5.16(t, J=5 Hz, 1H), 7.21~7.56(m, 4H)

Example 31

Synthesis of 1-(2-chlorophenyl)-1-hydroxypropyl-2-N-isopropylcarbamate (31)

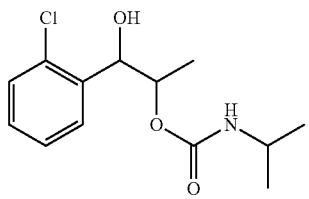

The substantially same method as described in Example 3 was conducted, except that isopropylamine was used instead of ammonia solution (NH₄OH), to obtain the title compound (0.54 g, yield 16%).

¹H NMR(400 MHz, CDCl₃) δ 1.16(dd, J=6 Hz, 6H), 1.21 (d, J=6 Hz, 3H), 3.23(d, J=6 Hz, 1H), 3.75~3.84(m, 1H), 4.61(br s, 1H), 5.06(t, J=6 Hz, 1H), 5.16(t, J=6 Hz, 1H), 7.22~7.56(m, 4H)

Example 32

Synthesis of 1-(2-chlorophenyl)-1-hydroxypropyl-2-N-cyclopropylcarbamate (32)

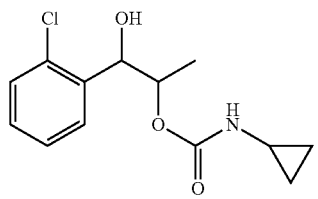 [SMILES: CC(OC(=O)NC1CC1)C(O)c1ccccc1Cl]

The substantially same method as described in Example 3 was conducted, except that cyclopropylamine was used instead of ammonia solution (NH₄OH), to obtain the title compound (1.0 g, yield 17%).

¹H NMR(400 MHz, CDCl₃) δ 0.50(t, J=6 Hz, 2H), 0.77(t, J=3 Hz, 2H), 1.12(d, J=7 Hz, 3H), 2.53~2.59(m, 1H), 3.22(d, J=4 Hz, 1H), 5.08(dd, J=6 Hz, 1H), 5.15(S, 1H), 7.22~7.55 (m, 4H)

Example 33

Synthesis of 1-(2-chlorophenyl)-1-hydroxypropyl-2-N-cyclohexylcarbamate (33)

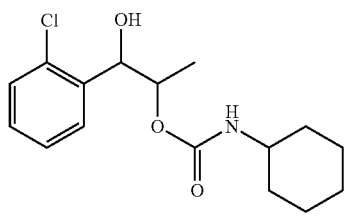 [SMILES: CC(OC(=O)NC1CCCCC1)C(O)c1ccccc1Cl]

The substantially same method as described in Example 3 was conducted, except that cyclohexylamine was used instead of ammonia solution (NH₄OH), to obtain the title compound (2.2 g, yield 33%).

¹H NMR(400 MHz, CDCl₃) δ 1.07~1.17(m, 3H), 1.21(d, J=6 Hz, 3H), 1.29~1.42(m, 3H), 1.72(dd, J=6 Hz, 2H), 1.92 (dd, J=6 Hz, 2H), 3.26(d, J=4 Hz, 1H), 3.46(t, J=4 Hz, 1H), 4.68(d, J=6 Hz, 1H), 5.07(dd, J=6 Hz, 1H), 5.16(t, J=6 Hz, 1H), 7.22~7.55(m, 4H)

Example 34

Synthesis of 1-(2-chlorophenyl)-1-hydroxypropyl-2-N-benzylcarbamate (34)

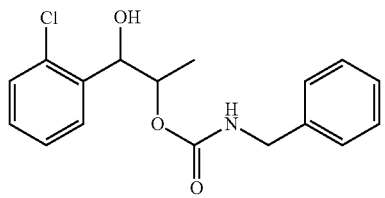 [SMILES: CC(OC(=O)NCc1ccccc1)C(O)c1ccccc1Cl]

The substantially same method as described in Example 3 was conducted, except that benzylamine was used instead of ammonia solution (NH₄OH), to obtain the title compound (1.3 g, yield 19%).

¹H NMR(400 MHz, CDCl₃) δ 1.25(d, J=6 Hz, 3H), 3.16(d, J=4 Hz, 1H), 4.36(d, J=6 Hz, 2H), 5.14(dd, J=6 Hz, 3H), 7.23~7.56(m, 9H), yield: 19% (1.3 g)

Example 35

Synthesis of 1-(2-chlorophenyl)-1-hydroxypropyl-2-N-bicyclo[2,2,1]heptanecarbamate (35)

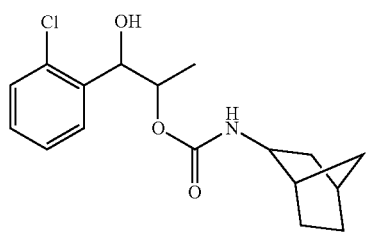 [SMILES: CC(OC(=O)NC1CC2CCC1C2)C(O)c1ccccc1Cl]

The substantially same method as described in Example 3 was conducted, except that 2-aminonorbornane was used instead of ammonia solution (NH₄OH), to obtain the title compound (1.7 g, yield 20~50%).

¹H NMR(400 MHz, CDCl₃) δ 1.08~1.35(m, 9H), 1.65(br s, 1H), 1.75~1.71(m, 1H), 2.14~2.24(m, 1H), 2.27~2.30(m, 1H), 3.23~3.29(m, 1H), 3.47~3.52(m, 1H), 4.67(br s, 1H), 5.01~5.09(m, 1H), 5.12~5.18(m, 1H), 7.22~7.55(m, 4H)

Example 36

Synthesis of 1-(2,4-dichlorophenyl)-(S)-1-hydroxypropyl-(S)-2-carbamate (36)

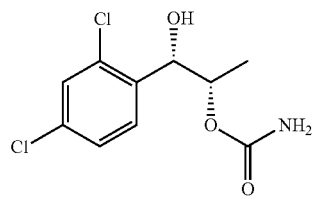 [SMILES: C[C@H](OC(N)=O)[C@@H](O)c1ccc(Cl)cc1Cl]

The substantially same method as described in Example 1 was conducted, except that 1-(2,4-dichlorophenyl)-(S,S)-1,2-propanediol obtained in Preparation Example 26 was used instead of 1-(2-chlorophenyl)-(S,S)-1,2-propanediol, to obtain the title compound (0.14 g, yield 34%).

¹H NMR(400 MHz, CDCl₃) δ1.22(d, J=6.4 Hz, 3H), 4.16 (br t, 1H) 4.96(br t, 3H), 5.07(t, J=4.8 Hz, 1H), 7.23~7.52(m, 3H)

Example 37

Synthesis of 1-(2,6-dichlorophenyl)-(S)-1-hydroxypropyl-(S)-2-carbamate (37)

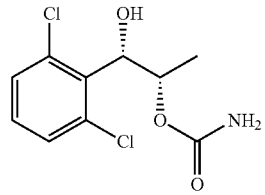 [SMILES: C[C@H](OC(N)=O)[C@@H](O)c1c(Cl)cccc1Cl]

The substantially same method as described in Example 1 was conducted, except that 1-(2,6-dichlorophenyl)-(S,S)-1,2-propanediol obtained in Preparation Example 38 was used instead of 1-(2-chlorophenyl)-(S,S)-1,2-propanediol, to obtain the title compound (0.22 g, yield 49%).

¹H NMR(400 MHz, CDCl₃) δ1.15(d, J=6.4 Hz, 3H), 3.66 (d, J=9.2 Hz, 1H), 4.73(br s, 2H), 5.43(t, J=9.0 Hz, 1H), 5.62~5.69(m, 1H), 7.18~7.22(m, 3H),

Example 38

Synthesis of 1-(2,3-dichlorophenyl)-(S)-1-hydroxypropyl-(S)-2-carbamate (38)

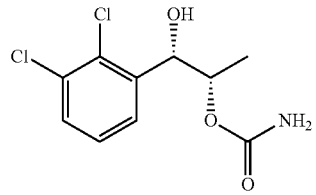

The substantially same method as described in Example 1 was conducted, except that 1-(2,3-dichlorophenyl)-(S,S)-1,2-propanediol obtained in Preparation Example 57 was used instead of 1-(2-chlorophenyl)-(S,S)-1,2-propanediol, to obtain the title compound (0.21 g, yield 20~60%).

$^1$H NMR(400 MHz, CDCl$_3$) δ1.15(d, J=6.4 Hz, 3H), 3.66 (d, J=9.2 Hz, 1H), 4.73(br s, 2H), 5.43(t, J=9.0 Hz, 1H), 5.62~5.69(m, 1H), 7.18~7.22(m, 3H),

Example 39

Synthesis of 1-(2,4-dichlorophenyl)-(S)-1-hydroxy-butyl-(S)-2-carbamate (39)

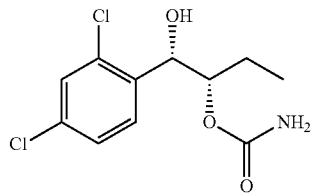

The substantially same method as described in Example 1 was conducted, except that 1-(2,4-dichlorophenyl)-(S,S)-1,2-butanediol obtained in Preparation Example 29 was used instead of 1-(2-chlorophenyl)-(S,S)-1,2-propanediol, to obtain the title compound (0.23 g, yield 52%).

$^1$H NMR(400 MHz, CDCl$_3$) δ0.96(t, J=7.4 Hz, 3H), 1.58~1.74(m, 2H), 2.98(d, J=5.6 Hz, 1H) 4.68(br s, 2H), 5.59(dt, J=5.2, 8.8 Hz, 1H), 5.19(t, J=5.4 Hz, 1H), 7.30~7.50 (m, 3H)

Example 40

Synthesis of 1-(2,6-dichlorophenyl)-(S)-1-hydroxy-butyl-(S)-2-carbamate (40)

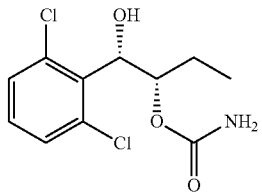 [SMILES: CC[C@H](OC(N)=O)[C@@H](O)c1c(Cl)cccc1Cl]

The substantially same method as described in Example 1 was conducted, except that 1-(2,6-dichlorophenyl)-(S,S)-1,2-butanediol obtained in Preparation Example 41 was used instead of 1-(2-chlorophenyl)-(S,S)-1,2-propanediol, to obtain the title compound (0.49 g, yield 34%).

$^1$H NMR(400 MHz, CDCl$_3$) δ0.92(t, J=7.4 Hz, 3H), 1.30~1.38(m, 1H), 1.57~1.64(m, 1H), 3.74(d, J=9.2 Hz, 1H), 4.80(br s, 2H), 5.40~5.50(m, 2H), 7.17~7.34(m, 3H)

Example 41

Synthesis of 1-(2,4-dichlorophenyl)-(S)-1-hydroxy-3-methyl-butyl-(S)-2-carbamate (41)

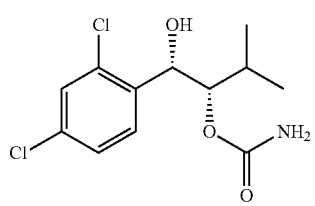

The substantially same method as described in Example 1 was conducted, except that 1-(2,4-dichlorophenyl)-3-methyl-(S,S)-1,2-butanediol obtained in Preparation Example 32 was used instead of 1-(2-chlorophenyl)-(S,S)-1,2-propanediol, to obtain the title compound (0.13 g, yield 20~60%).

$^1$H NMR(400 MHz, CDCl$_3$) δ1.00(t, J=7.2 Hz, 6H), 1.73~1.79(m, 1H), 3.67~3.69(m, 1H), 4.85(br s, 2H), 5.40~5.43(m, 1H), 5.49~5.54(m, 1H), 7.30~7.50(m, 3H)

Example 42

Synthesis of 1-(2,6-dichlorophenyl)-(S)-1-hydroxy-3-methyl-butyl-(S)-2-carbamate (42)

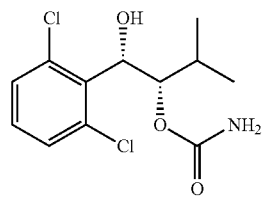 [SMILES: CC(C)[C@H](OC(N)=O)[C@@H](O)c1c(Cl)cccc1Cl]

The substantially same method as described in Example 1 was conducted, except that 1-(2,6-dichlorophenyl)-3-methyl-(S,S)-1,2-butanediol obtained in Preparation Example 44 was used instead of 1-(2-chlorophenyl)-(S,S)-1,2-propanediol, to obtain the title compound (0.12 g, yield 20%).

$^1$H NMR(400 MHz, CDCl$_3$) δ1.00(t, J=7.2 Hz, 6H), 1.73~1.79(m, 1H), 3.67~3.69(m, 1H), 4.85(br s, 2H), 5.40~5.43(m, 1H), 5.49~5.54(m, 1H), 7.16~7.33(m, 3H)

Example 43

Synthesis of 1-(2,4-dichlorophenyl)-(S)-1-hydroxy-hexyl-(S)-2-carbamate (43)

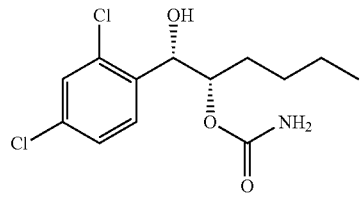

The substantially same method as described in Example 1 was conducted, except that 1-(2,4-dichlorophenyl)-(S,S)-1,2-hexanediol obtained in Preparation Example 35 was used instead of 1-(2-chlorophenyl)-(S,S)-1,2-propanediol, to obtain the title compound (0.94 g, yield 81%).

$^1$H NMR(400 MHz, CDCl$_3$) δ0.89(t, J=3.6 Hz, 3H), 1.28~1.42(m, 4H), 1.52~1.59(m, 1H), 1.64~1.71(m, 1H), 2.98(d, J=5.6 Hz, 1H), 4.67(br s, 2H), 4.96~5.00(m, 1H), 5.17(t, J=5.6 Hz, 1H), 7.30~7.49(m 3H)

Example 44

Synthesis of 1-(2,6-dichlorophenyl)-(S)-1-hydroxy-hexyl-(S)-2-carbamate (44)

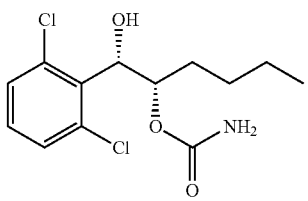

The substantially same method as described in Example 1 was conducted, except that 1-(2,6-dichlorophenyl)-(S,S)-1,2-hexanediol obtained in Preparation Example 47 was used instead of 1-(2-chlorophenyl)-(S,S)-1,2-propanediol, to obtain the title compound (0.15 g, yield 31%).

$^1$H NMR(400 MHz, CDCl$_3$) δ0.84(t, J=7.0 Hz, 3H), 1.20~1.35(m, 4H), 1.36~1.41(m, 1H), 1.59~1.63(m, 1H), 3.71(d, J=10.0 Hz, 1H), 4.74(br s, 2H), 5.40~5.44(m, 1H), 5.52~5.57(m, 1H), 7.17~7.35(m, 3H)

Example 45

Synthesis of 1-(2,4-dichlorophenyl)-(R)-1-hydroxypropyl-(R)-2-carbamate (45)

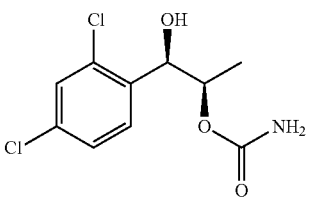 [SMILES: C[C@@H](OC(N)=O)[C@H](O)c1ccc(Cl)cc1Cl]

The substantially same method as described in Example 1 was conducted, except that 1-(2,4-dichlorophenyl)-(R,R)-1,2-propanediol obtained in Preparation Example 27 was used instead of 1-(2-chlorophenyl)-(S,S)-1,2-propanediol, to obtain the title compound (0.14 g, yield 20~60%).

$^1$H NMR(400 MHz, CDCl$_3$) δ1.22(d, J=6.4 Hz, 3H), 4.16 (br t, 1H) 4.96(br t, 3H), 5.07(t, J=4.8 Hz, 1H), 7.23~7.52(m, 3H)

Example 46

Synthesis of 1-(2,6-dichlorophenyl)-(R)-1-hydroxypropyl-(R)-2-carbamate (46)

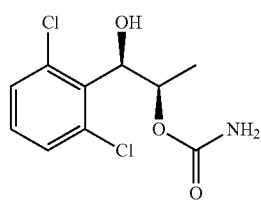 [SMILES: C[C@@H](OC(N)=O)[C@H](O)c1c(Cl)cccc1Cl]

The substantially same method as described in Example 1 was conducted, except that 1-(2,6-dichlorophenyl)-(R,R)-1,2-propanediol obtained in Preparation Example 39 was used instead of 1-(2-chlorophenyl)-(S,S)-1,2-propanediol, to obtain the title compound (0.21 g, yield 20~60%).

$^1$H NMR(400 MHz, CDCl$_3$) δ1.15(d, J=6.4 Hz, 3H), 3.66 (d, J=9.2 Hz, 1H), 4.73(br s, 2H), 5.43(t, J=9.0 Hz, 1H), 5.62~5.69(m, 1H), 7.18~7.22(m, 3H),

Example 47

Synthesis of 1-(2,3-dichlorophenyl)-(R)-1-hydroxypropyl-(R)-2-carbamate (47)

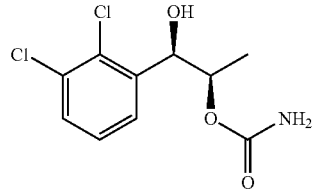 [SMILES: C[C@@H](OC(N)=O)[C@H](O)c1cccc(Cl)c1Cl]

The substantially same method as described in Example 1 was conducted, except that 1-(2,3-dichlorophenyl)-(R,R)-1,2-propanediol obtained in Preparation Example 58 was used instead of 1-(2-chlorophenyl)-(S,S)-1,2-propanediol, to obtain the title compound (0.08 g, yield 20~60%).

$^1$H NMR(400 MHz, CDCl$_3$) δ1.15(d, J=6.4 Hz, 3H), 3.66 (d, J=9.2 Hz, 1H), 4.73(br s, 2H), 5.43(t, J=9.0 Hz, 1H), 5.62~5.69(m, 1H), 7.18~7.22(m, 3H),

Example 48

Synthesis of 1-(2,4-dichlorophenyl)-(R)-1-hydroxybutyl-(R)-2-carbamate (48)

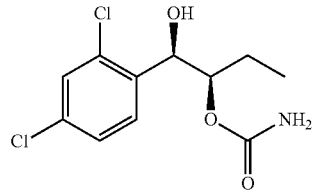 [SMILES: CC[C@@H](OC(N)=O)[C@H](O)c1ccc(Cl)cc1Cl]

The substantially same method as described in Example 1 was conducted, except that 1-(2,4-dichlorophenyl)-(R,R)-1,2-butanediol obtained in Preparation Example 30 was used instead of 1-(2-chlorophenyl)-(S,S)-1,2-propanediol, to obtain the title compound (0.23 g, yield 20~60%).

$^1$H NMR(400 MHz, CDCl$_3$) δ0.96(t, J=7.4 Hz, 3H), 1.58~1.74(m, 2H), 2.98(d, J=5.6 Hz, 1H) 4.68(br s, 2H), 5.59(dt, J=5.2, 8.8 Hz, 1H), 5.19(t, J=5.4 Hz, 1H), 7.30~7.50 (m, 3H)

Example 49

Synthesis of 1-(2,6-dichlorophenyl)-(R)-1-hydroxybutyl-(R)-2-carbamate (49)

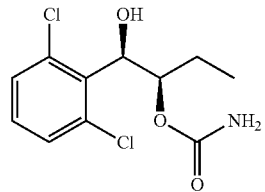 [SMILES: CC[C@@H](OC(N)=O)[C@H](O)c1c(Cl)cccc1Cl]

The substantially same method as described in Example 1 was conducted, except that 1-(2,6-dichlorophenyl)-(R,R)-1,2-butanediol obtained in Preparation Example 42 was used instead of 1-(2-chlorophenyl)-(S,S)-1,2-propanediol, to obtain the title compound (0.49 g, yield 20~60%).

$^1$H NMR(400 MHz, CDCl$_3$) δ0.92(t, J=7.4 Hz, 3H), 1.30~1.38(m, 1H), 1.57~1.64(m, 1H), 3.74(d, J=9.2 Hz, 1H), 4.80(br s, 2H), 5.40~5.50(m, 2H), 7.17~7.34(m, 3H)

Example 50

Synthesis of 1-(2,4-dichlorophenyl)-(R)-1-hydroxy-3-methyl-butyl-(R)-2-carbamate (50)

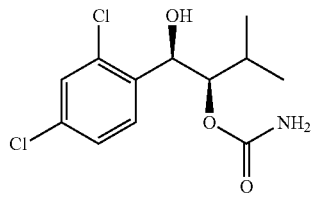 [SMILES: CC(C)[C@@H](OC(N)=O)[C@H](O)c1ccc(Cl)cc1Cl]

The substantially same method as described in Example 1 was conducted, except that 1-(2,4-dichlorophenyl)-3-methyl-(R,R)-1,2-butanediol obtained in Preparation Example 33 was used instead of 1-(2-chlorophenyl)-(S,S)-1,2-propanediol, to obtain the title compound (0.23 g, yield 20~60%).

$^1$H NMR(400 MHz, CDCl$_3$) δ1.00(t, J=7.2 Hz, 6H), 1.73~1.79(m, 1H), 3.67~3.69(m, 1H), 4.85(br s, 2H), 5.40~5.43(m, 1H), 5.49~5.54(m, 1H), 7.30~7.50(m, 3H)

Example 51

Synthesis of 1-(2,6-dichlorophenyl)-(R)-1-hydroxy-3-methyl-butyl-(R)-2-carbamate (51)

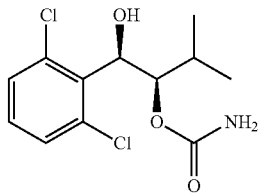 [SMILES: CC(C)[C@@H](OC(N)=O)[C@H](O)c1c(Cl)cccc1Cl]

The substantially same method as described in Example 1 was conducted, except that 1-(2,6-dichlorophenyl)-3-methyl-(R,R)-1,2-butanediol obtained in Preparation Example 45 was used instead of 1-(2-chlorophenyl)-(S,S)-1,2-propanediol, to obtain the title compound (0.14 g, yield 20~60%).

$^1$H NMR(400 MHz, CDCl$_3$) δ1.00(t, J=7.2 Hz, 6H), 1.73~1.79(m, 1H), 3.67~3.69(m, 1H), 4.85(br s, 2H), 5.40~5.43(m, 1H), 5.49~5.54(m, 1H), 7.16~7.33(m, 3H)

Example 52

Synthesis of 1-(2,4-dichlorophenyl)-(R)-1-hydroxy-hexyl-(R)-2-carbamate (52)

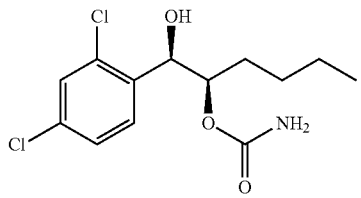 [SMILES: CCCC[C@@H](OC(N)=O)[C@H](O)c1ccc(Cl)cc1Cl]

The substantially same method as described in Example 1 was conducted, except that 1-(2,4-dichlorophenyl)-(R,R)-1,2-hexanediol obtained in Preparation Example 36 was used instead of 1-(2-chlorophenyl)-(S,S)-1,2-propanediol, to obtain the title compound (0.84 g, yield 20~60%).

$^1$H NMR(400 MHz, CDCl$_3$) δ0.89(t, J=3.6 Hz, 3H), 1.28~1.42(m, 4H), 1.52~1.59(m, 1H), 1.64~1.71(m, 1H), 2.98(d, J=5.6 Hz, 1H), 4.67(br s, 2H), 4.96~5.00(m, 1H), 5.17(t, J=5.6 Hz, 1H), 7.30~7.49(m, 3H)

Example 53

Synthesis of 1-(2,6-dichlorophenyl)-(R)-1-hydroxy-hexyl-(R)-2-carbamate (53)

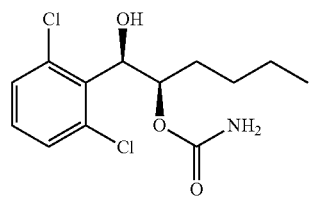 [SMILES: CCCC[C@@H](OC(N)=O)[C@H](O)c1c(Cl)cccc1Cl]

The substantially same method as described in Example 1 was conducted, except that 1-(2,6-dichlorophenyl)-(R,R)-1,2-hexanediol obtained in Preparation Example 48 was used instead of 1-(2-chlorophenyl)-(S,S)-1,2-propanediol, to obtain the title compound (0.15 g, yield 20~60%).

$^1$H NMR(400 MHz, CDCl$_3$) δ0.84(t, J=7.0 Hz, 3H), 1.20~1.35(m, 4H), 1.36~1.41(m, 1H), 1.59~1.63(m, 1H), 3.71(d, J=10.0 Hz, 1H), 4.74(br s, 2H), 5.40~5.44(m, 1H), 5.52~5.57(m, 1H), 7.17~7.35(m, 3H)

Example 54

Synthesis of 1-(2,4-dichlorophenyl)-1-hydroxypropyl-2-carbamate (54)

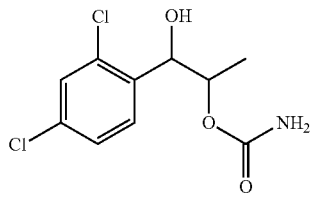 [SMILES: CC(OC(N)=O)C(O)c1ccc(Cl)cc1Cl]

The substantially same method as described in Example 1 was conducted, except that 1-(2,4-dichlorophenyl)-1,2-propanediol obtained in Preparation Example 28 was used instead of 1-(2-chlorophenyl)-(S,S)-1,2-propanediol, to obtain the title compound (0.14 g, yield 20~60%).

$^1$H NMR(400 MHz, CDCl$_3$) δ1.22(d, J=6.4 Hz, 3H), 4.16 (br t, 1H) 4.96(br t, 3H), 5.07(t, J=4.8 Hz, 1H), 7.23~7.52(m, 3H)

Example 55

Synthesis of
1-(2,6-dichlorophenyl)-1-hydroxypropyl-2-carbamate
(55)

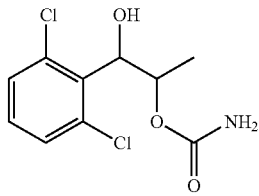 [SMILES: CC(OC(N)=O)C(O)c1c(Cl)cccc1Cl]

The substantially same method as described in Example 1 was conducted, except that 1-(2,6-dichlorophenyl)-1,2-propanediol obtained in Preparation Example 40 was used instead of 1-(2-chlorophenyl)-(S,S)-1,2-propanediol, to obtain the title compound (0.19 g, yield 20~60%).

$^1$H NMR(400 MHz, CDCl$_3$) δ1.15(d, J=6.4 Hz, 3H), 3.66 (d, J=9.2 Hz, 1H), 4.73(br s, 2H), 5.43(t, J=9.0 Hz, 1H), 5.62~5.69(m, 1H), 7.18~7.22(m, 3H),

Example 56

Synthesis of
1-(2,3-dichlorophenyl)-1-hydroxypropyl-2-carbamate
(56)

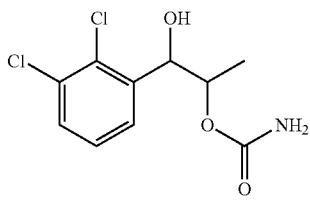 [SMILES: CC(OC(N)=O)C(O)c1cccc(Cl)c1Cl]

The substantially same method as described in Example 1 was conducted, except that 1-(2,3-dichlorophenyl)-1,2-propanediol obtained in Preparation Example 59 was used instead of 1-(2-chlorophenyl)-(S,S)-1,2-propanediol, to obtain the title compound (0.21 g, yield 20~60%).

$^1$H NMR(400 MHz, CDCl$_3$) δ1.15(d, J=6.4 Hz, 3H), 3.66 (d, J=9.2 Hz, 1H), 4.73(br s, 2H), 5.43(t, J=9.0 Hz, 1H), 5.62~5.69(m, 1H), 7.18~7.22(m, 3H),

Example 57

Synthesis of
1-(2,4-dichlorophenyl)-1-hydroxybutyl-2-carbamate
(57)

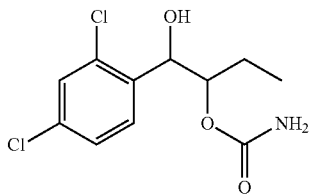 [SMILES: CCC(OC(N)=O)C(O)c1ccc(Cl)cc1Cl]

The substantially same method as described in Example 1 was conducted, except that 1-(2,4-dichlorophenyl)-1,2-butanediol obtained in Preparation Example 31 was used instead of 1-(2-chlorophenyl)-(S,S)-1,2-propanediol, to obtain the title compound (0.23 g, yield 20~60%).

$^1$H NMR(400 MHz, CDCl$_3$) δ0.96(t, J=7.4 Hz, 3H), 1.58~1.74(m, 2H), 2.98(d, J=5.6 Hz, 1H) 4.68(br s, 2H), 5.59(dt, J=5.2, 8.8 Hz, 1H), 5.19(t, J=5.4 Hz, 1H), 7.30~7.50 (m, 3H)

Example 58

Synthesis of
1-(2,6-dichlorophenyl)-1-hydroxybutyl-2-carbamate
(58)

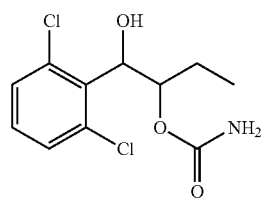 [SMILES: CCC(OC(N)=O)C(O)c1c(Cl)cccc1Cl]

The substantially same method as described in Example 1 was conducted, except that 1-(2,6-dichlorophenyl)-1,2-butanediol obtained in Preparation Example 43 was used instead of 1-(2-chlorophenyl)-(S,S)-1,2-propanediol, to obtain the title compound (0.49 g, yield 20~60%).

$^1$H NMR(400 MHz, CDCl$_3$) δ0.92(t, J=7.4 Hz, 3H), 1.30~1.38(m, 1H), 1.57~1.64(m, 1H), 3.74(d, J=9.2 Hz, 1H), 4.80(br s, 2H), 5.40~5.50(m, 2H), 7.17~7.34(m, 3H)

Example 59

Synthesis of 1-(2,4-dichlorophenyl)-1-hydroxy-3-methyl-butyl-2-carbamate (59)

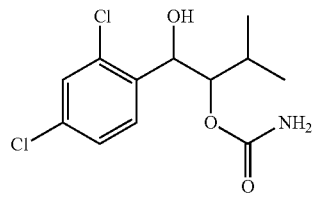 [SMILES: CC(C)C(OC(N)=O)C(O)c1ccc(Cl)cc1Cl]

The substantially same method as described in Example 1 was conducted, except that 1-(2,4-dichlorophenyl)-3-methyl-1,2-butanediol obtained in Preparation Example 34 was used instead of 1-(2-chlorophenyl)-(S,S)-1,2-propanediol, to obtain the title compound (0.13 g, yield 20~60%).

$^1$H NMR(400 MHz, CDCl$_3$) δ1.00(t, J=7.2 Hz, 6H), 1.73~1.79(m, 1H), 3.67~3.69(m, 1H), 4.85(br s, 2H), 5.40~5.43(m, 1H), 5.49~5.54(m, 1H), 7.30~7.50(m, 3H)

Example 60

Synthesis of 1-(2,6-dichlorophenyl)-1-hydroxy-3-methyl-butyl-2-carbamate (60)

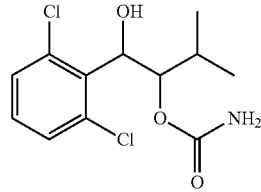 [SMILES: CC(C)C(OC(N)=O)C(O)c1c(Cl)cccc1Cl]

The substantially same method as described in Example 1 was conducted, except that 1-(2,6-dichlorophenyl)-3-methyl-1,2-butanediol obtained in Preparation Example 46 was used instead of 1-(2-chlorophenyl)-(S,S)-1,2-propanediol, to obtain the title compound (0.13 g, yield 20~60%).

$^1$H NMR(400 MHz, CDCl$_3$) δ1.00(1, I=7.2 Hz, 6H), 1.73~1.79(m, 1H), 3.67~3.69(m, 1H), 4.85(br s, 2H), 5.40~5.43(m, 1H), 5.49~5.54(m, 1H), 7.16~7.33(m, 3H)

Example 61

Synthesis of 1-(2,4-dichlorophenyl)-1-hydroxyhexyl-2-carbamate (61)

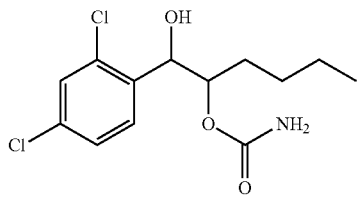 [SMILES: CCCCC(OC(N)=O)C(O)c1ccc(Cl)cc1Cl]

The substantially same method as described in Example 1 was conducted, except that 1-(2,4-dichlorophenyl)-1,2-hexanediol obtained in Preparation Example 37 was used instead of 1-(2-chlorophenyl)-(S,S)-1,2-propanediol, to obtain the title compound (0.94 g, yield 20~60%).

$^1$H NMR(400 MHz, CDCl$_3$) δ0.89(t, J=3.6 Hz, 3H), 1.28~1.42(m, 4H), 1.52~1.59(m, 1H), 1.64~1.71(m, 1H), 2.98(d, J=5.6 Hz, 1H), 4.67(br s, 2H), 4.96~5.00(m, 1H), 5.17(t, J=5.6 Hz, 1H), 7.30~7.49(m, 3H)

Example 62

Synthesis of 1-(2,6-dichlorophenyl)-1-hydroxyhexyl-2-carbamate (62)

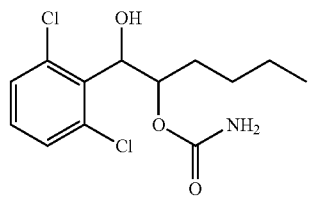 [SMILES: CCCCC(OC(N)=O)C(O)c1c(Cl)cccc1Cl]

The substantially same method as described in Example 1 was conducted, except that 1-(2,6-dichlorophenyl)-1,2-hexanediol obtained in Preparation Example 49 was used instead of 1-(2-chlorophenyl)-(S,S)-1,2-propanediol, to obtain the title compound (0.15 g, yield 20~60%).

$^1$H NMR(400 MHz, CDCl$_3$) δ0.84(t, J=7.0 Hz, 3H), 1.20~1.35(m, 4H), 1.36~1.41(m, 1H), 1.59~1.63(m, 1H), 3.71(d, J=10.0 Hz, 1H), 4.74(br s, 2H), 5.40~5.44(m, 1H), 5.52~5.57(m, 1H), 7.17~7.35(m, 3H)

Example 63

Synthesis of 1-(2-fluorophenyl)-(S)-1-hydroxypropyl-(S)-2-carbamate (63)

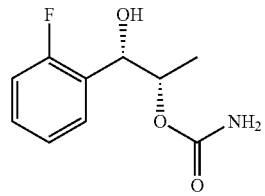

The substantially same method as described in Example 1 was conducted, except that 1-(2-fluorophenyl)-(S,S)-1,2-propanediol (12.23 g) obtained in Preparation Example 61 was used instead of 1-(2-chlorophenyl)-(S,S)-1,2-propanediol, to obtain the title compound (6.11 g, yield 40%).

$^1$H NMR(400 MHz, CDCl$_3$) δ1.19(d, J=5.2 Hz, 3H), 2.93 (d, J=4.4 Hz, 1H), 4.71(br s, 2H), 4.99~5.06(m, H), 7.04~7.48 (m, 4H)

Example 64

Synthesis of 1-(2-fluorophenyl)-(R)-1-hydroxypropyl-(R)-2-carbamate (64)

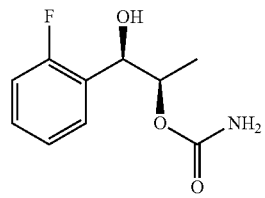

The substantially same method as described in Example 1 was conducted, except that 1-(2-fluorophenyl)-(R,R)-1,2-propanediol (6.26 g) obtained in Preparation Example 62 was used instead of 1-(2-chlorophenyl)-(S,S)-1,2-propanediol, to obtain the title compound (3.13 g, yield 40%).

$^1$H NMR(400 MHz, CDCl$_3$) δ1.19(d, J=5.2 Hz, 3H), 2.93 (d, J=4.4 Hz, 1H), 4.71(br s, 2H), 4.99~5.06(m, H), 7.04~7.48 (m, 4H)

Example 65

Synthesis of 1-(2-iodophenyl)-(S)-1-hydroxypropyl-(S)-2-carbamate (65)

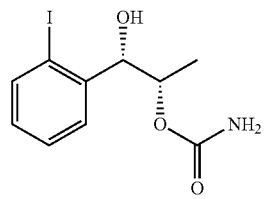

The substantially same method as described in Example 1 was conducted, except that 1-(2-iodophenyl)-(S,S)-1,2-propanediol obtained in Preparation Example 66 was used instead of 1-(2-chlorophenyl)-(S,S)-1,2-propanediol, to obtain the title compound (2.2 g, yield 30~60%).

¹H NMR(400 MHz, CDCl₃) δ1.27(d, J=6.4 Hz, 3H), 3.09 (br s, 1H), 4.83(br s, 2H), 5.00~5.10(m, 2H), 7.00~7.76(m, 4H)

Example 66

Synthesis of 1-(2-iodophenyl)-(R)-1-hydroxypropyl-(R)-2-carbamate (66)

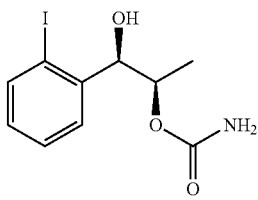

The substantially same method as described in Example 1 was conducted, except that 1-(2-iodophenyl)-(R,R)-1,2-propanediol obtained in Preparation Example 67 was used instead of 1-(2-chlorophenyl)-(S,S)-1,2-propanediol, to obtain the title compound (3.13 g, yield 30~60%).

¹H NMR(400 MHz, CDCl₃) δ1.27(d, J=6.4 Hz, 3H), 2.95 (d, J=3.6 Hz, 1H), 4.73(br s, 2H), 5.01~5.11(m, 2H), 7.01~7.86(m, 4H)

Example 67

Synthesis of 1-(2-iodophenyl)-(S)-1-hydroxybutyl-(S)-2-carbamate (67)

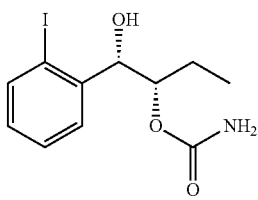 [SMILES: CC[C@H](OC(N)=O)[C@@H](O)c1ccccc1I]

The substantially same method as described in Example 1 was conducted, except that 1-(2-iodophenyl)-(S,S)-1,2-butanediol obtained in Preparation Example 68 was used instead of 1-(2-chlorophenyl)-(S,S)-1,2-propanediol, to obtain the title compound (3.6 g, yield 30~60%).

¹H NMR(400 MHz, CDCl₃) δ1.27(d, J=6.4 Hz, 3H), 3.09 (br s, 1H), 4.83(br s, 2H), 5.00~5.10(m, 2H), 7.00~7.76(m, 4H)

Example 68

Synthesis of 1-(2-chlorophenyl)-(S)-2-hydroxypropyl-(S)-1-carbamate (68)

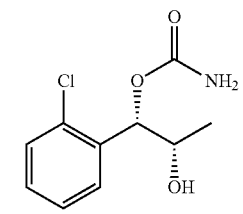

A regioisomer of monocarbamate was separated and purified by conducting the silica gel column chromatography as described in Example 1, to obtain the title compound (0.34 g, yield 10%).

¹H NMR(400 MHz, CDCl₃) δ1.24(d, J=6.8 Hz, 3H), 2.13 (d, J=4.4 Hz, 1H), 4.12~4.16(m, 1H), 4.85(br s, 2H), 5.98(d, J=5.6 Hz, 1H), 7.24~7.43(m, 4H)

Example 69

Synthesis of 1-(2-chlorophenyl)-(R)-2-hydroxypropyl-(R)-1-carbamate (69)

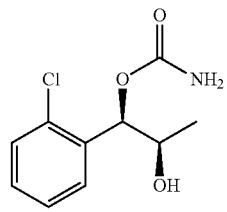

A regioisomer of monocarbamate was separated and purified by conducting the silica gel column chromatography as described in Example 2, to obtain the title compound (0.77 g, yield 16%).

¹H NMR(400 MHz, CDCl₃) δ1.24(d, J=6.4 Hz, 3H), 2.04 (d, J=4.8 Hz, 1H), 4.11~4.18(m, 1H), 4.74(br s, 2H), 6.00(d, J=5.6 Hz, 1H), 7.24~7.43(m, 4H)

Example 70

Synthesis of 1-(2-chlorophenyl)-2-hydroxypropyl-1-carbamate (70)

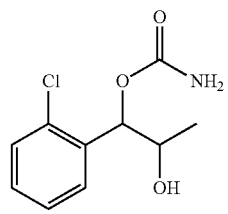

A regioisomer of monocarbamate was separated and purified by conducting the silica gel column chromatography as described in Example 3, to obtain the title compound (0.16 g, yield 10~30%).

¹H NMR(400 MHz, CDCl₃) δ1.24(d, J=6.4 Hz, 3H), 2.04 (d, J=4.8 Hz, 1H), 4.11~4.18(m, 1H), 4.74(br s, 2H), 6.00(d, J=5.6 Hz, 1H), 7.24~7.43(m, 4H)

Example 71

Synthesis of 1-(2-chlorophenyl)-(S)-2-hydroxypropyl-(S)-1-N-methylcarbamate (71)

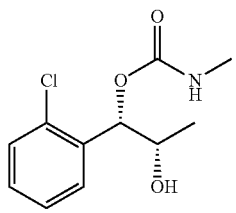 [SMILES: CNC(=O)O[C@@H](c1ccccc1Cl)[C@H](C)O]

A regioisomer of monocarbamate was separated and purified by conducting the silica gel column chromatography as described in Example 15, to obtain the title compound (0.70 g, yield 10~30%).
$^1$H NMR(400 MHz, CDCl$_3$) δ1.21(d, J=6.4 Hz, 3H), 2.80 (d, J=4.8 Hz, 3H), 3.12(s, 1H), 4.09~4.16(m, 1H), 4.86(br s, 1H), 5.99(d, J=6.0 Hz, 1H), 7.23~7.40(m, 4H)

Example 72

Synthesis of 1-(2-chlorophenyl)-(R)-2-hydroxypropyl-(R)-1-N-methylcarbamate (72)

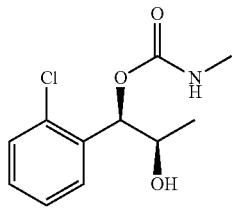 [SMILES: CNC(=O)O[C@H](c1ccccc1Cl)[C@@H](C)O]

A regioisomer of monocarbamate was separated and purified by conducting the silica gel column chromatography as described in Example 22, to obtain the title compound (0.69 g, yield 10~30%).
$^1$H NMR(400 MHz, CDCl$_3$) δ1.21(d, J=6.4 Hz, 3H), 2.80 (d, J=4.8 Hz, 3H), 3.12(s, 1H), 4.09~4.16(m, 1H), 4.86(br s, 1H), 5.99(d, J=6.0 Hz, 1H), 7.23~7.40(m, 4H)

Example 73

Synthesis of 1-(2-chlorophenyl)-2-hydroxypropyl-1-N-methylcarbamate (73)

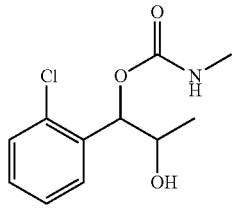 [SMILES: CNC(=O)OC(c1ccccc1Cl)C(C)O]

A regioisomer of monocarbamate was separated and purified by conducting the silica gel column chromatography as described in Example 29, to obtain the title compound (0.73 g, yield 10%).
$^1$H NMR(400 MHz, CDCl$_3$) δ 1.22(d, J=6 Hz, 3H), 2.15(d, J=4 Hz, 1H), 2.81(d, J=5 Hz, 3H), 4.12(dd, J=6 Hz, 1H), 4.83(br s, 1H), 6.00(d, J=6 Hz, 1H), 7.23~7.41(m, 4H)

Example 74

Synthesis of 1-(2-chlorophenyl)-(S)-2-hydroxypropyl-(S)-1-N-propylcarbamate (74)

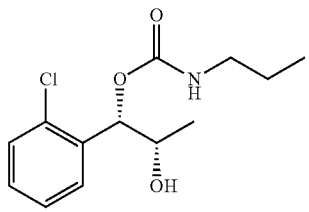 [SMILES: CCCNC(=O)O[C@@H](c1ccccc1Cl)[C@H](C)O]

A regioisomer of monocarbamate was separated and purified by conducting the silica gel column chromatography as described in Example 16, to obtain the title compound (0.15 g, yield 10~30%).
$^1$H NMR(400 MHz, CDCl$_3$) δ 0.91(t, J=7 Hz, 3H), 1.22(d, J=6 Hz, 3H), 1.52(dd, J=7 Hz, 2H), 2.23(d, J=4 Hz, 1H), 3.09~3.21(m, 2H), 4.09~4.17(m, 1H), 4.93(s, 1H), 5.99(d, J=6 Hz, 1H), 7.23~7.47(m, 4H)

Example 75

Synthesis of 1-(2-chlorophenyl)-(R)-2-hydroxypropyl-(R)-1-N-propylcarbamate (75)

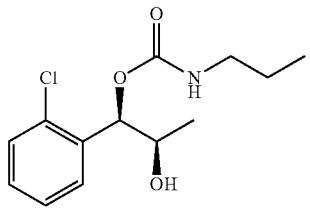 [SMILES: CCCNC(=O)O[C@H](c1ccccc1Cl)[C@@H](C)O]

A regioisomer of monocarbamate was separated and purified by conducting the silica gel column chromatography as described in Example 23, to obtain the title compound (0.04 g, yield 10~30%).
$^1$H NMR(400 MHz, CDCl$_3$) δ 0.91(t, J=7 Hz, 3H), 1.22(d, J=6 Hz, 3H), 1.52(dd, J=7 Hz, 2H), 2.23(d, J=4 Hz, 1H), 3.09~3.21(m, 2H), 4.09~4.17(m, 1H), 4.93(s, 1H), 5.99(d, J=6 Hz, 1H), 7.23~7.47(m, 4H)

Example 76

Synthesis of 1-(2-chlorophenyl)-2-hydroxypropyl-1-N-propylcarbamate (76)

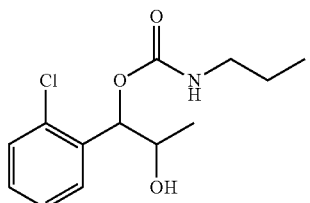

A regioisomer of monocarbamate was separated and purified by conducting the silica gel column chromatography as described in Example 30, to obtain the title compound (0.15 g, yield 10%).

$^1$H NMR(400 MHz, CDCl$_3$) δ 0.91(t, J=7 Hz, 3H), 1.22(d, J=6 Hz, 3H), 1.52(dd, J=7 Hz, 2H), 2.23(d, J=4 Hz, 1H), 3.09~3.21(m, 2H), 4.09~4.17(m, 1H), 4.93(s, 1H), 5.99(d, J=6 Hz, 1H), 7.23~7.47(m, 4H)

Example 77

Synthesis of 1-(2-chlorophenyl)-(S)-2-hydroxypropyl-(S)-1-N-isopropylcarbamate (77)

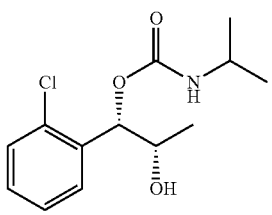 [SMILES: CC(C)NC(=O)O[C@@H](c1ccccc1Cl)[C@H](C)O]

A regioisomer of monocarbamate was separated and purified by conducting the silica gel column chromatography as described in Example 17, to obtain the title compound (0.42 g, yield 28%).

$^1$H NMR(400 MHz, CDCl$_3$) δ1.10(d, J=6.0 Hz, 3H), 1.15~1.19(m, 6H), 2.41(s, 1H), 3.76~4.08(m, 1H), 4.34(s, 1H), 4.83(br s 1H), 5.95(d, J=5.3 Hz, 1H), 7.19~7.39(m, 4H)

Example 78

Synthesis of 1-(2-chlorophenyl)-(R)-2-hydroxypropyl-(R)-1-N-isopropylcarbamate (78)

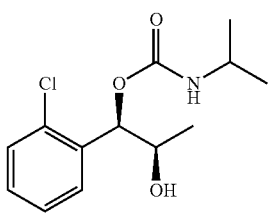 [SMILES: CC(C)NC(=O)O[C@H](c1ccccc1Cl)[C@@H](C)O]

A regioisomer of monocarbamate was separated and purified by conducting the silica gel column chromatography as described in Example 24, to obtain the title compound (0.5 g, yield 10%).

$^1$H NMR(400 MHz, CDCl$_3$) δ1.13(d, J=6 Hz, 3H), 1.20 (dd, J=9.2 Hz, 6H), 2.23(s, 1H), 3.77~3.82(m, 1H), 4.10(s, 1H), 4.76(br s, 1H), 5.98(d, J=5.6 Hz, 1H), 7.23~7.41(m, 4H)

Example 79

Synthesis of 1-(2-chlorophenyl)-2-hydroxypropyl-1-N-isopropylcarbamate (79)

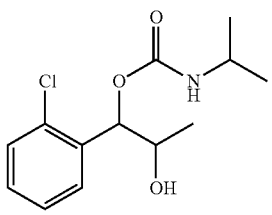 [SMILES: CC(C)NC(=O)OC(c1ccccc1Cl)C(C)O]

A regioisomer of monocarbamate was separated and purified by conducting the silica gel column chromatography as described in Example 31, to obtain the title compound (0.09 g, yield 40%).

$^1$H NMR(400 MHz, CDCl$_3$) δ 1.14(d, J=6 Hz, 3H), 1.21 (dd, J=6 Hz, 6H), 2.16(d, J=5 Hz, 1H), 3.81(t, J=6 Hz, 1H), 4.11(d, J=5 Hz, 1H), 4.73(br s, 1H), 5.98(d, J=5 Hz, 1H), 7.24~741(m, 4H)

Example 80

Synthesis of 1-(2-chlorophenyl)-(S)-2-hydroxypropyl-(S)-1-N-cyclopropylcarbamate (80)

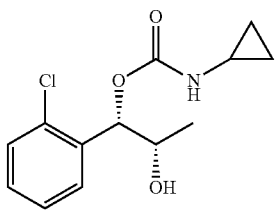 [SMILES: C[C@H](O)[C@@H](OC(=O)NC1CC1)c1ccccc1Cl]

A regioisomer of monocarbamate was separated and purified by conducting the silica gel column chromatography as described in Example 18, to obtain the title compound (0.53 g, yield 10~30%).

$^1$H NMR(400 MHz, CDCl$_3$) δ0.53~0.60(m, 2H), 0.74(s, 2H), 1.21(d, J=6.0 Hz, 3H), 2.19(s, 1H), 2.59(s, 1H), 4.11~4.15(m, 1H), 5.13(br s, 1H), 5.99(d, J=5.20 Hz, 1H), 7.23~7.40(m, 4H)

Example 81

Synthesis of 1-(2-chlorophenyl)-(R)-2-hydroxypropyl-(R)-1-N-cyclopropylcarbamate (81)

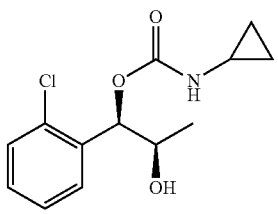 [SMILES: C[C@@H](O)[C@H](OC(=O)NC1CC1)c1ccccc1Cl]

A regioisomer of monocarbamate was separated and purified by conducting the silica gel column chromatography as described in Example 25, to obtain the title compound (0.58 g, yield 10%).

$^1$H NMR(400 MHz, CDCl$_3$) δ0.53~0.60(m, 2H), 0.74(s, 2H), 1.21(d, J=6.0 Hz, 3H), 2.19(s, 1H), 2.59(s, 1H), 4.11~4.15(m, 1H), 5.13(br s, 1H), 5.99(d, J=5.20 Hz, 1H), 7.23~7.40(m, 4H)

Example 82

Synthesis of 1-(2-chlorophenyl)-2-hydroxypropyl-1-N-cyclopropylcarbamate (82)

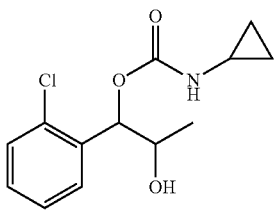 [SMILES: CC(O)C(OC(=O)NC1CC1)c1ccccc1Cl]

A regioisomer of monocarbamate was separated and purified by conducting the silica gel column chromatography as described in Example 32, to obtain the title compound (0.38 g, yield 14%).
$^1$H NMR(400 MHz, CDCl$_3$) δ 0.71(s, 2H), 1.19(d, J=6 Hz, 3H), 2.45(S, 1H), 2.57(S, 1H), 4.08~4.12(m, 1H), 5.26(s, 1H), 5.97(d, J=4 Hz, 1H), 7.22~7.54(m, 4H)

Example 83

Synthesis of 1-(2-chlorophenyl)-(S)-2-hydroxypropyl-(S)-1-N-cyclohexylcarbamate (83)

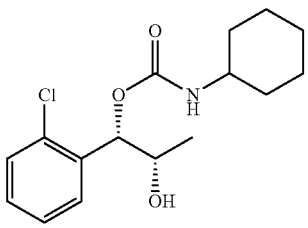 [SMILES: C[C@H](O)[C@@H](OC(=O)NC1CCCCC1)c1ccccc1Cl]

A regioisomer of monocarbamate was separated and purified by conducting the silica gel column chromatography as described in Example 19, to obtain the title compound (0.24 g, yield 10~30%).
$^1$H NMR(400 MHz, CDCl$_3$) δ1.10~1.39(m, 7H), 1.61(s, 3H), 1.71~1.74(m, 2H), 1.87(d, J=11.2 Hz, 1H), 2.48(d, J=10.8 Hz, 1H), 3.46(t, J=4 Hz, 1H), 4.10~4.11(m, 1H), 4.80(br s 1H), 5.97(d, J=5.6 Hz, 1H), 7.23~7.41(m, 4H)

Example 84

Synthesis of 1-(2-chlorophenyl)-(R)-2-hydroxypropyl-(R)-1-N-cyclohexylcarbamate (84)

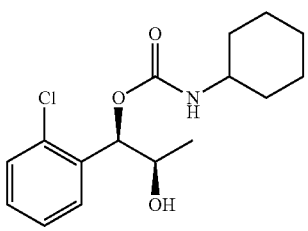 [SMILES: C[C@@H](O)[C@H](OC(=O)NC1CCCCC1)c1ccccc1Cl]

A regioisomer of monocarbamate was separated and purified by conducting the silica gel column chromatography as described in Example 26, to obtain the title compound (0.35 g, yield 10%).
$^1$H NMR(400 MHz, CDCl$_3$) δ1.10~1.39(m, 7H), 1.61(s, 3H), 1.71~1.74(m, 2H), 1.87(d, J=11.2 Hz, 1H), 2.48(d, J=10.8 Hz, 1H), 3.46(t, J=4 Hz, 1H), 4.10~4.11(m, 1H), 4.80(br s 1H), 5.97(d, J=5.6 Hz, 1H), 7.23~7.41(m, 4H)

Example 85

Synthesis of 1-(2-chlorophenyl)-2-hydroxypropyl-1-N-cyclohexylcarbamate (85)

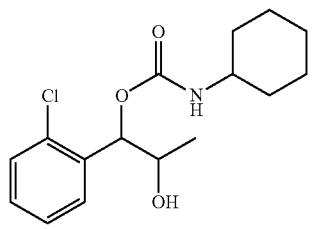 [SMILES: CC(O)C(OC(=O)NC1CCCCC1)c1ccccc1Cl]

A regioisomer of monocarbamate was separated and purified by conducting the silica gel column chromatography as described in Example 33, to obtain the title compound (0.26 g, yield 10%).
$^1$H NMR(400 MHz, CDCl$_3$) δ 1.12~1.19(m, 3H), 1.22(d, J=6 Hz, 3H), 1.27~1.37(m, 1H), 1.71(t, J=6 Hz, 2H), 1.86~1.88(m, 1H), 1.97~2.00(m, 1H), 2.18(d, J=4 Hz, 1H), 3.47(S, 1H), 4.12(t, J=6 Hz, 1H), 4.78(S, 1H), 5.97(d, J=6 Hz, 1H), 7.23~7.40(m, 4H)

Example 86

Synthesis of 1-(2-chlorophenyl)-(S)-2-hydroxypropyl-(S)-1-N-benzylcarbamate (86)

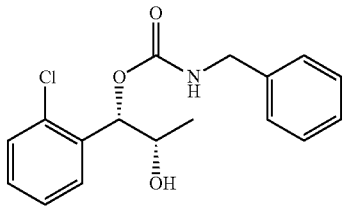 [SMILES: C[C@H](O)[C@@H](OC(=O)NCc1ccccc1)c1ccccc1Cl]

A regioisomer of monocarbamate was separated and purified by conducting the silica gel column chromatography as described in Example 20, to obtain the title compound (0.19 g, yield 10~30%).
$^1$H NMR(400 MHz, CDCl$_3$) δ 1.23(d, J=6 Hz, 3H), 2.16(d, J=4 Hz, 1H), 4.12(t, J=6 Hz, 1H), 4.31~4.44(m, 2H), 5.22(br S, 1H), 6.04(d, J=6 Hz, 1H), 7.27~7.42(m, 9H)

Example 87

Synthesis of 1-(2-chlorophenyl)-(R)-2-hydroxypropyl-(R)-1-N-benzylcarbamate (87)

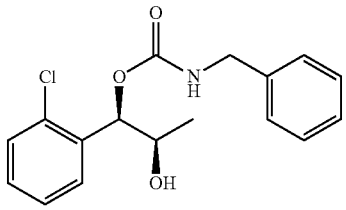 [SMILES: C[C@@H](O)[C@H](OC(=O)NCc1ccccc1)c1ccccc1Cl]

A regioisomer of monocarbamate was separated and purified by conducting the silica gel column chromatography as described in Example 27, to obtain the title compound (0.07 g, yield 10~30%).

$^1$H NMR(400 MHz, CDCl$_3$) δ 1.23(d, J=6 Hz, 3H), 2.16(d, J=4 Hz, 1H), 4.12(t, J=6 Hz, 1H), 4.31~4.44(m, 2H), 5.22(br S, 1H), 6.04(d, J=6 Hz, 1H), 7.27~7.42(m, 9H)

Example 88

Synthesis of 1-(2-chlorophenyl)-2-hydroxypropyl-1-N-benzylcarbamate (88)

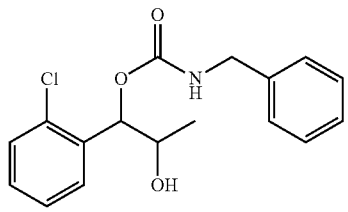 [SMILES: CC(O)C(OC(=O)NCc1ccccc1)c1ccccc1Cl]

A regioisomer of monocarbamate was separated and purified by conducting the silica gel column chromatography as described in Example 34, to obtain the title compound (0.21 g, yield 14%).

$^1$H NMR(400 MHz, CDCl$_3$) δ 1.23(d, J=6 Hz, 3H), 2.16(d, J=4 Hz, 1H), 4.12(t, J=6 Hz, 1H), 4.31~4.44(m, 2H), 5.22(br S, 1H), 6.04(d, J=6 Hz, 1H), 7.27~7.42(m, 9H)

Example 89

Synthesis of 1-(2,4-dichlorophenyl)-(S)-2-hydroxypropyl-(S)-1-carbamate (89)

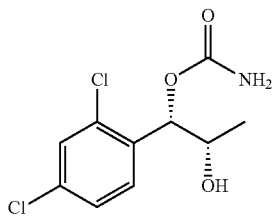 [SMILES: C[C@H](O)[C@@H](OC(N)=O)c1ccc(Cl)cc1Cl]

A regioisomer of monocarbamate was separated and purified by conducting the silica gel column chromatography as described in Example 36, to obtain the title compound (0.05 g, yield 10~30%).

$^1$H NMR(400 MHz, CDCl$_3$) δ1.13(d, J=6.8 Hz, 3H), 2.49 (d, J=4.0 Hz, 1H), 4.66~4.74(m, 1H), 4.76(br s, 2H), 6.20(d, J=8.8 Hz, 1H), 7.30(d, J=8.4 Hz, 1H), 7.39(d, J=2.0 Hz, 2H), 7.50(dd, J=8.4 Hz, 2.0 Hz, 1H)

Example 90

Synthesis of 1-(2,6-dichlorophenyl)-(S)-2-hydroxypropyl-(S)-1-carbamate (90)

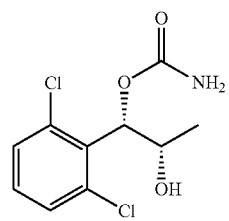 [SMILES: C[C@H](O)[C@@H](OC(N)=O)c1c(Cl)cccc1Cl]

A regioisomer of monocarbamate was separated and purified by conducting the silica gel column chromatography as described in Example 37, to obtain the title compound (0.07 g, yield 24%).

$^1$H NMR(400 MHz, CDCl$_3$) δ1.13(d, J=6.8 Hz, 3H), 2.49 (d, J=4.0 Hz, 1H), 4.66~4.74(m, 1H), 4.76(br s, 2H), 6.20(d, J=8.8 Hz, 1H), 7.25~7.40(m, 3H)

Example 91

Synthesis of 1-(2,3-dichlorophenyl)-(S)-2-hydroxypropyl-(S)-1-carbamate (91)

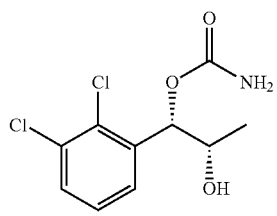 [SMILES: C[C@H](O)[C@@H](OC(N)=O)c1cccc(Cl)c1Cl]

A regioisomer of monocarbamate was separated and purified by conducting the silica gel column chromatography as described in Example 38, to obtain the title compound (0.08 g, yield 10~30%).

$^1$H NMR(400 MHz, CDCl$_3$) δ1.15(d, J=6.4 Hz, 3H), 3.66 (d, J=9.2 Hz, 1H), 4.73(br s, 2H), 5.43(t, J=9.0 Hz, 1H), 5.62~5.69(m, 1H), 7.18~7.22(m, 3H),

Example 92

Synthesis of 1-(2,4-dichlorophenyl)-(S)-2-hydroxybutyl-(S)-1-carbamate (92)

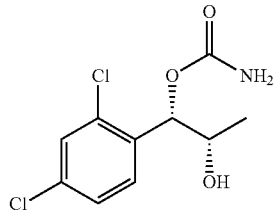 [SMILES: C[C@H](O)[C@@H](OC(N)=O)c1ccc(Cl)cc1Cl]

A regioisomer of monocarbamate was separated and purified by conducting the silica gel column chromatography as described in Example 39, to obtain the title compound (0.07 g, yield 10~30%).

$^1$H NMR(400 MHz, CDCl$_3$) δ0.77(t, J=7.4 Hz, 3H), 0.92~1.01(m, 1H), 1.18~1.28(m, 1H), 4.06~4.13(m, 1H), 4.96(d, J=6.0 Hz, 1H), 5.91(d, J=8.8 Hz, 1H), 6.4(br s, 2H), 7.30~7.50(m, 3H)

Example 93

Synthesis of 1-(2,6-dichlorophenyl)-(S)-2-hydroxy-butyl-(S)-1-carbamate (93)

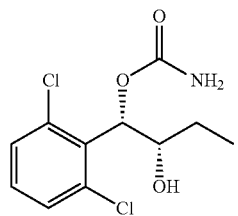

A regioisomer of monocarbamate was separated and purified by conducting the silica gel column chromatography as described in Example 40, to obtain the title compound (0.11 g, yield 29%).

$^1$H NMR(400 MHz, CDCl$_3$) δ0.77(t, J=7.4 Hz, 3H), 0.92~1.01(m, 1H), 1.18~1.28(m, 1H), 4.06~4.13(m, 1H), 4.96(d, J=6.0 Hz, 1H), 5.91(d, J=8.8 Hz, 1H), 6.4(br s, 2H), 7.25~7.40(m, 3H)

Example 94

Synthesis of 1-(2,4-dichlorophenyl)-(S)-2-hydroxy-3-methyl-butyl-(S)-1-carbamate (94)

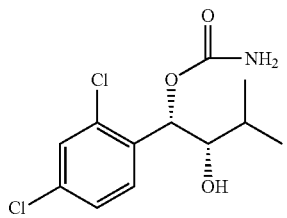 [SMILES: CC(C)[C@H](O)[C@@H](OC(N)=O)c1ccc(Cl)cc1Cl]

A regioisomer of monocarbamate was separated and purified by conducting the silica gel column chromatography as described in Example 41, to obtain the title compound (0.01 g, yield 10~30%).

$^1$H NMR(400 MHz, CDCl$_3$) δ1.00(t, J=7.2 Hz, 6H), 1.73~1.79(m, 1H), 3.67~3.69(m, 1H), 4.96(d, J=6.0 Hz, 1H), 5.91(d, J=8.8 Hz, 1H), 6.42(br s, 2H), 7.30~7.50(m, 3H)

Example 95

Synthesis of 1-(2,6-dichlorophenyl)-(S)-2-hydroxy-3-methyl-butyl-(S)-1-carbamate (95)

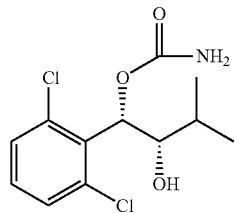

A regioisomer of monocarbamate was separated and purified by conducting the silica gel column chromatography as described in Example 42, to obtain the title compound (0.03 g, yield 10~30%).

$^1$H NMR(400 MHz, CDCl$_3$) δ1.00(t, J=7.2 Hz, 6H), 1.73~1.79(m, 1H), 3.67~3.69(m, 1H), 4.96(d, J=6.0 Hz, 1H), 5.91(d, J=8.8 Hz, 1H), 6.42(br s, 2H), 7.25~7.40(m, 3H)

Example 96

Synthesis of 1-(2,4-dichlorophenyl)-(S)-2-hydroxy-hexyl-(S)-1-carbamate (96)

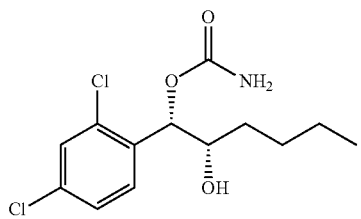 [SMILES: CCCC[C@H](O)[C@@H](OC(N)=O)c1ccc(Cl)cc1Cl]

A regioisomer of monocarbamate was separated and purified by conducting the silica gel column chromatography as described in Example 43, to obtain the title compound (0.21 g, yield 10~30%).

$^1$H NMR(400 MHz, CDCl$_3$) δ0.85(t, J=7.2 Hz, 3H), 1.18~1.33(m, 4H), 1.48~1.55(m, 2H), 2.35(d, J=4.4 Hz, 1H), 4.45~4.50(m, 1H), 4.76(br s, 2H), 6.21(d, J=8.4 Hz, 1H), 7.30~7.50(m, 3H)

Example 97

Synthesis of 1-(2,6-dichlorophenyl)-(S)-2-hydroxy-hexyl-(S)-1-carbamate (97)

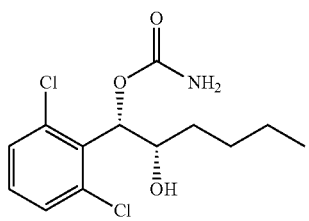

A regioisomer of monocarbamate was separated and purified by conducting the silica gel column chromatography as described in Example 44, to obtain the title compound (0.06 g, yield 29%).

¹H NMR(400 MHz, CDCl₃) δ0.85(t, J=7.2 Hz, 3H), 1.18~1.33(m, 4H), 1.48~1.55(m, 2H), 2.35(d, J=4.4 Hz, 1H), 4.45~4.50(m, 1H), 4.76(br s, 2H), 6.21(d, J=8.4 Hz, 1H), 7.16~7.34(m, 3H)

Example 98

Synthesis of 1-(2,4-dichlorophenyl)-(R)-2-hydroxypropyl-(R)-1-carbamate (98)

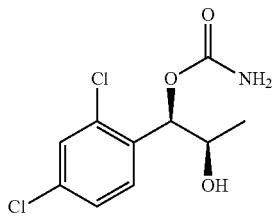 [SMILES: C[C@@H](O)[C@H](OC(N)=O)c1ccc(Cl)cc1Cl]

A regioisomer of monocarbamate was separated and purified by conducting the silica gel column chromatography as described in Example 45, to obtain the title compound (0.04 g, yield 10~30%).
¹H NMR(400 MHz, CDCl₃) δ1.13(d, J=6.8 Hz, 3H), 2.49 (d, J=4.0 Hz, 1H), 4.66~4.74(m, 1H), 4.76(br s, 2H), 6.20(d, J=8.8 Hz, 1H), 7.30~7.50(m, 3H)

Example 99

Synthesis of 1-(2,6-dichlorophenyl)-(R)-2-hydroxypropyl-(R)-1-carbamate (99)

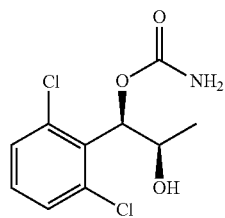 [SMILES: C[C@@H](O)[C@H](OC(N)=O)c1c(Cl)cccc1Cl]

A regioisomer of monocarbamate was separated and purified by conducting the silica gel column chromatography as described in Example 46, to obtain the title compound (0.09 g, yield 10~30%).
¹H NMR(400 MHz, CDCl₃) δ1.13(d, J=6.8 Hz, 3H), 2.49 (d, J=4.0 Hz, 1H), 4.66~4.74(m, 1H), 4.76(br s, 2H), 6.20(d, J=8.8 Hz, 1H), 7.25~7.40(m, 3H)

Example 100

Synthesis of 1-(2,3-dichlorophenyl)-(R)-2-hydroxypropyl-(R)-1-carbamate (100)

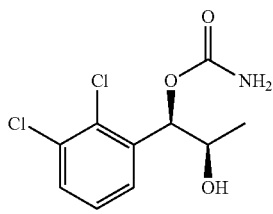 [SMILES: C[C@@H](O)[C@H](OC(N)=O)c1cccc(Cl)c1Cl]

A regioisomer of monocarbamate was separated and purified by conducting the silica gel column chromatography as described in Example 47, to obtain the title compound (0.25 g, yield 10~30%).
¹H NMR(400 MHz, CDCl₃) δ1.15(d, J=6.4 Hz, 3H), 3.66 (d, J=9.2 Hz, 1H), 4.73(br s, 2H), 5.43(t, J=9.0 Hz, 1H), 5.62~5.69(m, 1H), 7.18~7.22(m, 3H), Example 101

Synthesis of 1-(2,4-dichlorophenyl)-(R)-2-hydroxybutyl-(R)-1-carbamate (101)

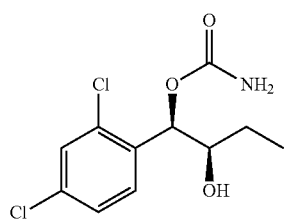 [SMILES: CC[C@@H](O)[C@H](OC(N)=O)c1ccc(Cl)cc1Cl]

A regioisomer of monocarbamate was separated and purified by conducting the silica gel column chromatography as described in Example 48, to obtain the title compound (0.08 g, yield 10~30%).
¹H NMR(400 MHz, CDCl₃) δ0.77(t, J=7.4 Hz, 3H), 0.92~1.01(m, 1H), 1.18~1.28(m, 1H), 4.06~4.13(m, 1H), 4.96(d, J=6.0 Hz, 1H), 5.91(d, J=8.8 Hz, 1H), 6.4(br s, 2H), 7.30~7.50(m, 3H)

Example 102

Synthesis of 1-(2,6-dichlorophenyl)-(R)-2-hydroxybutyl-(R)-1-carbamate (102)

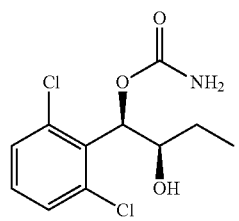 [SMILES: CC[C@@H](O)[C@H](OC(N)=O)c1c(Cl)cccc1Cl]

A regioisomer of monocarbamate was separated and purified by conducting the silica gel column chromatography as described in Example 49, to obtain the title compound (0.09 g, yield 10~30%). ¹H NMR(400 MHz, CDCl₃) δ0.77(t, J=7.4 Hz, 3H), 0.92~1.01(m, 1H), 1.18~1.28(m, 1H), 4.06~4.13(m, 1H), 4.96(d, J=6.0 Hz, 1H), 5.91(d, J=8.8 Hz, 1H), 6.4(br s, 2H), 7.25~7.40(m, 3H)

Example 103

Synthesis of 1-(2,4-dichlorophenyl)-(R)-2-hydroxy-3-methyl-butyl-(R)-1-carbamate (103)

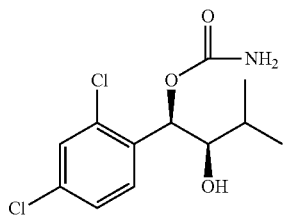 [SMILES: CC(C)[C@@H](O)[C@H](OC(N)=O)c1ccc(Cl)cc1Cl]

A regioisomer of monocarbamate was separated and purified by conducting the silica gel column chromatography as described in Example 50, to obtain the title compound (0.01 g, yield 10~30%).

$^1$H NMR(400 MHz, CDCl$_3$) δ1.00(t, J=7.2 Hz, 6H), 1.73~1.79(m, 1H), 3.67~3.69(m, 1H), 4.96(d, J=6.0 Hz, 1H), 5.91(d, J=8.8 Hz, 1H), 6.42(br s, 2H), 7.30~7.50(m, 3H)

Example 104

Synthesis of 1-(2,6-dichlorophenyl)-(R)-2-hydroxy-3-methyl-butyl-(R)-1-carbamate (104)

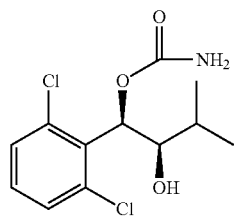 [SMILES: CC(C)[C@@H](O)[C@H](OC(N)=O)c1c(Cl)cccc1Cl]

A regioisomer of monocarbamate was separated and purified by conducting the silica gel column chromatography as described in Example 51, to obtain the title compound (0.01 g, yield 10~30%).

$^1$H NMR(400 MHz, CDCl$_3$) δ1.00(t, J=7.2 Hz, 6H), 1.73~1.79(m, 1H), 3.67~3.69(m, 1H), 4.96(d, J=6.0 Hz, 1H), 5.91(d, J=8.8 Hz, 1H), 6.42(br s, 2H), 7.25~7.40(m, 3H)

Example 105

Synthesis of 1-(2,4-dichlorophenyl)-(R)-2-hydroxy-hexyl-(R)-1-carbamate (105)

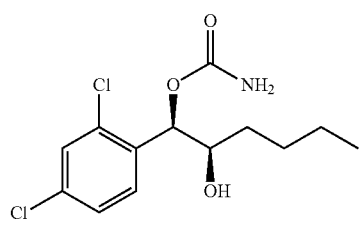 [SMILES: CCCC[C@@H](O)[C@H](OC(N)=O)c1ccc(Cl)cc1Cl]

A regioisomer of monocarbamate was separated and purified by conducting the silica gel column chromatography as described in Example 52, to obtain the title compound (0.21 g, yield 10~30%).

$^1$H NMR(400 MHz, CDCl$_3$) δ0.85(t, J=7.2 Hz, 3H), 1.18~1.33(m, 4H), 1.48~1.55(m, 2H), 2.35(d, J=4.4 Hz, 1H), 4.45~4.50(m, 1H), 4.76(br s, 2H), 6.21(d, J=8.4 Hz, 1H), 7.30~7.50(m, 3H)

Example 106

Synthesis of 1-(2,6-dichlorophenyl)-(R)-2-hydroxy-hexyl-(R)-1-carbamate (106)

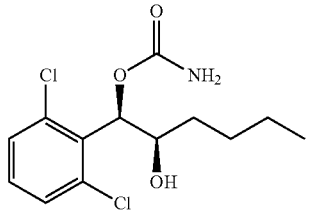 [SMILES: CCCC[C@@H](O)[C@H](OC(N)=O)c1c(Cl)cccc1Cl]

A regioisomer of monocarbamate was separated and purified by conducting the silica gel column chromatography as described in Example 53, to obtain the title compound (0.12 g, yield 10~30%).

$^1$H NMR(400 MHz, CDCl$_3$) δ0.85(t, J=7.2 Hz, 3H), 1.18~1.33(m, 4H), 1.48~1.55(m, 2H), 2.35(d, J=4.4 Hz, 1H), 4.45~4.50(m, 1H), 4.76(br s, 2H), 6.21(d, J=8.4 Hz, 1H), 7.16~7.34(m, 3H)

Example 107

Synthesis of 1-(2,4-dichlorophenyl)-2-hydroxypropyl-1-carbamate (107)

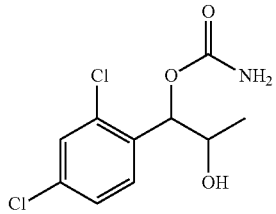 [SMILES: CC(O)C(OC(N)=O)c1ccc(Cl)cc1Cl]

A regioisomer of monocarbamate was separated and purified by conducting the silica gel column chromatography as described in Example 54, to obtain the title compound (0.05 g, yield 10~30%).

$^1$H NMR(400 MHz, CDCl$_3$) δ1.13(d, J=6.8 Hz, 3H), 2.49 (d, J=4.0 Hz, 1H), 4.66~4.74(m, 1H), 4.76(br s, 2H), 6.20(d, J=8.8 Hz, 1H), 7.30~7.50(m, 3H)

Example 108

Synthesis of 1-(2,6-dichlorophenyl)-2-hydroxypropyl-1-carbamate (108)

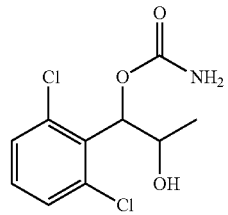 [SMILES: CC(O)C(OC(N)=O)c1c(Cl)cccc1Cl]

A regioisomer of monocarbamate was separated and purified by conducting the silica gel column chromatography as described in Example 55, to obtain the title compound (0.06 g, yield 10~30%).

$^1$H NMR(400 MHz, CDCl$_3$) δ1.13(d, J=6.8 Hz, 3H), 2.49 (d, J=4.0 Hz, 1H), 4.66~4.74(m, 1H), 4.76(br s, 2H), 6.20(d, J=8.8 Hz, 1H), 7.25~7.40(m, 3H)

Example 109

Synthesis of 1-(2,3-dichlorophenyl)-(R)-2-hydroxypropyl-(R)-1-carbamate (109)

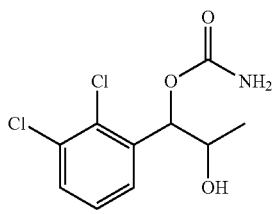 [SMILES: CC(O)C(OC(N)=O)c1cccc(Cl)c1Cl]

A regioisomer of monocarbamate was separated and purified by conducting the silica gel column chromatography as described in Example 56, to obtain the title compound (0.02 g, yield 10~30%).

$^1$H NMR(400 MHz, CDCl$_3$) δ1.15(d, J=6.4 Hz, 3H), 3.66 (d, J=9.2 Hz, 1H), 4.73(br s, 2H), 5.43(t, J=9.0 Hz, 1H), 5.62~5.69(m, 1H), 7.18~7.22(m, 3H),

Example 110

Synthesis of 1-(2,4-dichlorophenyl)-2-hydroxybutyl-1-carbamate (110)

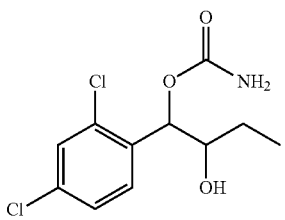 [SMILES: CCC(O)C(OC(N)=O)c1ccc(Cl)cc1Cl]

A regioisomer of monocarbamate was separated and purified by conducting the silica gel column chromatography as described in Example 57, to obtain the title compound (0.07 g, yield 10~30%).

$^1$H NMR(400 MHz, CDCl$_3$) δ0.77(t, J=7.4 Hz, 3H), 0.92~1.01(m, 1H), 1.18~1.28(m, 1H), 4.06~4.13(m, 1H), 4.96(d, J=6.0 Hz, 1H), 5.91(d, J=8.8 Hz, 1H), 6.4(br s, 2H), 7.30~7.50(m, 3H)

Example 111

Synthesis of 1-(2,6-dichlorophenyl)-2-hydroxybutyl-1-carbamate (111)

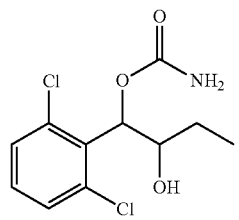 [SMILES: CCC(O)C(OC(N)=O)c1c(Cl)cccc1Cl]

A regioisomer of monocarbamate was separated and purified by conducting the silica gel column chromatography as described in Example 58, to obtain the title compound (0.10 g, yield 10~30%).

$^1$H NMR(400 MHz, CDCl$_3$) δ0.77(t, J=7.4 Hz, 3H), 0.92~1.01(m, 1H), 1.18~1.28(m, 1H), 4.06~4.13(m, 1H), 4.96(d, J=6.0 Hz, 1H), 5.91(d, J=8.8 Hz, 1H), 6.4(br s, 2H), 7.25~7.40(m, 3H)

Example 112

Synthesis of 1-(2,4-dichlorophenyl)-2-hydroxy-3-methyl-butyl-1-carbamate (112)

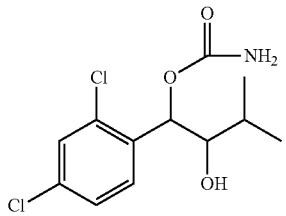 [SMILES: CC(C)C(O)C(OC(N)=O)c1ccc(Cl)cc1Cl]

A regioisomer of monocarbamate was separated and purified by conducting the silica gel column chromatography as described in Example 59, to obtain the title compound (0.04 g, yield 10~30%).

¹H NMR(400 MHz, CDCl₃) δ1.00(t, J=7.2 Hz, 6H), 1.73~1.79(m, 1H), 3.67~3.69(m, 1H), 4.96(d, J=6.0 Hz, 1H), 5.91(d, J=8.8 Hz, 1H), 6.42(br s, 2H), 7.30~7.50(m, 3H)

Example 113

Synthesis of 1-(2,6-dichlorophenyl)-2-hydroxy-3-methyl-butyl-1-carbamate (113)

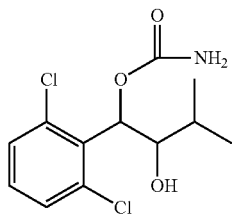 [SMILES: CC(C)C(O)C(OC(N)=O)c1c(Cl)cccc1Cl]

A regioisomer of monocarbamate was separated and purified by conducting the silica gel column chromatography as described in Example 60, to obtain the title compound (0.01 g, yield 10~30%).
¹H NMR(400 MHz, CDCl₃) δ1.00(t, J=7.2 Hz, 6H), 1.73~1.79(m, 1H), 3.67~3.69(m, 1H), 4.96(d, J=6.0 Hz, 1H), 5.91(d, J=8.8 Hz, 1H), 6.42(br s, 2H), 7.25~7.40(m, 3H)

Example 114

Synthesis of 1-(2,4-dichlorophenyl)-2-hydroxyhexyl-1-carbamate (114)

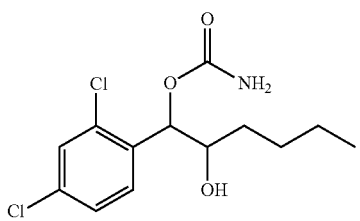 [SMILES: CCCCC(O)C(OC(N)=O)c1ccc(Cl)cc1Cl]

A regioisomer of monocarbamate was separated and purified by conducting the silica gel column chromatography as described in Example 61, to obtain the title compound (0.21 g, yield 10~30%).
¹H NMR(400 MHz, CDCl₃) δ0.85(t, J=7.2 Hz, 3H), 1.18~1.33(m, 4H), 1.48~1.55(m, 2H), 2.35(d, J=4.4 Hz, 1H), 4.45~4.50(m, 1H), 4.76(br s, 2H), 6.21(d, J=8.4 Hz, 1H), 7.30~7.50(m, 3H)

Example 115

Synthesis of 1-(2,6-dichlorophenyl)-2-hydroxyhexyl-1-carbamate (115)

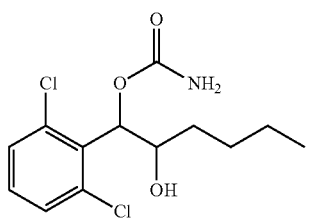 [SMILES: CCCCC(O)C(OC(N)=O)c1c(Cl)cccc1Cl]

A regioisomer of monocarbamate was separated and purified by conducting the silica gel column chromatography as described in Example 62, to obtain the title compound (0.12 g, yield 10~30%).
¹H NMR(400 MHz, CDCl₃) δ0.85(t, J=7.2 Hz, 3H), 1.18~1.33(m, 4H), 1.48~1.55(m, 2H), 2.35(d, J=4.4 Hz, 1H), 4.45~4.50(m, 1H), 4.76(br s, 2H), 6.21(d, J=8.4 Hz, 1H), 7.16~7.34(m, 3H)

Compounds 1 to 115 produced in Examples 1 to 115 were summarized in following Tables 1 and 2.

TABLE 1

Compounds 1 to 67 having the structure of Chemical Formula 1 where 'A' is a carbamoyl derivative and 'B' is H

| No. | X | n (position) | 1ˢᵗ Chiral | 2ⁿᵈ Chiral | $R^1$ | A<br>A = carbamoyl derivative<br>$R^2$ = | B<br>B = H |
|---|---|---|---|---|---|---|---|
| 1 | Cl | 1(2-) | S | S | Me | H | H |
| 2 | Cl | 1(2-) | R | R | Me | H | H |
| 3 | Cl | 1(2-) | Rac. | Rac. | Me | H | H |
| 4 | Cl | 1(2-) | S | R | Me | H | H |
| 5 | Cl | 1(2-) | R | S | Me | H | H |
| 6 | Cl | 1(2-) | S | S | Et | H | H |
| 7 | Cl | 1(2-) | R | R | Et | H | H |
| 8 | Cl | 1(2-) | Rac. | Rac. | Et | H | H |
| 9 | Cl | 1(2-) | S | S | Isopropyl | H | H |
| 10 | Cl | 1(2-) | R | R | Isopropyl | H | H |
| 11 | Cl | 1(2-) | Rac. | Rac. | Isopropyl | H | H |
| 12 | Cl | 1(2-) | S | S | butyl | H | H |
| 13 | Cl | 1(2-) | R | R | butyl | H | H |
| 14 | Cl | 1(2-) | Rac. | Rac. | butyl | H | H |
| 15 | Cl | 1(2-) | S | S | Me | Me | H |
| 16 | Cl | 1(2-) | S | S | Me | Propyl | H |
| 17 | Cl | 1(2-) | S | S | Me | Isopropyl | H |
| 18 | Cl | 1(2-) | S | S | Me | Cyclopropyl | H |

TABLE 1-continued

Compounds 1 to 67 having the structure of Chemical Formula 1 where 'A' is a carbamoyl derivative and 'B' is H

| No. | X | n (position) | 1st Chiral | 2nd Chiral | $R^1$ | A<br>A = carbamoyl derivative<br>$R^2$ = | B<br>B = H |
|---|---|---|---|---|---|---|---|
| 19 | Cl | 1(2-) | S | S | Me | Cyclohexyl | H |
| 20 | Cl | 1(2-) | S | S | Me | Benzyl | H |
| 21 | Cl | 1(2-) | S | S | Me | Bicyclo[2.2.1]heptane | H |
| 22 | Cl | 1(2-) | R | R | Me | Me | H |
| 23 | Cl | 1(2-) | R | R | Me | Propyl | H |
| 24 | Cl | 1(2-) | R | R | Me | Isopropyl | H |
| 25 | Cl | 1(2-) | R | R | Me | Cyclopropyl | H |
| 26 | Cl | 1(2-) | R | R | Me | Cyclohexyl | H |
| 27 | Cl | 1(2-) | R | R | Me | Benzyl | H |
| 28 | Cl | 1(2-) | R | R | Me | Bicyclo[2.2.1]heptane | H |
| 29 | Cl | 1(2-) | Rac. | Rac. | Me | Me | H |
| 30 | Cl | 1(2-) | Rac. | Rac. | Me | Propyl | H |
| 31 | Cl | 1(2-) | Rac. | Rac. | Me | Isopropyl | H |
| 32 | Cl | 1(2-) | Rac. | Rac. | Me | Cyclopropyl | H |
| 33 | Cl | 1(2-) | Rac. | Rac. | Me | Cyclohexyl | H |
| 34 | Cl | 1(2-) | Rac. | Rac. | Me | Benzyl | H |
| 35 | Cl | 1(2-) | Rac, | Rac. | Me | Bicyclo[2.2.1]heptane | H |
| 36 | Cl | 2(2,4-) | S | S | Me | H | H |
| 37 | Cl | 2(2,6-) | S | S | Me | H | H |
| 38 | Cl | 2(2,3-) | S | S | Me | H | H |
| 39 | Cl | 2(2,4-) | S | S | Et | H | H |
| 40 | Cl | 2(2,6-) | S | S | Et | H | H |
| 41 | Cl | 2(2,4-) | S | S | Isopropyl | H | H |
| 42 | Cl | 2(2,6-) | S | S | Isopropyl | H | H |
| 43 | Cl | 2(2,4-) | S | S | butyl | H | H |
| 44 | Cl | 2(2,6-) | S | S | butyl | H | H |
| 45 | Cl | 2(2,4-) | R | R | Me | H | H |
| 46 | Cl | 2(2,6-) | R | R | Me | H | H |
| 47 | Cl | 2(2,3-) | R | R | Me | H | H |
| 48 | Cl | 2(2,4-) | R | R | Et | H | H |
| 49 | Cl | 2(2,6-) | R | R | Et | H | H |
| 50 | Cl | 2(2.4-) | R | R | Isopropyl | H | H |
| 51 | Cl | 2(2,6-) | R | R | Isopropyl | H | H |
| 52 | Cl | 2(2.4-) | R | R | butyl | H | H |
| 53 | Cl | 2(2,6-) | R | R | butyl | H | H |
| 54 | Cl | 2(2,4-) | Rac, | Rac. | Me | H | H |
| 55 | Cl | 2(2,6-) | Rac, | Rac. | Me | H | H |
| 56 | Cl | 2(2,3-) | Rac, | Rac. | Me | H | H |
| 57 | Cl | 2(2,4-) | Rac. | Rac. | Et | H | H |
| 58 | Cl | 2(2,6-) | Rac, | Rac. | Et | H | H |
| 59 | Cl | 2(2,4-) | Rac. | Rac. | Isopropyl | H | H |
| 60 | Cl | 2(2,6-) | Rac. | Rac. | Isopropyl | H | H |
| 61 | Cl | 2(2,4-) | Rac, | Rac. | butyl | H | H |
| 62 | Cl | 2(2,6-) | Rac, | Rac. | butyl | H | H |
| 63 | F | 1(2-) | S | S | Me | H | H |
| 64 | F | 1(2-) | R | R | Me | H | H |
| 65 | I | 1(2-) | S | S | Me | H | H |
| 66 | I | 1(2-) | R | R | Me | H | H |
| 67 | I | 1(2-) | S | S | Et | H | H |

TABLE 2

Compounds 68 to 115 having the structure of Chemical Formula 1 where 'A' is H and 'B' is a carbamoyl derivative

| No. | X | n (position) | 1st Chiral | 2nd Chiral | $R^1$ | A<br>A = H | B<br>B = carbamoyl derivative<br>$R^3$ = |
|---|---|---|---|---|---|---|---|
| 68 | Cl | 1(2-) | S | S | Me | H | H |
| 69 | Cl | 1(2-) | R | R | Me | H | H |
| 70 | Cl | 1(2-) | Rac. | Rac. | Me | H | H |
| 71 | Cl | 1(2-) | S | S | Me | H | Me |
| 72 | Cl | 1(2-) | R | R | Me | H | Me |
| 73 | Cl | 1(2-) | Rac. | Rac. | Me | H | Me |
| 74 | Cl | 1(2-) | S | S | Me | H | Propyl |
| 75 | Cl | 1(2-) | R | R | Me | H | Propyl |
| 76 | Cl | 1(2-) | Rac. | Rac. | Me | H | Propyl |
| 77 | Cl | 1(2-) | S | S | Me | H | Isopropyl |
| 78 | Cl | 1(2-) | R | R | Me | H | Isopropyl |

TABLE 2-continued

Compounds 68 to 115 having the structure of Chemical Formula 1 where 'A' is H and 'B' is a carbamoyl derivative

| No. | X | n (position) | 1st Chiral | 2nd Chiral | R¹ | A<br>A = H | B<br>B = carbamoyl derivative<br>R³ = |
|---|---|---|---|---|---|---|---|
| 79 | Cl | 1(2-) | Rac. | Rac. | Me | H | Isopropyl |
| 80 | Cl | 1(2-) | S | S | Me | H | Cyclopropyl |
| 81 | Cl | 1(2-) | R | R | Me | H | Cyclopropyl |
| 82 | Cl | 1(2-) | Rac. | Rac. | Me | H | Cyclopropyl |
| 83 | Cl | 1(2-) | S | S | Me | H | Cyclohexyl |
| 84 | Cl | 1(2-) | R | R | Me | H | Cyclohexyl |
| 85 | Cl | 1(2-) | Rac. | Rac. | Me | H | Cyclohexyl |
| 86 | Cl | 1(2-) | S | S | Me | H | Benzyl |
| 87 | Cl | 1(2-) | R | R | Me | H | Benzyl |
| 88 | Cl | 1(2-) | Rac. | Rac. | Me | H | Benzyl |
| 89 | Cl | 2(2,4-) | S | S | Me | H | H |
| 90 | Cl | 2(2,6-) | S | S | Me | H | H |
| 91 | Cl | 2(2,3-) | S | S | Me | H | H |
| 92 | Cl | 2(2,4-) | S | S | Et | H | H |
| 93 | Cl | 2(2,6-) | S | S | Et | H | H |
| 94 | Cl | 2(2,4-) | S | S | Isopropyl | H | H |
| 95 | Cl | 2(2,6-) | S | S | Isopropyl | H | H |
| 96 | Cl | 2(2,4-) | S | S | Butyl | H | H |
| 97 | Cl | 2(2,6-) | S | S | Butyl | H | H |
| 98 | Cl | 2(2,4-) | R | R | Me | H | H |
| 99 | Cl | 2(2,6-) | R | R | Me | H | H |
| 100 | Cl | 2(2,3-) | R | R | Me | H | H |
| 101 | Cl | 2(2,4-) | R | R | Et | H | H |
| 102 | Cl | 2(2,6-) | R | R | Et | H | H |
| 103 | Cl | 2(2,4-) | R | R | Isopropyl | H | H |
| 104 | Cl | 2(2,6-) | R | R | Isopropyl | H | H |
| 105 | Cl | 2(2,4-) | R | R | Butyl | H | H |
| 106 | Cl | 2(2,6-) | R | R | Butyl | H | H |
| 107 | Cl | 2(2,4-) | Rac. | Rac. | Me | H | H |
| 108 | Cl | 2(2,6-) | Rac. | Rac. | Me | H | H |
| 109 | Cl | 2(2,3-) | Rac. | Rac. | Me | H | H |
| 110 | Cl | 2(2,4-) | Rac. | Rac. | Et | H | H |
| 111 | Cl | 2(2,6-) | Rac. | Rac. | Et | H | H |
| 112 | Cl | 2(2,4-) | Rac. | Rac. | Isopropyl | H | H |
| 113 | Cl | 2(2,6-) | Rac. | Rac. | Isopropyl | H | H |
| 114 | Cl | 2(2,4-) | Rac. | Rac. | Butyl | H | H |
| 115 | Cl | 2(2,6-) | Rac. | Rac. | Butyl | H | H |

[Animal Testing Examples]

For testing, male mice (ICR) were purchased from ORIENT BIO INC. (Korea), divided into several groups with 6 mice in each group, and were adapted for 4-5 days. The mice having the weight ranging from 19 g to 26 g were employed for the test. The pharmacological effect of the test compounds on muscle relaxation was evaluated by Rotarod test, grip strength test, and muscular force (wire hang) test. All mice were adapted to the test environment at one hour before starting the tests. The pharmacological effects of all the test compounds were evaluated by administration through peritoneal cavity of the mice (10 ul/g, bw).

Experimental Example 1

Measurement of Muscle Relaxation Activity by Endurance Time on a Rotarod Rotating at Accelerated Speed At 24 hours before testing, the mice to be tested were preliminarily trained for 5 minutes on a rod rotating at the rate of 6 revolutions per a minute. The pharmacological effect on muscle relaxation of the test compounds were evaluated by observing the mice on a rod for 5 minutes, where the rod was accelerated from 4 to 40 revolutions per a minute during the test time. The endurance time that each mouse endures on the acceleratedly rotated rod without falling off from the rod was recorded. As test time for evaluation, a maximum of 5 minutes was applied. In case the mouse does not fall off from the rod for testing time, the endurance time was recorded as 5 minutes. All the test compounds were intraperitoneally administered (10 ul/g, bw) to the mice at 15 minutes, 30 minutes, 1 hour, and 2 hours prior to the testing, and the median effective concentration (ED50) was determined at the time that the drug exhibits its maximum pharmacological effect. The obtained results were shown in following Table 3. This experimentation was conducted according to the method described in the reference, 'Monville et al. (2006) Comparison of incremental and accelerating protocol of the rotarod test for the assessment of motor deficits in the 6-OHDA model. J. Neurosci. Meth. 158: 219-223'.

Experimental Example 2

Measurement of Muscle Relaxation Activity by Residence Time on a Rotarod Rotating at a Fixed Speed All the mice to be tested were preliminarily trained for 5 minutes on a rod rotating at the rate of 15 revolutions per a minute. The mice that could not remain on the rod without falling off therefrom for a minimum of 2 minutes were excluded from this testing. After the training, all the mice were allowed to rest for 45-60 minutes. Before the administration of the test compounds, the mice were subjected to a further training for one minute on the rod rotating under the same condition, where the mice falling off from the rod were excluded from this experimentation. All the test compounds were intraperitoneally administered (10 ul/g, bw) to the mice at 15 minutes, 30 minutes, 1 hour, and 2 hours prior to the testing, and the median effective concentration (ED50) was determined at the time (generally 15 min, 30 min or 60 min) that the compounds exhibit their maximum pharmacological effect. In case a mouse stays on the rod until the test is finished, the time was recorded as 10 minutes. As test time for evaluation, a maximum of 10 minutes was applied. The obtained results were shown in following Table 3. This experimentation was conducted according to the method described in the reference, 'Yasuda et al. (2005) Antipyretic, analgesic and muscle relaxant activities of Pueraria isoflavonoids and their metabolites from Pueraria lobata Ohwi—a traditional Chinese drug. Biol. Pharm. Bull. 28: 1224-1228'.

Experimental Example 3

Measurement of Muscle Relaxation Activity by Grip Strength

A grip strength test using the test animals' forelimbs was performed using an instrument equipped with triangle ring and designed so as to easily grip with the forelimbs of experimental animals, manufactured from Ugo Basile Inc. (Ugo Basile, Model 47106, Italy). The test was conducted before and after administration of the compounds to evaluate the effects thereof. All the test compounds were intraperitoneally administered (10 ul/g, bw) at 15 minutes, 30 minutes, 1 hour, and 2 hours before test, and the median effective concentration (ED50) was determined at the time (generally 15 min, 30 min or 60 min) that the compounds exhibits their maximum pharmacological effect. The mouse was made to grip the rod with its forelimbs, and its tail was pulled, where the force at which the mouse detached from the rod was recorded. The instrument indicated the force in grams. All of the mice were given 3 opportunities for test, and the 3 highest values among the test opportunities were selected and the mean value was used as the test result. The obtained results are shown in Table 3. This experimentation was conducted according to the method described in the reference, 'Nevins et al. (1993) Quantitative grip strength assessment as a means of evaluating muscle relaxation in mice. Psychopharmacol. 110: 92-96'.

Experimental Example 4

Measurement of Muscle Relaxation Activity by Wire Hang

This experimentation was conducted using a metal wire of 30 cm in length, which was suspended between two pillars at a height of about 40 cm from the bottom covered with a soft pad. All the test compounds were administered to the mice through peritoneal cavity (10 ul/g, bw) at 15 minutes, 30 minutes, 1 hour, and 2 hours prior to the testing, and the median effective concentration (ED50) was determined at the time that the compound exhibits the maximum pharmacological effect. Each mouse was made to grip the wire using two forelimbs, and the elapse time before the mouse fell off from the wire to the pad on the bottom was recorded in seconds. Each mouse was given 5 opportunities for this test at an interval of 2 minutes period. The highest 3 records among the test opportunities were selected and the mean value was used as the test result. The obtained results are shown in Table 3. This experimentation was conducted according to the method described in the reference, 'Jacqueline N. Crawley (1999) Behavioral phenotyping of transgenic and knockout mice: experimental design and evaluation of general health, sensory functions, motor abilities, and specific behavioral tests. Brain Res. 835: 18-26'.

[Statistical Analysis]

The obtained results are shown as mean±sem. The difference between the groups was statistically analyzed by ANOVA, and then, further examined by Dunnett's test or Bonferroni test. If p is less than 0.05, it was determined that the difference between the groups had statistical significance.

[Results]

The results of muscle relaxation activity of the phenyl carbamate compounds measured in above Experimental Examples 1 to 4 are shown in following Table 3. In the Table 3, the ED50 was represented by the concentration where the compound shows the 50% of muscle relaxation activity compared to the vehicle only (100%).

TABLE 3

Results of the measurements of muscle relaxation activity of the phenyl carbamate compounds

| | MR test (ED50; mg/kg, bw) | | | | |
| --- | --- | --- | --- | --- | --- |
| No. | I | II | III | IV | control |
| 1 | 39.7 | 23.3 | 40.9 | 13.3 | 1 |
| 2 | 66.3 | 76.5 | 110.0 | 43.3 | 1 |
| 3 | 57.1 | 47.7 | 72.6 | 34.0 | 1 |
| 4 | 69.3 | 65.0 | 124.2 | 40.0 | 1 |
| 5 | 66.9 | 65.5 | 95.0 | 52.5 | 1 |
| 6 | — | — | 70.7 | — | 1 |
| 7 | — | — | 248.4 | — | 1 |
| 8 | 50.6 | — | 69.5 | — | 1 |
| 9 | — | — | 103.9 | — | 1 |
| 11 | 102.5 | — | 126.1 | — | 1 |
| 15 | 51.4 | 42.8 | 83.6 | 25.4 | 1 |
| 16 | 48.7 | 61.6 | 67.8 | 16.1 | 2 |
| 17 | 73.1 | 66.4 | 91.5 | 41.4 | 2 |
| 18 | 59.2 | 61.2 | 87.4 | 29.5 | 2 |
| 19 | 95.3 | — | 109.8 | 28.5 | 2 |
| 22 | 25.7 | 25.1 | 28.3 | 22.4 | 1 |
| 23 | — | — | 73.8 | 46.0 | 2 |
| 24 | 38.6 | 44.3 | 48.8 | 17.8 | 2 |
| 25 | 30.0 | 18.3 | 46.1 | 32.9 | 1 |
| 26 | — | — | — | 63.8 | 2 |
| 29 | 30.2 | 41.0 | 46.0 | 38.0 | 2 |
| 30 | — | — | 65.4 | 31.7 | 2 |
| 31 | — | — | 50.4 | 52.1 | 1 |
| 32 | — | — | 45.2 | 36.6 | 2 |
| 33 | — | — | — | 74.6 | 2 |
| 63 | | | 118.3 | 100$^a$ (84.2%) | 1 |
| 64 | | | 120$^a$ (35.4%) | 100$^a$ (30.8%) | 1 |
| 65 | | 28.0 | 42.9 | 23.4 | 2 |
| 66 | | 67.9 | 46.0 | 76.3 | 2 |
| 67 | | 30.2 | 69.1 | 26.2 | 2 |

I = Acc. Rotatod (accelerated rotating ratarod test; Experimental Example 1),
II = Fixed 15 r.p.m. Rotarod (constantly rotating ratarod test; Experimental Example 2),
III = Grip strength (Experimental Example 3),
IV = Wire hang (Experimental Example 4)
$^a$ = the concentration administered and effect (%) compared to that of control treated with vehicle only
Control 1: administered with vehicle only (Vehicle 1: 30% PEG400(Polyethylene Glycol 400))
Control 2: administered with vehicle only (Vehicle 2: 20% Tween 80)

What is claimed is:

1. A compound is selected from the group consisting of:
1-(2-chlorophenyl)-1-hydroxyproply-2-carbamate,
1-(2-chlorophenyl)-1-hydroxy-3-methyl-butyl-2-carbamate,
1-(2-chlorophenyl)-1-hydroxyhexyl-2-carbamate, 1-(2-chlorophenyl)-1-hydroxypropyl-2-N-methylcarbamate,
1-(2-chlorophenyl)-1-hydroxypropyl-2-N-propylcarbamate,
1-(2-chlorophenyl)-1-hydroxypropyl-2-N-isopropylcarbamate,
1-(2-chlorophenyl)-1-hydroxypropyl-2-N-cyclopropylcarbamate,
1-(2-chlorophenyl)-1-hydroxypropyl-2-N-cyclohexylcarbamate,
1-(2-chlorophenyl)-1-hydroxypropyl-2-N-benzylcarbamate,
1-(2-chlorophenyl)-1-hydroxypropyl-2-N-bicyclo[2,2,1]heptanecarbamate,
1-(2,4-dichlorophenyl)-1-hydroxypropyl-2-carbamate,
1-(2,6-dichlorophenyl)-1-hydroxypropyl-2-carbamate,
1-(2,4-dichlorophenyl)-1-hydroxy-3-methyl-butyl-2-carbamate,
1-(2,6-dichlorophenyl)-1-hydroxy-3-methyl-butyl-2-carbamate,
1-(2,4-dichlorophenyl)-1-hydroxyhexyl-2-carbamate,
1-(2,6-dichlorophenyl)-1-hydroxyhexyl-2-carbamate,
1-(2-chlorophenyl)-2-hydroxypropyl-1-carbamate,
1-(2-chlorophenyl)-2-hydroxypropyl-1-N-methylcarbamate,
1-(2-chlorophenyl)-2-hydroxypropyl-1-N-propylcarbamate,
1-(2-chlorophenyl)-2-hydroxypropyl-1-N-isopropylcarbamate,
1-(2-chlorophenyl)-2-hydroxypropyl-1-N-cyclopropylcarbamate,
1-(2-chlorophenyl)-2-hydroxypropyl-1-N-cyclohexylcarbamate,
1-(2-chlorophenyl)-2-hydroxypropyl-1-N-benzylcarbamate,
1-(2,4-dichlorophenyl)-2-hydroxypropyl-1-carbamate,
1-(2,6-dichlorophenyl)-2-hydroxypropyl-1-carbamate,
1-(2,4-dichlorophenyl)-2-hydroxybutyl-1-carbamate,
1-(2,4-dichlorophenyl)-2-hydroxy-3-methyl-butyl-1-carbamate,
1-(2,6-dichlorophenyl)-2-hydroxy-3-methyl-butyl-1-carbamate,
1-(2,4-dichlorophenyl)-2-hydroxyhexyl-1-carbamate,
1-(2,6-dichlorophenyl)-2-hydroxyhexyl-1-carbamate,
1-(2-fluorophenyl)-1-hydroxypropyl-2-carbamate,
1-(2-iodophenyl)-1-hydroxypropyl-2-carbamate,
1-(2-iodophenyl)-1-hydroxybutyl-2-carbamate,
1-(2,3-dichlorophenyl)-1-hydroxypropyl-2-carbamate, and
1-(2,3-dichlorophenyl)-2-hydroxypropyl-1-carbamate; or a pharmaceutically acceptable salt thereof, wherein the compound is in the form of racemate, enantiomer, diastereomer, a mixture of enantiomer, or a mixture of diastereomer.

2. A compound or a pharmaceutically acceptable salt thereof selected from the group consisting of:
1-(2-chlorophenyl)-(S)-1-hydroxypropyl-(S)-2-carbamate,
1-(2-chlorophenyl)-(R)-1-hydroxypropyl-(R)-2-carbamate,
racemate of 1-(2-chlorophenyl)-(S)-1-hydroxypropyl-(S)-2-carbamate and 1-(2-chlorophenyl)-(R)-1-hydroxypropyl-(R)-2-carbamate,
1-(2-chlorophenyl)-(R)-1-hydroxypropyl-(S)-2-carbamate,
1-(2-chlorophenyl)-(S)-1-hydroxypropyl-(R)-2-carbamate,
1-(2-chlorophenyl)-(S)-1-hydroxy-3-methyl-butyl-(S)-2-carbamate,
racemate of 1-(2-chlorophenyl)-(S)-1-hydroxy-3-methyl-butyl-(S)-2-carbamate and 1-(2-chlorophenyl)-(R)-1-hydroxy-3-methyl-butyl-(R)-2-carbamate,
1-(2-chlorophenyl)-(S)-1-hydroxypropyl-(S)-2-N-methylcarbamate,
1-(2-chlorophenyl)-(S)-1-hydroxypropyl-(S)-2-N-propylcarbamate,
1-(2-chlorophenyl)-(S)-1-hydroxypropyl-(R)-2-N-isopropylcarbamate,
1-(2-chlorophenyl)-(S)-1-hydroxypropyl-(S)-2-N-cyclopropylcarbamate,
1-(2-chlorophenyl)-(S)-1-hydroxypropyl-(S)-2-N-cyclohexyl carbamate,
1-(2-chlorophenyl)-(R)-1-hydroxypropyl-(R)-2-N-methylcarbamate,
1-(2-chlorophenyl)-(R)-1-hydroxypropyl-(R)-2-N-propylcarbamate,
1-(2-chlorophenyl)-(R)-1-hydroxypropyl-(R)-2-N-isopropylcarbamate,
1-(2-chlorophenyl)-(R)-1-hydroxypropyl-(R)-2-N-cyclopropylcarbamate,
1-(2-chlorophenyl)-(R)-1-hydroxypropyl-(R)-2-N-cyclohexyl carbamate,
racemate of 1-(2-chlorophenyl)-(S)-1-hydroxypropyl-(S)-2-N-methylcarbamate and 1-(2-chlorophenyl)-(R)-1-hydroxypropyl-(R)-2-N-methylcarbamate
racemate of 1-(2-chlorophenyl)-(S)-1-hydroxypropyl-(S)-2-N-propylcarbamate and 1-(2-chlorophenyl)-(R)-1-hydroxypropyl-(R)-2-N-propylcarbamate,
racemate of 1-(2-chlorophenyl)-(S)-1-hydroxypropyl-(S)-2-N-isopropylcarbamate and 1-(2-chlorophenyl)-(R)-1-hydroxypropyl-(R)-2-N-isopropylcarbamate,
racemate of 1-(2-chlorophenyl)-(S)-1-hydroxypropyl-(S)-2-N-cyclopropylcarbamate and 1-(2-chlorophenyl)-(R)-1-hydroxypropyl-(R)-2-N-cyclopropylcarbamate,
racemate of 1-(2-chlorophenyl)-(S)-1-hydroxypropyl-(S)-2-N-cyclohexylcarbamate and 1-(2-chlorophenyl)-(R)-1-hydroxypropyl-(R)-2-N-cyclohexylcarbamate,
1-(2-fluorophenyl)-(S)-1-hydroxypropyl-(S)-2-carbamate,
1-(2-fluorophenyl)-(R)-1-hydroxypropyl-(R)-2-carbamate,
1-(2-iodophenyl)-(S)-1-hydroxypropyl-(S)-2-carbamate,
1-(2-iodophenyl)-(R)-1-hydroxypropyl-(R)-2-carbamate, and
1-(2-iodophenyl)-(S)-1-hydroxybutyl-(S)-2-carbamate.

3. A method of muscle relaxation comprising administering to a subject in need of muscle relaxation, a therapeutically effective amount of a compound or a pharmaceutically acceptable salt thereof selected from the group consisting of:
1-(2-chlorophenyl)-(S)-1-hydroxypropyl-(S)-2-carbamate,
1-(2-chlorophenyl)-(R)-1-hydroxypropyl-(R)-2-carbamate,
Racemate of 1-(2-chlorophenyl)-(S)-1-hydroxypropyl-(S)-2-carbamate and 1-(2-chlorophenyl)-(R)-1-hydroxypropyl-(R)-2-carbamate,
1-(2-chlorophenyl)-(R)-1-hydroxypropyl-(S)-2-carbamate,
1-(2-chlorophenyl)-(S)-1-hydroxypropyl-(R)-2-carbamate,
1-(2-chlorophenyl)-(S)-1-hydroxy-3-methyl-butyl-(S)-2-carbamate, Racemate of 1-(2-chlorophenyl)-(S)-1-hydroxy-3-methyl-butyl-(S)-2-carbamate and 1-(2-chlorophenyl)-(R)-1-hydroxy-3-methyl-butyl-(R)-2-carbamate,
1-(2-chlorophenyl)-(S)-1-hydroxypropyl-(S)-2-N-methylcarbamate,
1-(2-chlorophenyl)-(S)-1-hydroxypropyl-(S)-2-N-propylcarbamate,
1-(2-chlorophenyl)-(S)-1-hydroxypropyl-(S)-2-N-isopropylcarbamate,
1-(2-chlorophenyl)-(S)-1-hydroxypropyl-(S)-2-N-cyclopropylcarbamate,
1-(2-chlorophenyl)-(S)-1-hydroxypropyl-(S)-2-N-cyclohexyl carbamate,
1-(2-chlorophenyl)-(R)-1-hydroxypropyl-(R)-2-N-methylcarbamate,
1-(2-chlorophenyl)-(R)-1-hydroxypropyl-(R)-2-N-propylcarbamate,
1-(2-chlorophenyl)-(R)-1-hydroxypropyl-(R)-2-N-isopropylcarbamate,
1-(2-chlorophenyl)-(R)-1-hydroxypropyl-(R)-2-N-cyclopropylcarbamate,
1-(2-chlorophenyl)-(R)-1-hydroxypropyl-(R)-2-N-cyclohexyl carbamate,
Racemate of 1-(2-chlorophenyl)-(S)-1-hydroxypropyl-(S)-2-N-methylcarbamate and 1-(2-chlorophenyl)-(R)-1-hydroxypropyl-(R)-2-N-methylcarbamate
Racemate of 1-(2-chlorophenyl)-(S)-1-hydroxypropyl-(S)-2-N-propylcarbamate and 1-(2-chlorophenyl)-(R)-1-hydroxypropyl-(R)-2-N-propylcarbamate,
Racemate of 1-(2-chlorophenyl)-(S)-1-hydroxypropyl-(S)-2-N-isopropylcarbamate and 1-(2-chlorophenyl)-(R)-1-hydroxypropyl-(R)-2-N-isopropylcarbamate,
Racemate of 1-(2-chlorophenyl)-(S)-1-hydroxypropyl-(S)-2-N-cyclopropylcarbamate and 1-(2-chlorophenyl)-(R)-1-hydroxypropyl-(R)-2-N-cyclopropylcarbamate,
Racemate of 1-(2-chlorophenyl)-(S)-1-hydroxypropyl-(S)-2-N-cyclohexylcarbamate and 1-(2-chlorophenyl)-(R)-1-hydroxypropyl-(R)-2-N-cyclohexylcarbamate,
1-(2-fluorophenyl)-(S)-1-hydroxypropyl-(S)-2-carbamate,
1-(2-fluorophenyl)-(R)-1-hydroxypropyl-(R)-2-carbamate,
1-(2-iodophenyl)-(S)-1-hydroxypropyl-(S)-2-carbamate,
1-(2-iodophenyl)-(R)-1-hydroxypropyl-(R)-2-carbamate, and
1-(2-iodophenyl)-(S)-1-hydroxybutyl-(S)-2-carbamate.

4. A method of treating a disease associated with muscle spasm comprising administering to a subject in need of the treatment of a disease associated with muscle spasm selected from the group consisting of herniation of intervertebral disk, vascular disorders of the spinal cord, spastic spinal paralysis, cervical spondylosis, cerebral palsy, sequelae of injuries, and spinocerebellar degeneration, a therapeutically effective amount of a compound or a pharmaceutically acceptable salt thereof selected from the group consisting of:
1-(2-chlorophenyl)-(S)-1-hydroxypropyl-(S)-2-carbamate,
1-(2-chlorophenyl)-(R)-1-hydroxypropyl-(R)-2-carbamate,
Racemate of 1-(2-chlorophenyl)-(S)-1-hydroxypropyl-(S)-2-carbamate and 1-(2-chlorophenyl)-(R)-1-hydroxypropyl-(R)-2-carbamate,
1-(2-chlorophenyl)-(R)-1-hydroxypropyl-(S)-2-carbamate,
1-(2-chlorophenyl)-(S)-1-hydroxypropyl-(R)-2-carbamate,
1-(2-chlorophenyl)-(S)-1-hydroxy-3-methyl-butyl-(S)-2-carbamate,
Racemate of 1-(2-chlorophenyl)-(S)-1-hydroxy-3-methyl-butyl-(S)-2-carbamate and 1-(2-chlorophenyl)-(R)-1-hydroxy-3-methyl-butyl-(R)-2-carbamate,
1-(2-chlorophenyl)-(S)-1-hydroxypropyl-(S)-2-N-methylcarbamate,
1-(2-chlorophenyl)-(S)-1-hydroxypropyl-(S)-2-N-propylcarbamate,
1-(2-chlorophenyl)-(S)-1-hydroxypropyl-(S)-2-N-isopropylcarbamate,
1-(2-chlorophenyl)-(S)-1-hydroxypropyl-(S)-2-N-cyclopropylcarbamate,
1-(2-chlorophenyl)-(S)-1-hydroxypropyl-(S)-2-N-cyclohexyl carbamate,
1-(2-chlorophenyl)-(R)-1-hydroxypropyl-(R)-2-N-methylcarbamate,
1-(2-chlorophenyl)-(R)-1-hydroxypropyl-(R)-2-N-propylcarbamate,
1-(2-chlorophenyl)-(R)-1-hydroxypropyl-(R)-2-N-isopropylcarbamate,
1-(2-chlorophenyl)-(R)-1-hydroxypropyl-(R)-2-N-cyclopropylcarbamate,
1-(2-chlorophenyl)-(R)-1-hydroxypropyl-(R)-2-N-cyclohexyl carbamate,
Racemate of 1-(2-chlorophenyl)-(S)-1-hydroxypropyl-(S)-2-N-methylcarbamate and 1-(2-chlorophenyl)-(R)-1-hydroxypropyl-(R)-2-N-methylcarbamate
Racemate of 1-(2-chlorophenyl)-(S)-1-hydroxypropyl-(S)-2-N-propylcarbamate and 1-(2-chlorophenyl)-(R)-1-hydroxypropyl-(R)-2-N-propylcarbamate,
Racemate of 1-(2-chlorophenyl)-(S)-1-hydroxypropyl-(S)-2-N-isopropylcarbamate and 1-(2-chlorophenyl)-(R)-1-hydroxypropyl-(R)-2-N-isopropylcarbamate,
Racemate of 1-(2-chlorophenyl)-(S)-1-hydroxypropyl-(S)-2-N-cyclopropylcarbamate and 1-(2-chlorophenyl)-(R)-1-hydroxypropyl-(R)-2-N-cyclopropylcarbamate,
Racemate of 1-(2-chlorophenyl)-(S)-1-hydroxypropyl-(S)-2-N-cyclohexylcarbamate and 1-(2-chlorophenyl)-(R)-1-hydroxypropyl-(R)-2-N-cyclohexylcarbamate,
1-(2-fluorophenyl)-(S)-1-hydroxypropyl-(S)-2-carbamate,
1-(2-fluorophenyl)-(R)-1-hydroxypropyl-(R)-2-carbamate,
1-(2-iodophenyl)-(S)-1-hydroxypropyl-(S)-2-carbamate,
1-(2-iodophenyl)-(R)-1-hydroxypropyl-(R)-2-carbamate, and
1-(2-iodophenyl)-(S)-1-hydroxybutyl-(S)-2-carbamate.

5. The compound 1-(2-chlorophenyl)-(S)-1-hydroxypropyl-(S)-2-carbamate or a pharmaceutically acceptable salt thereof.

6. A pharmaceutical composition comprising the compound of claim 5 and one or more pharmaceutically acceptable components.

7. A method of muscle relaxation comprising administering to a subject in need of muscle relaxation, a therapeutically effective amount of the compound of claim 5 or a pharmaceutically acceptable salt thereof.

8. A method of treating a disease associated with muscle spasm comprising administering to a subject in need of the treatment of a disease associated with muscle spasm selected from the group consisting of herniation of intervertebral disk, vascular disorders of the spinal cord, spastic spinal paralysis, cervical spondylosis, cerebral palsy, sequelae of injuries, and spinocerebellar degeneration, a therapeutically effective amount of the compound of claim 5 or a pharmaceutically acceptable salt thereof.

* * * * *

UNITED STATES PATENT AND TRADEMARK OFFICE
CERTIFICATE OF CORRECTION

PATENT NO. : 9,018,253 B2  
APPLICATION NO. : 13/175025  
DATED : April 28, 2015  
INVENTOR(S) : Yong Moon Choi Page 1 of 1

It is certified that error appears in the above-identified patent and that said Letters Patent is hereby corrected as shown below:

Title page, item (73), in "Assignee", in column 1, line 1, after "Ltd.", insert --, Gyeonggi-do--, therefor

Claims

In column 84, line 64, in Claim 1, delete "hydroxyproply" and insert --hydroxypropyl--, therefor In column 86, line 10-11, in Claim 2, delete "1-(2-cholophenyl)-(S)-1-hydroxypropyl-(R)-2-N-isopropylcarbamate," and insert --1-(2-cholophenyl)-(S)-1-hydroxypropyl-(S)-2-N-isopropylcarbamate,--, therefor In column 86, line 28, in Claim 2, after "methylcarbamate", insert --,--, therefor In column 87, line 25, in Claim 3, after "methylcarbamate", insert --,--, therefor In column 88, line 26, in Claim 4, after "methylcarbamate", insert --,--, therefor Signed and Sealed this
Thirteenth Day of October, 2015

Michelle K. Lee
*Director of the United States Patent and Trademark Office*